United States Patent
Park et al.

(10) Patent No.: US 11,197,885 B2
(45) Date of Patent: Dec. 14, 2021

(54) COLLAGEN ENHANCING AGENT MADE FROM LOW ACYL GELLAN GUM, METHODS OF MAKING AND METHODS OF USING THE SAME

(71) Applicant: The University of Toledo, Toledo, OH (US)

(72) Inventors: Joshua J. Park, Toledo, OH (US); Dong-Shik Kim, Toledo, OH (US)

(73) Assignee: The University of Toledo, Toledo, OH (US)

( * ) Notice: Subject to any disclaimer, the term of this patent is extended or adjusted under 35 U.S.C. 154(b) by 531 days.

(21) Appl. No.: 15/447,620

(22) Filed: Mar. 2, 2017

(65) Prior Publication Data

US 2017/0173068 A1    Jun. 22, 2017

Related U.S. Application Data

(63) Continuation-in-part of application No. PCT/US2016/017734, filed on Feb. 12, 2016.

(60) Provisional application No. 62/115,777, filed on Feb. 13, 2015, provisional application No. 62/115,781, filed on Feb. 13, 2015, provisional application No. 62/115,786, filed on Feb. 13, 2015.

(51) Int. Cl.
*A61K 31/715* (2006.01)
*A61K 9/00* (2006.01)
*A61K 9/06* (2006.01)

(52) U.S. Cl.
CPC .......... *A61K 31/715* (2013.01); *A61K 9/0073* (2013.01); *A61K 9/06* (2013.01)

(58) Field of Classification Search
CPC ................................ A61K 31/715; A61K 9/06
USPC ........................................................ 514/547
See application file for complete search history.

(56) References Cited

U.S. PATENT DOCUMENTS

| | | | |
|---|---|---|---|
| 5,401,659 A * | 3/1995 | Thorne | C04B 24/38 435/104 |
| 5,935,604 A * | 8/1999 | Illum | A61K 9/0043 424/501 |
| 2007/0129430 A1* | 6/2007 | Miyata | A61K 8/65 514/474 |

OTHER PUBLICATIONS

Canadas et al. ("Development of novel bilayered structures to be used as an osteochondra in vitro model", TS20, J. Tissue Engineering and Regenerative Medicine 2013:7 (sup. 1): 6-52) (Year: 2013).*

* cited by examiner

*Primary Examiner* — Shaojia A Jiang
*Assistant Examiner* — Everett White
(74) *Attorney, Agent, or Firm* — MacMillan, Sobanski & Todd, LLC

(57) ABSTRACT

Described herein are materials and methods useful for the treatment of neurodegenerative disorders and bone disorders, as well as healing wounds, in a subject. Materials described herein include polysaccharide digestive products resulting from the enzymatic hydrolysis of low acyl gellan gum. Also described herein are pharmaceutical compositions comprising one or more of such materials, and methods for their preparation and use.

5 Claims, 48 Drawing Sheets
(38 of 48 Drawing Sheet(s) Filed in Color)

Mean ± SEM, n = 3
*: P<0.01 compared to control

*: p<0.001 compared to mock
*: p<0.001 compared to treatment with free radicals minus mGAGR

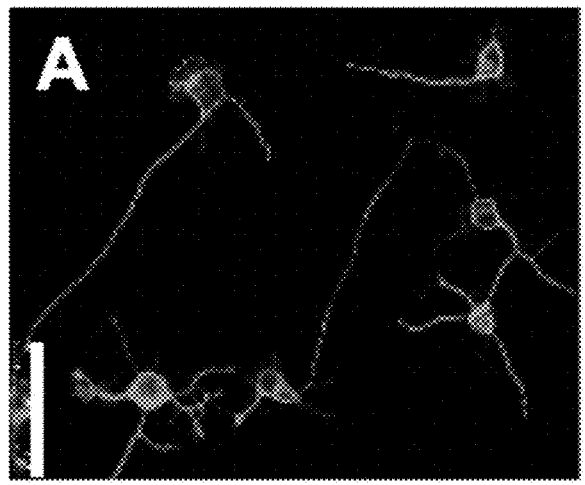
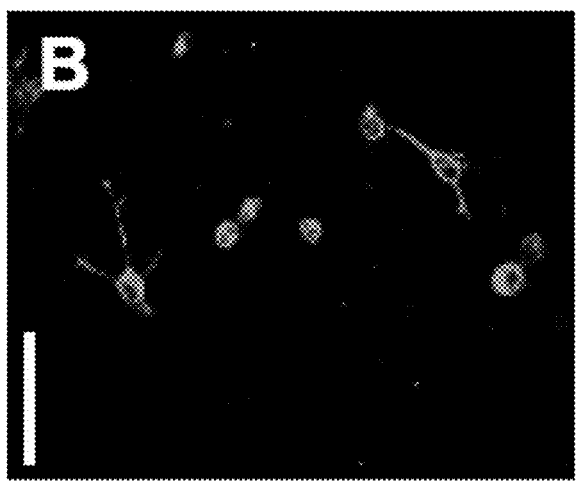
FIG. 22A            FIG. 22B
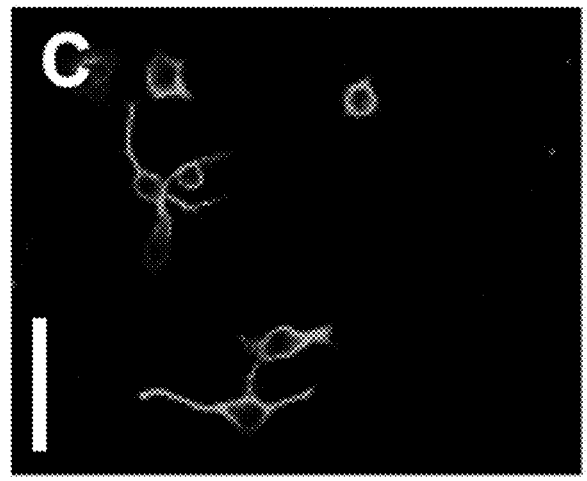
FIG. 22C
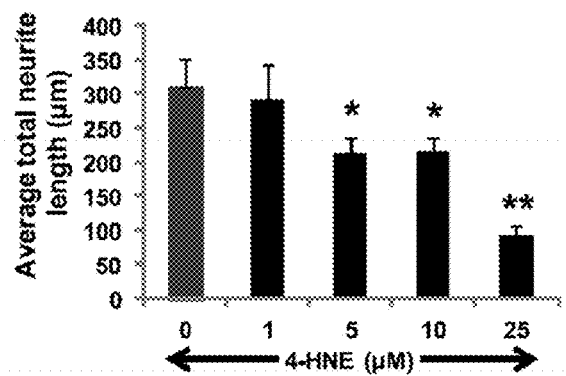
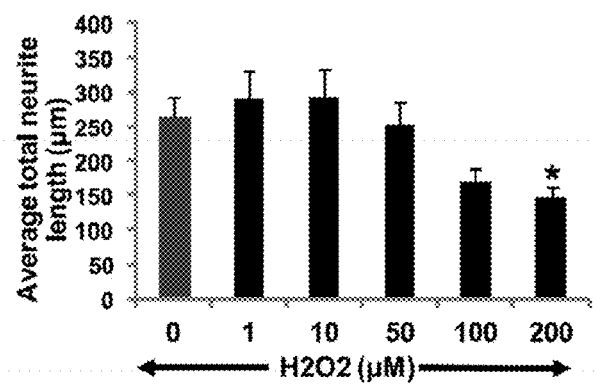
FIG. 22D            FIG. 22E

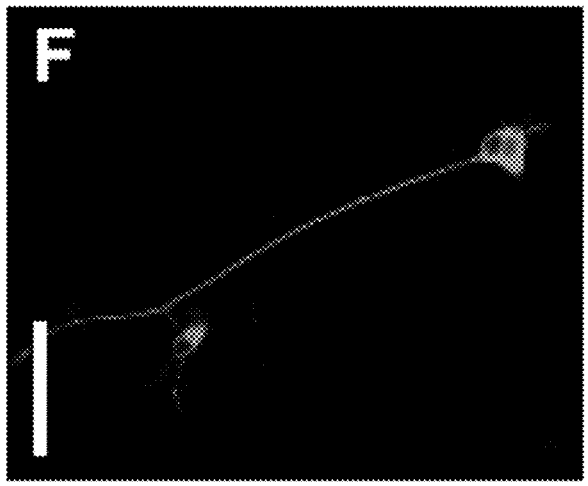
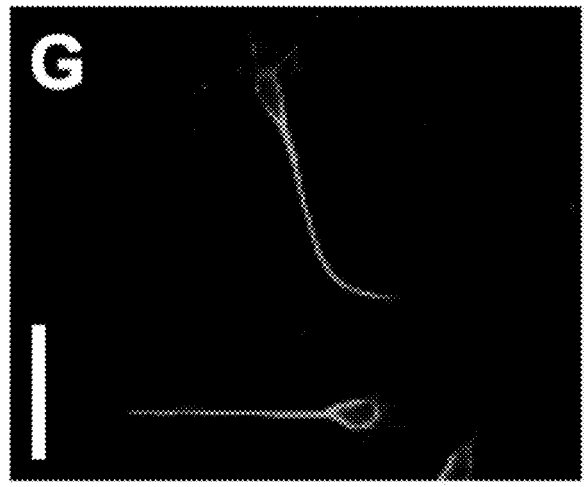
FIG. 22F  FIG. 22G
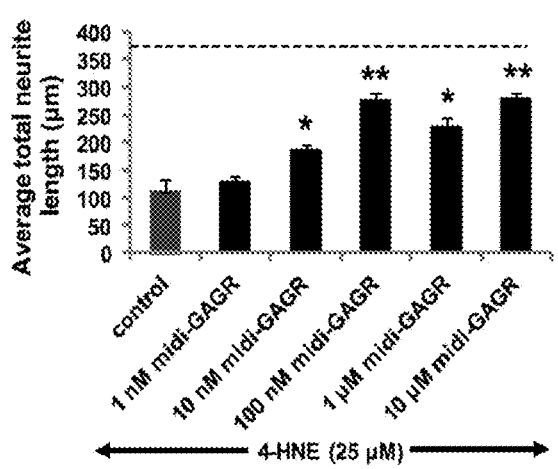
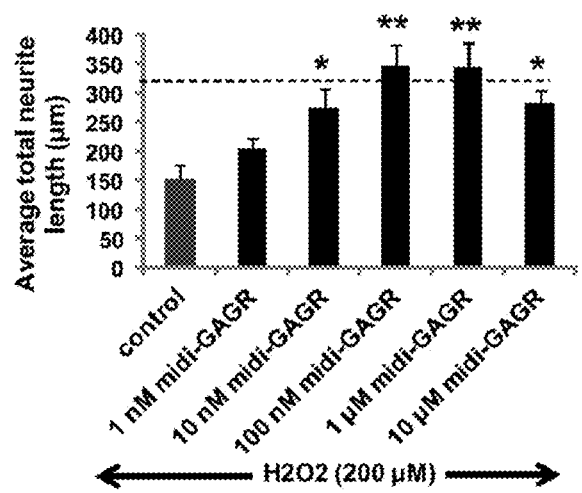
FIG. 22H  FIG. 22I

FIG.23A
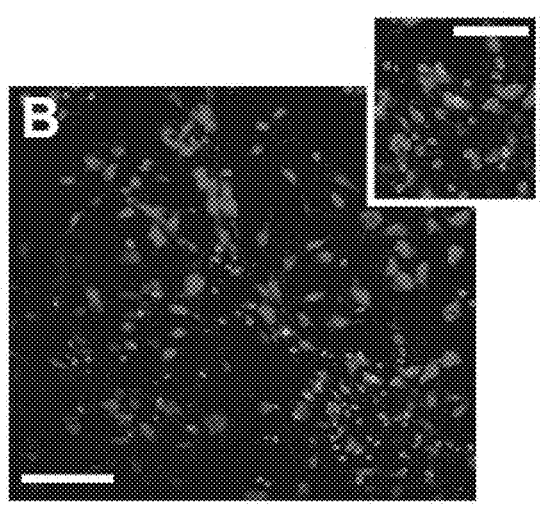 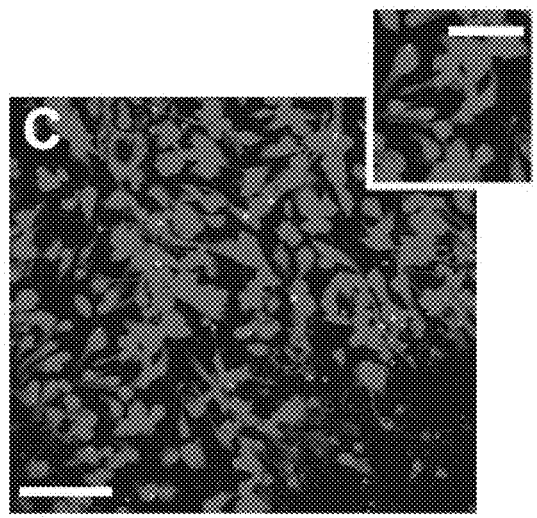
FIG. 23B  FIG. 23C

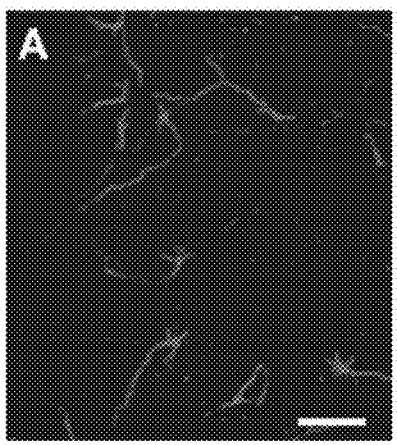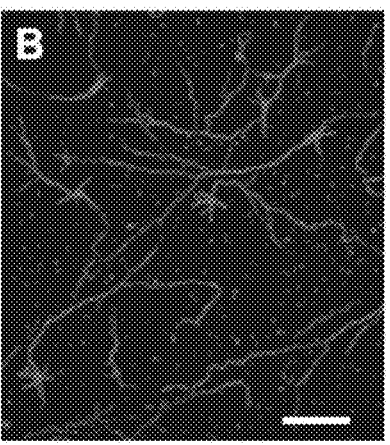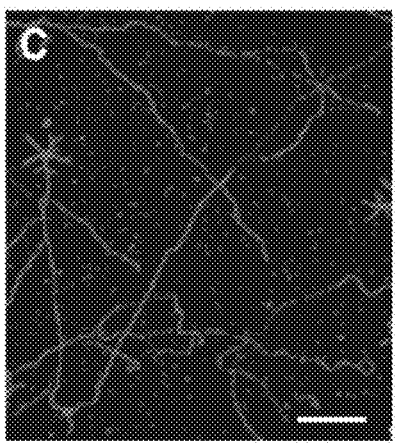
FIG. 27A  FIG. 27B  FIG. 27C
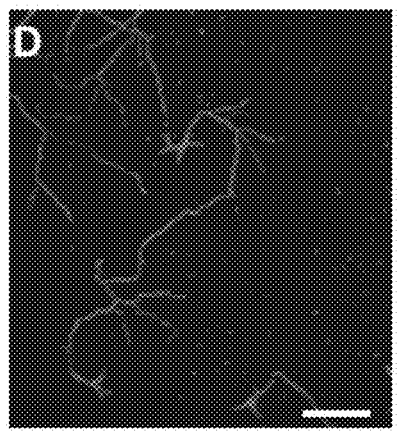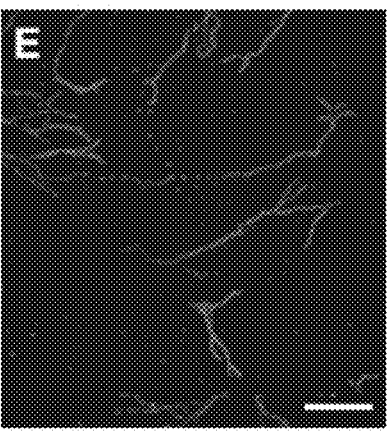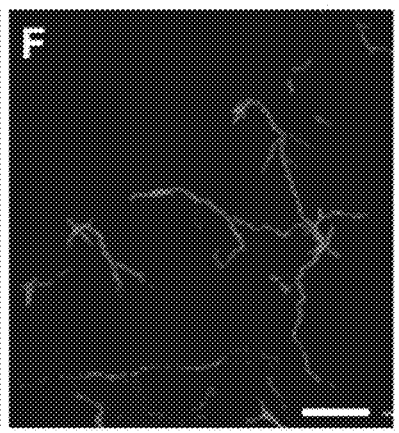
FIG. 27D  FIG. 27E  FIG. 27F
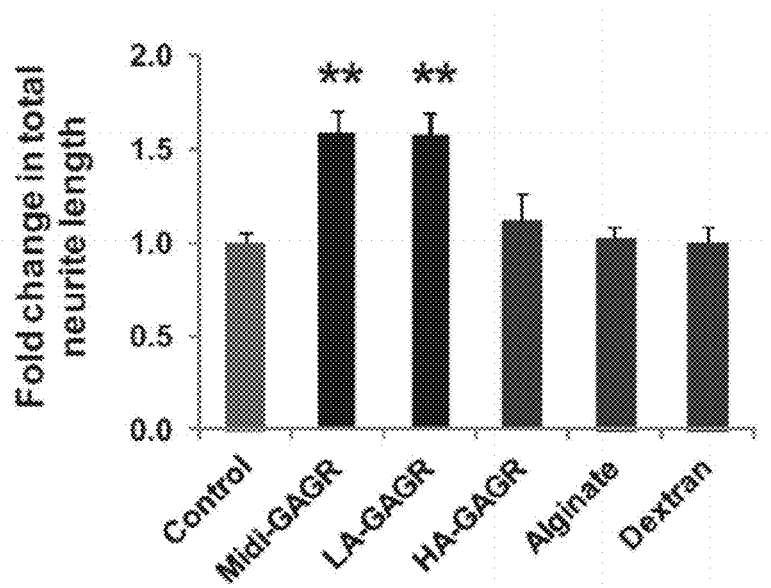
FIG. 27G

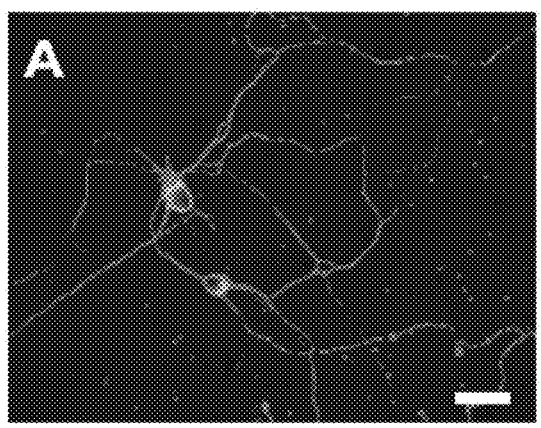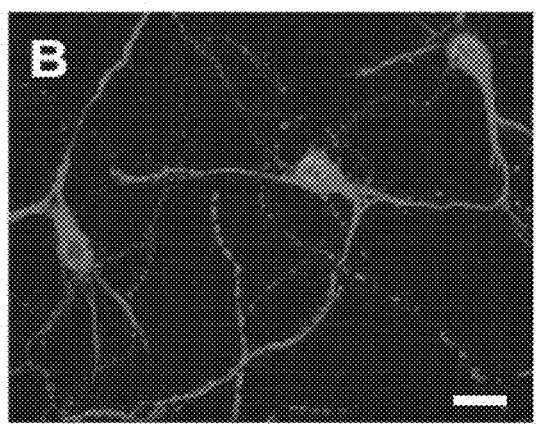
FIG. 28A    FIG. 28B
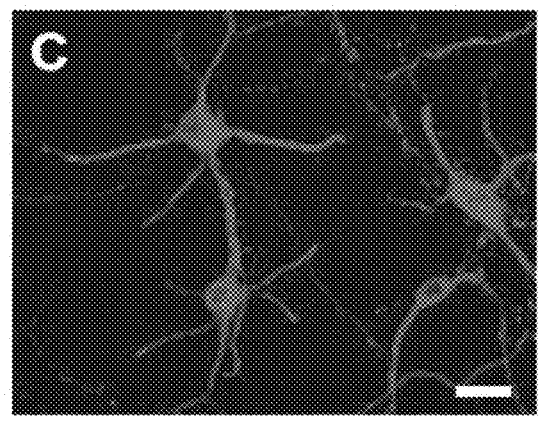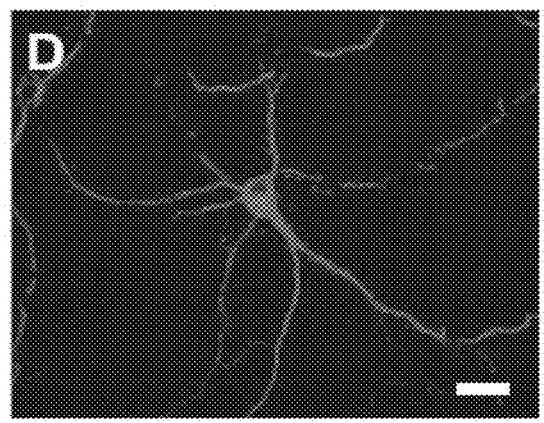
FIG. 28C    FIG. 28D
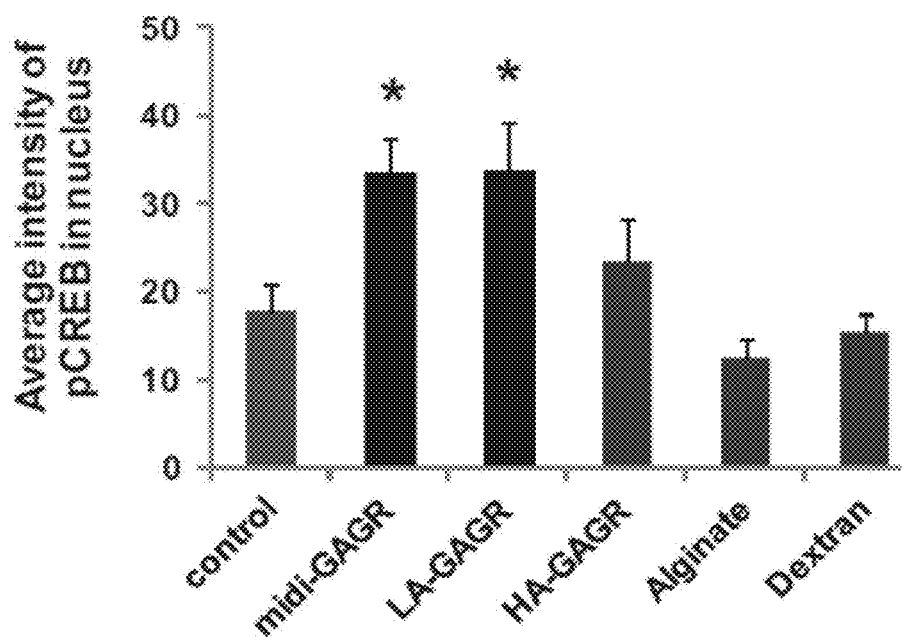
FIG. 28E

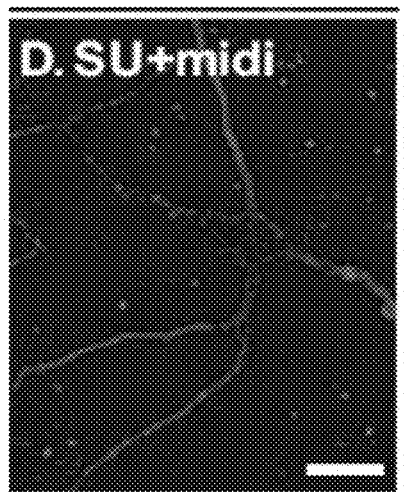
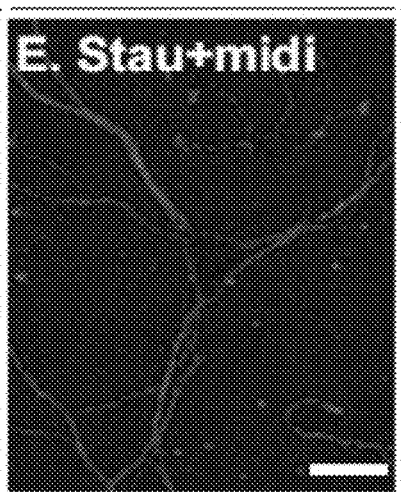
FIG. 30D    FIG. 30E
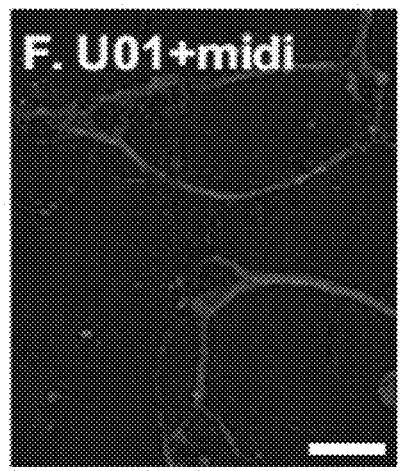
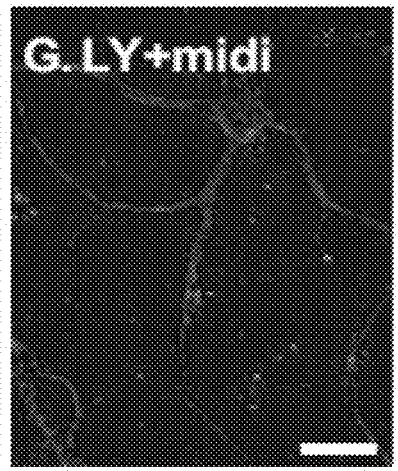
FIG. 30F    FIG. 30G
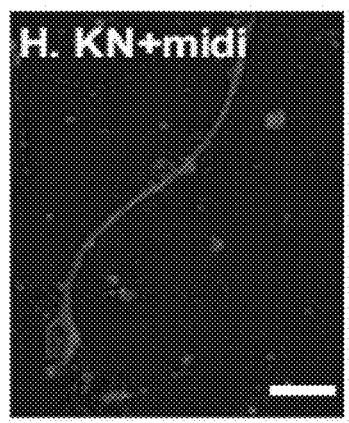
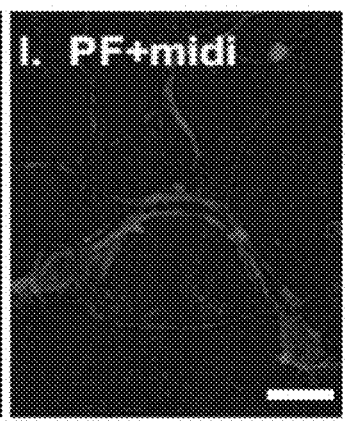
FIG. 30H    FIG. 30I

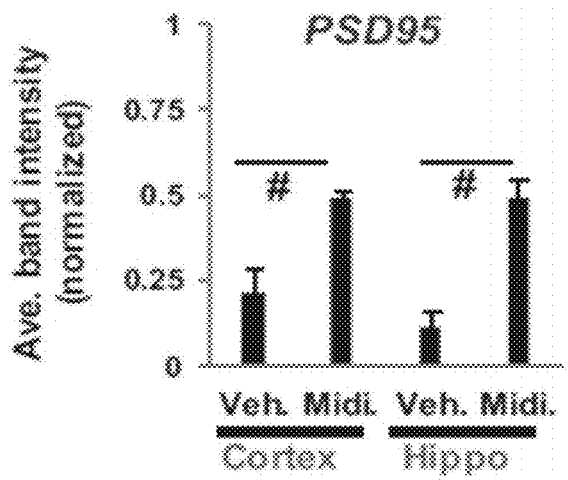
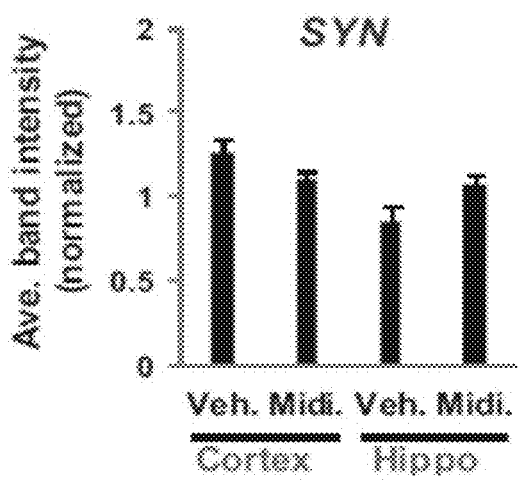
FIG. 31D  FIG. 31E
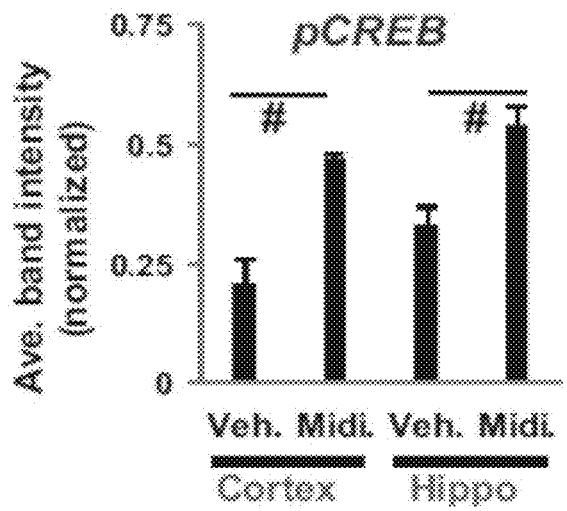
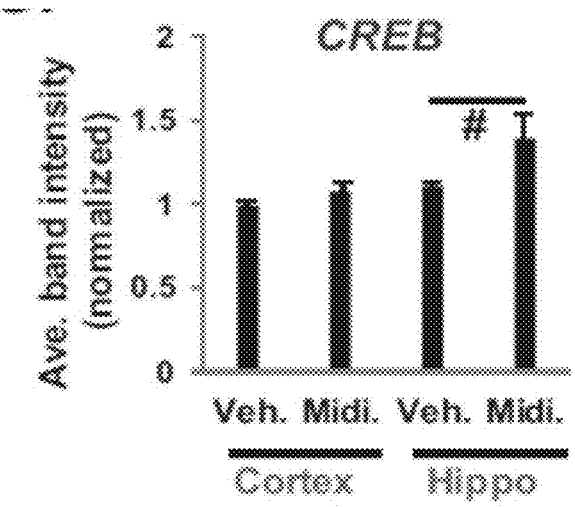
FIG. 31F  FIG. 31G
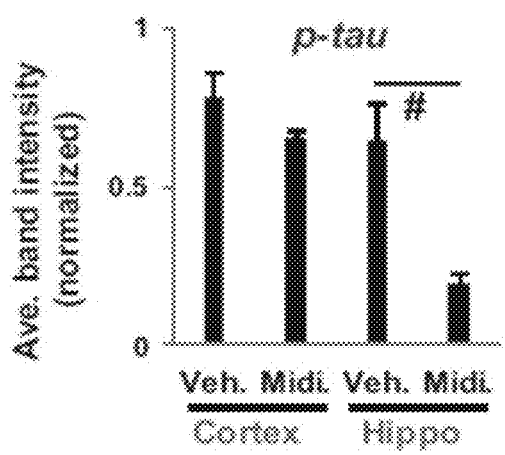
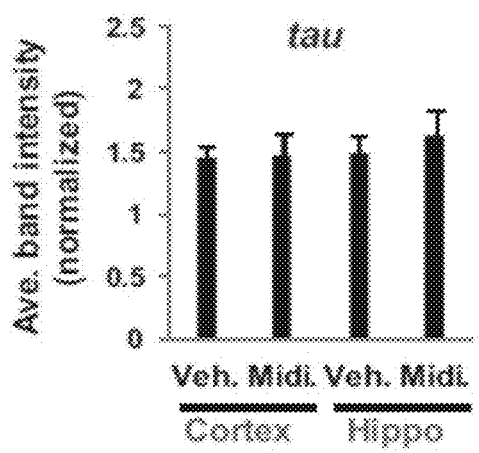
FIG. 31H  FIG. 31I

|  | Fluorescence (RFU) | Absorbance [$A_{490}$] |
| --- | --- | --- |
| Unwashed | 7493 ± 265.3 | 0.269 ± 0.014 |
| 75% EtOH Washes | 4910 ± 376.3 | 0.219 ± 0.023 |

| | 1st: TCA Precipitation | 2nd: Ethanol Precipitation |
|---|---|---|
| Supernatant | 201.353 ± 40.44 | 37.068 ± 1.2 |
| Pellet | 42.872 ± 7.07 | 197.081 ± 43.18 |

COLLAGEN ENHANCING AGENT MADE FROM LOW ACYL GELLAN GUM, METHODS OF MAKING AND METHODS OF USING THE SAME

CROSS-REFERENCE TO RELATED CASES

This is a bypass continuation-in-part application of international application PCT/US16/17734, filed under the authority of the Patent Cooperation Treaty on Feb. 12, 2016, published; which claims the priority to U.S. Provisional Application No. 62/115,777, filed under 35 U.S.C. § 111(b) on Feb. 13, 2015; to U.S. Provisional Application No. 62/115,781, filed under 35 U.S.C. § 111(b) on Feb. 13, 2015; and to U.S. Provisional Application No. 62/115,786, filed under 35 U.S.C. § 111(b) on Feb. 13, 2015. The entire disclosures of all the aforementioned applications are expressly incorporated herein by reference for all purposes.

BACKGROUND OF THE INVENTION

Alzheimer's disease (AD) is a progressive degenerative disorder of the brain that begins with memory impairment and eventually progresses to dementia, physical impairment, and death. Approximately 4.5 million people in the United States suffer from AD, costing over $100 billion annually. During AD development, oxidative stress significantly increases inside of the brain, resulting in production of excessive free reactive radicals, such as reactive oxygen intermediates (ROI: superoxide anion and hydrogen peroxide) and 4-hydroxynonenal (4-HNE), a lipid peroxide. Amyloid β peptide ($A\beta_{42}$) also increases oxidative stress by damaging the mitochondria, resulting in generation of free radicals. Cortical and hippocampal neurons exposed to $A\beta_{42}$ begin neurite atrophy and then undergo apoptosis.

Parkinson's disease affects nearly 1 million Americans and is the second leading neurodegenerative disease in the United States. Parkinson's disease is a result of chronic progressive degeneration of neurons, the cause of which has not yet completely been clarified. While the primary cause of Parkinson's disease is not known, it is characterized by the preferential loss of dopaminergic neurons in the substantia nigra and subsequent loss of dopamine in the striatum. Loss of dopamine in the striatum results in resting tremor, bradykinesia, rigidity, and postural instability.

Remedies are needed that not only influence the dopaminergic transmission and alleviate the symptoms of the Parkinson's disease in advanced stages, but also reverse, prevent, or at least significantly delay the dopaminergic neuron extinction in the early, to a great extent motor-asymptomatic, Parkinson stages. However, the short half-life and blood-brain barrier (BBB) impermeability of protein-based neurotrophic factors limit their clinical uses. Thus, there is a need for an alternative neurotrophic agent that overcomes those shortcomings for better treatment of PD.

SUMMARY OF THE INVENTION

In a first aspect, there is provided herein a method of treating a degenerative neurological disorder comprising administering to a subject in need of such treatment, an effective amount of low acyl gellan gum (LA-GAGR) or its cleavage product, thereby treating the degenerative neurological disorder.

In certain embodiments, the degenerative neurological disorder is selected from the group consisting of Alzheimer's disease, Parkinson's disease, multiple sclerosis, amyotrophic lateral sclerosis, spinal cord injury, and brain trauma. In certain embodiments, the subject is a human.

In certain embodiments, the effective amount of LA-GAGR or its cleavage product is administered in combination with a pharmaceutically acceptable carrier thereof.

In another aspect, there is provided herein a method of enhancing osteogenesis by adult mesenchymal stem cells comprising contacting one or more adult mesenchymal stem cells with an effective amount of LA-GAGR or its cleavage product, thereby enhancing osteogenesis by adult mesenchymal stem cells.

In another aspect, there is provided herein a method of enhancing osteogenesis comprising administering to a subject in need thereof an effective amount of LA-GAGR or its cleavage product, thereby enhancing osteogenesis. In certain embodiments, the subject has osteoarthritis, osteoporosis, a metabolic bone disorder, and/or a broken and/or fractured bone. In certain embodiments, the subject is human.

In certain embodiments, the LA-GAGR cleavage product is produced by enzymatic digestion of LA-GAGR by α(1→3)-glucosidase.

In certain embodiments, the enzymatic digestion of LA-GAGR by α(1→3)-glucosidase occurs at approximately 37° C. for about 48 hours.

In certain embodiments, the LA-GAGR cleavage product is midi-LA-GAGR, wherein midi-GAGR has a molecular weight of about 4,775 g/mol.

In certain embodiments, the enzymatic digestion of LA-GAGR by α(1→3)-glucosidase occurs at approximately 37° C. for ≥72 hours.

In certain embodiments, the LA-GAGR cleavage product is mini-GAGR, wherein mini-GAGR has a molecular weight of about 718 g/mol.

In certain embodiments, the enzymatic digestion of LA-GAGR by α(1→3)-glucosidase occurs in acetate buffer having a concentration of about 0.1 M.

In certain embodiments, the acetate buffer has a pH of about 5.

In certain embodiments, the acetate buffer comprises 1% salicin.

In another aspect, there is provided herein a composition comprising a low acyl gellan gum (LA-GAGR) cleavage product, wherein the LA-GAGR cleavage product is produced by enzymatic digestion of LA-GAGR by α(1→3)-glucosidase.

In certain embodiments, the composition further comprises a pharmaceutically acceptable carrier for the LA-GAGR cleavage product.

In certain embodiments, the composition comprises 10-95% midi-GAGR, mini-GAGR, or a mixture thereof, a pharmaceutically acceptable carrier thereof, and wherein the composition is formulated for oral administration.

In certain embodiments, the composition comprises 25-75% midi-GAGR, mini-GAGR, or a mixture thereof.

In certain embodiments, the pharmaceutical formulation comprises 0.0001-20% by weight midi-GAGR, mini-GAGR or a mixture thereof, and wherein the composition is formulated for aerosol (inhalational) administration.

In certain embodiments, the composition comprises 1-10% by weight midi-GAGR, mini-GAGR or a mixture thereof.

In another aspect, there is provided herein a method of treating osteoporosis comprising administering to a subject in need thereof an effective amount of midi-GAGR and/or mini-GAGR, thereby treating osteoporosis. In certain embodiments, the subject is human.

In another aspect, provided herein is a method of enhancing wound healing, the method comprising applying a composition comprising an effective amount of LA-GAGR or its cleavage product(s) to a wound of a subject to enhance healing of the wound. In certain embodiments, wherein the LA-GAGR cleavage product comprises midi-GAGR or mini-GAGR. In certain embodiments, the LA-GAGR cleavage product is produced by enzymatic digestion of LA-GAGR by $\alpha(1\rightarrow3)$-glucosidase. In particular embodiments, the enzymatic digestion of LA-GAGR by $\alpha(1\rightarrow3)$-glucosidase occurs at approximately 37° C. for about 48 hours. In particular embodiments, the LA-GAGR cleavage product is midi-LA-GAGR, having a molecular weight of about 4,775 g/mol. In particular embodiments, the enzymatic digestion of LA-GAGR by $\alpha(1\rightarrow3)$-glucosidase occurs at approximately 37° C. for ≥72 hours. In particular embodiments, the LA-GAGR cleavage product is mini-LA-GAGR, having a molecular weight of about 718 g/mol. In certain embodiments, the composition comprises a gel. In particular embodiments, the gel composition comprises the LA-GAGR or LA-GAGR cleavage product bound to a gelling component comprising chitosan, alginate, and/or hyaluronic acid.

In another aspect, provided herein is a method of enhancing collagen production or glycosaminoglycan (GAG) production in cells, the method comprising administering an effective amount of a low acyl gellan gum (LA-GAGR) cleavage product to cells, and enhancing collagen production or GAG production in the cells, wherein the LA-GAGR cleavage product comprises midi-GAGR or mini-GAGR. In certain embodiments, the LA-GAGR cleavage product is produced by enzymatic digestion of LA-GAGR by $\alpha(1\rightarrow3)$-glucosidase. In particular embodiments, the enzymatic digestion of LA-GAGR by $\alpha(1\rightarrow3)$-glucosidase occurs at approximately 37° C. for about 48 hours. In particular embodiments, the LA-GAGR cleavage product is midi-LA-GAGR, having a molecular weight of about 4,775 g/mol. In particular embodiments, the enzymatic digestion of LA-GAGR by $\alpha(1\rightarrow3)$-glucosidase occurs at approximately 37° C. for ≥72 hours. In particular embodiments, the LA-GAGR cleavage product is mini-LA-GAGR, having a molecular weight of about 718 g/mol. In certain embodiments, the LA-GAGR cleavage product is administered in a gel composition. In particular embodiments, the gel composition comprises the LA-GAGR cleavage product bound to a gelling component comprising chitosan, alginate, and/or hyaluronic acid. In certain embodiments, the cells comprise cartilage cells.

In another aspect, provided herein is a method of enhancing blood vessel formation, the method comprising administering an effective amount of LA-GAGR or its cleavage product to vein endothelial cells, and enhancing blood vessel formation in the vein endothelial cells, wherein the LA-GAGR cleavage product comprises midi-GAGR or mini-GAGR. In certain embodiments, the LA-GAGR cleavage product is produced by enzymatic digestion of LA-GAGR by $\alpha(1\rightarrow3)$-glucosidase. In particular embodiments, the enzymatic digestion of LA-GAGR by $\alpha(1\rightarrow3)$-glucosidase occurs at approximately 37° C. for about 48 hours. In particular embodiments, the LA-GAGR cleavage product is midi-LA-GAGR, having a molecular weight of about 4,775 g/mol. In particular embodiments, the enzymatic digestion of LA-GAGR by $\alpha(1\rightarrow3)$-glucosidase occurs at approximately 37° C. for ≥72 hours. In particular embodiments, the LA-GAGR cleavage product is mini-LA-GAGR, having a molecular weight of about 718 g/mol. In certain embodiments, the LA-GAGR cleavage product is administered in a gel composition. In particular embodiments, the gel composition comprises the LA-GAGR cleavage product bound to a gelling component comprising chitosan, alginate, and/or hyaluronic acid.

In another aspect, provided herein is a topical composition comprising a polysaccharide component comprising LA-GAGR, a cleavage product of LA-GAGR, or combinations thereof; a gelling component bound to the polysaccharide component, wherein the gelling component comprises one or more of chitosan, alginate, or hyaluronic acid; and, optionally, one or more pharmaceutically acceptable excipients, diluents, or adjuvants, wherein the topical composition is a gel. In certain embodiments, the LA-GAGR cleavage product is produced by enzymatic digestion of LA-GAGR by $\alpha(1\rightarrow3)$-glucosidase, and comprises midi-GAGR or midi-GAGR. In certain embodiments, the topical composition is configured for controlled release of the polysaccharide component.

BRIEF DESCRIPTION OF THE DRAWINGS

FIG. 11D: pretreated with midi-GAGR) for 1 day. Neurons were processed for immunocytochemistry using antibody to synaptophysin (green) and phalloidin (actin: red) (scale bars=75 µm).

FIGS. 22A-22I: Midi-GAGR reverses neurite atrophy caused by 4HNE and $H_2O_2$. Differentiated N2A cells were treated with different concentrations of 4HNE (0, 1, 5, 10, and 25 μM) for 48 h or $H_2O_2$ (0, 1, 10, 50, 100, and 200 μM) for 24 h and immunostained with α-tubulin antibody. The representative images of N2A cells treated with $H_2O$ (vehicle) (FIG. 22A), 25 μM 4HNE (FIG. 22B), or 200 μM $H_2O_2$ (FIG. 22C). Scale bar=75 μm. Bar graphs represent the average total neurite lengths of N2A cells in response to different concentrations of either 4HNE (FIG. 22D) or $H_2O_2$ (FIG. 22E). *, $p<0.05$ and **, $p<0.001$ compared to control. (FIG. 22F-FIG. 22I.) Differentiated N2A cells were pretreated with different concentrations (0, 0.001, 0.01, 0.1, 1, and 10 μM) of midi-GAGR for 24 h, followed by incubation with either 25 μM 4HNE for 48 h or 200 μM $H_2O_2$ for 24 h and then immunostained with anti-α-tubulin antibody. The representative images of N2A cells pretreated with 1 μM midi-GAGR and then incubated with either 25 μM 4HNE (FIG. 22F) or 200 μM $H_2O_2$ (FIG. 22G). Scale bar=75 μm. Bar graphs show the average total neurite lengths of N2A cells pre-treated with different concentrations of midi-GAGR followed by treatment with 25 μM 4HNE (FIG. 22H) or 200 μM $H_2O_2$ (FIG. 22I). Dotted lines correspond to the average total neurite lengths of N2A cells without any treatment. Data represent mean±SEM of, at least, 40 cells/group from two independent experiments. *, $p<0.05$ and **, $p<0.001$ compared to 4HNE alone.

FIGS. 23A-23G: Pre-treatment with midi-GAGR significantly reduces the apoptosis of rodent cortical neurons caused by 4HNE, $H_2O_2$, and amyloid β peptide. Mouse cortical neurons at DIV5 were pre-treated with $H_2O$ (vehicle), 1 μM midi-GAGR, 0.1 μM LA-GAGR, 0.01 μM HA-GAGR, 1 μM alginate, or 1 μM dextran followed by incubation with vehicle, 10 μM 4HNE, or 50 μM $H_2O_2$ for 24 h or 2 μM $Aβ_{42}$ for 48 h. After the treatment, neurons were processed for live/dead assay using calcein AM and ethidium homodimer-I. The representative images of $H_2O$ (FIG. 23A), 4HNE alone (FIG. 23B), 4HNE+midi-GAGR (FIG. 23C), $H_2O_2$ alone (FIG. 23D), $H_2O_2$+midi-GAGR (FIG. 23E), $Aβ_{42}$ alone (FIG. 23F), and $Aβ_{42}$+midi-GAGR (FIG. 23G). Live cells were labeled as green and dead cells as red. Scale bar=100 μm. Insets show the magnified images of individual neurons. Inset scale bar=50 μm.

(FIG. 25A.) Rat cortical neurons (E17) at DIV5 were co-treated with either 10 μM 4HNE (for 24 h) or 2 μM $Aβ_{42}$ (for 48 h) and either water or 1 μM midi-GAGR. After the treatment, neurons were processed for live/dead assay using calcein AM and ethidium homodimer-I. Live and dead cells were imaged using a fluorescence microscope. The numbers of live and dead cells were counted using Metamorph software. Bar graphs show the percents of dead neurons after co-treatment with either 4HNE or $Aβ_{42}$ plus/minus midi-GAGR. Data represent mean±SEM of three independent experiments. *, $p<0.05$. (FIG. 25B.) The co-cultures of rat cortical neurons and microglia cells were treated with 2 μM $Aβ_{42}$ plus/minus 1 μM midi-GAGR. After 48 h, transwell filters containing microglial cells were removed and neurons in bottom wells were processed for live/dead assay. Live and dead cells were imaged using a fluorescence microscope. The numbers of live and dead neurons were counted using Metamorph software. Bar graphs show the percent of dead neurons. Data represent mean±SEM of three independent experiments. *, $p<0.05$.

FIGS. 27A-27G: Midi-GAGR enhances neuritogenesis in mouse cortical neurons. Mouse cortical neurons (E17, DIV4) were treated with $H_2O$ (vehicle) (FIG. 27A), 1 μM midi-GAGR (FIG. 27B), 0.1 μM LA-GAGR (FIG. 27C), 0.01 μM HA-GAGR (FIG. 27D), 1 μM alginate (FIG. 27E), or 1 μM dextran (FIG. 27F) for 48 h and immunostained with anti-α-tubulin antibody. Scale bar=100 μm. (FIG. 27G.) Bar graphs show average fold changes in the total neurite length of mouse cortical neurons in response to different polysaccharides (mean±SEM of, at least, three independent experiments). **, $p<0.01$ compared to control.

FIGS. 28A-28F: Midi-GAGR activates CREB, a neurotrophic transcriptional factor. Mouse cortical neurons (DIV4) were treated with $H_2O$ (vehicle), 1 μM midi-GAGR, 0.1 μM LA-GAGR, 0.01 μM HA GAGR, 1 μM alginate, or 1 μM dextran for 48 h and immunostained with DAPI (not shown) and the antibodies to α-tubulin and pCREB. The representative images of neurons treated with $H_2O$ (FIG. 28A), midi-GAGR (FIG. 28B), alginate (FIG. 28C) or dextran (FIG. 28D), followed by staining with α-tubulin (green) and pCREB (red). Scale bar=30 μm. Bar graphs show the average intensities of pCREB after different treatments (n=90 neurons, mean±SEM of, at least, three independent experiments). *, $p<0.05$ compared to control. (FIG. 28E.) The cytosols extracted from neurons treated with $H_2O$ (vehicle), 1 μM midi-GAGR, 0.1 μM LA-GAGR, 0.01 μM HA GAGR, 1 μM alginate, or 1 μM dextran for 48 h were used for immunoblotting using the antibodies to pCREB and CREB (neurons extracted from sixteen E17 mouse embryos, n=2 experiments). (FIG. 28F.)

(FIG. 29A.) Brain tissue lysates were processed for immunoblotting using the antibody to NF200 (upper panel), GAP-43 (middle panel), or GAPDH (lower panel). 'C' is control and 'M' is midi-GAGR. The band densities of NF200 and GAP-43 were measured using image J software and normalized to those of GAPDH. Bar graphs show fold changes in the level of NF200 (FIG. 29B) and GAP-43 (FIG. 29C) in the different parts of brains at given time points. Data represents mean±SEM (n=4 animals/group). *, $p<0.05$.

FIGS. 30A-30K: Midi-GAGR binds to FGFR1 and uses FGFR1 signaling pathway to activate CREB and protect neurons from the death caused by oxidative insult. FIG. 30A: Midi-GAGR- or dextran-conjugated epoxy sepharose beads were mixed with synaptosomal plasma membrane proteins in 0.5% Igepal CA-630 PMEE buffer to pull down midi-GAGR-interacting FGFR1. Precipitated FGFR1 was detected by immunoblotting (n=2, four rat brains). FIGS. 30B-J: Mouse cortical neurons (DIV4) were pre-treated with $H_2O$ (vehicle, FIGS. 30B-30C) or the inhibitors of FGFR1 (SU5402 [SU], 4 μM, FIG. 30D, PKC (staurosporine [Stau], 3 nM, FIG. 30E), MEK (U0126 [U01], 10 μM, FIG. 30F), PI3K (LY294002 [LY], 20 μM, FIG. 30G), CaMKII (KN-62 [KN], 10 μM, FIG. 30H), or FAK (PF-573228 [PF], 1 μM, FIG. 30I) for 6 h and then with mock (FIG. 30B) or 1 μM midi-GAGR (+midi, FIGS. 30C-30I) for 48 h. Neurons were then immunostained with the antibodies to α-tubulin (red) and p-CREB (green). Scale bar=100 μm. (FIG. 30J.) Bar graphs show the average intensities of pCREB after different treatments (n=60 neurons, mean±SEM). *, $p<0.01$ and #, $p<0.05$ compared to control. (FIG. 30K.) Rat cortical neurons (E17, DIV6) were treated for 6 h with FGFR1 inhibitor (SU5402, 4 μM) and treated with 10 μM 4HNE and either vehicle or 1 μM midi-GAGR for 24 h prior to cell viability/cytotoxicity assay. As controls, neurons were treated with 4HNE, 4-HNE plus midi-GAGR, SU5402, midi-GAGR, or SU5402 plus midi-GAGR. Live and dead cells were imaged using a fluorescence microscope. The numbers of live and dead neurons were counted using Metamorph software. Bar graphs show the percent of dead neurons. Data represent mean±SEM of three independent experiments. For each experiment, at least, 200 cells per group were counted. *, $p<0.05$ (n.s.: not significant)

FIGS. 31A-31I: Intranasally administered midi-GAGR increased neuronal activity markers and decreased hyperphosphorylated tau in 3×Tg-AD mice. FIG. 31A: 12-week-old 3×Tg-AD mice were intranasally administered with 40 μL (20 μL/nostril) of either sterile $H_2O$ (Veh.) or 7.4 mM midi-GAGR (midi) every day for 14 days and processed to obtain the cortex and hippocampus (Hippo). The tissues were homogenized to extract proteins for immunoblotting using the antibodies to NF200, GAP-43, PSD95, synaptophysin, pCREB, CREB, p-tau (AT8), tau, and GAPDH. (FIGS. 31B-31I) The densities of protein bands were measured using Image J and normalized to that of the loading control, GAPDH. Normalized values were used to calculate the average normalized band densities of NF200 (FIG. 31B), GAP-43 (FIG. 31C), PSD95 (FIG. 31D), synaptophysin (SYN, FIG. 31E), pCREB (FIG. 31F), total CREB (FIG. 31G), p-tau (FIG. 31H), and total tau (FIG. 31I). Data represent mean±SEM of three independent animals. #, $p<0.01$, *, $p<0.05$.

(FIG. 34A.) On day 7, cytosols were obtained in 1% NP-40 PMEE buffer from cartilage cells and used for immunoblotting using antibodies to type II collagen and beta-actin (n=2). (FIG. 34B.)

DETAILED DESCRIPTION OF THE INVENTION

Throughout this disclosure, various publications, patents and published patent specifications are referenced. The disclosures of these publications, patents and published patent specifications are hereby incorporated by reference into the present disclosure to more fully describe the state of the art to which this invention pertains.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Definitions

Figure 1A:
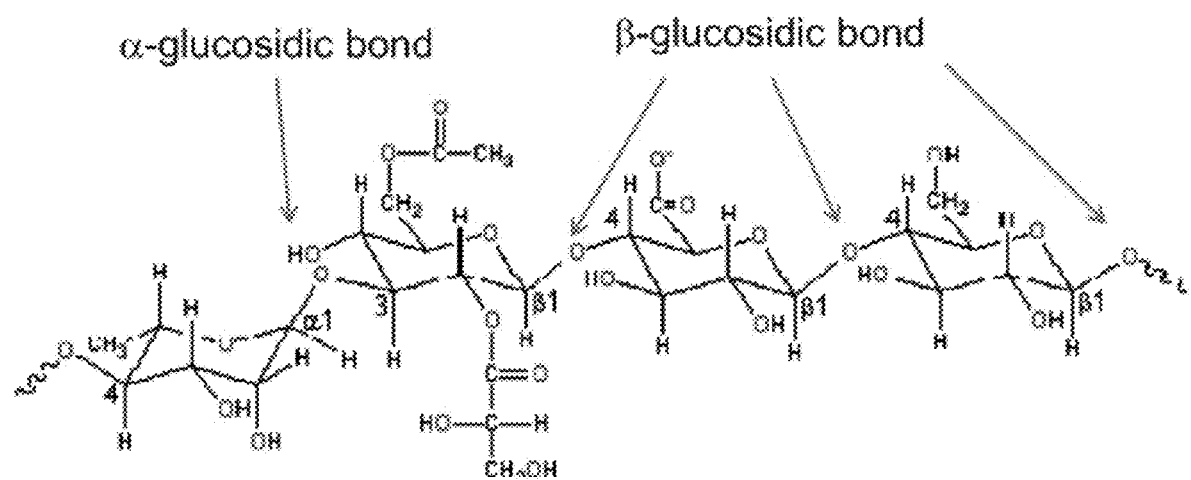
FIG. 1A: Low acyl gellan gum (LA-GAGR). Drawing of the chemical structure of LA-GAGR ([D-Glc($\beta1\rightarrow4$)D-GlcA($\beta1\rightarrow4$)D-Glc($\beta1\rightarrow4$)L-Rha($\alpha1\rightarrow3$]n). Arrows point to either $\alpha$- or $\beta$-glucosidic bonds. Enzymatic decomposition of LA-GAGR by $\alpha(1\rightarrow3)$-glucosidase results in cleavage products having approximate molecular weights of either 4,755 g/mol (48 hour digestion) or 718 g/mol (72 hour digestion).
Figure 1B:
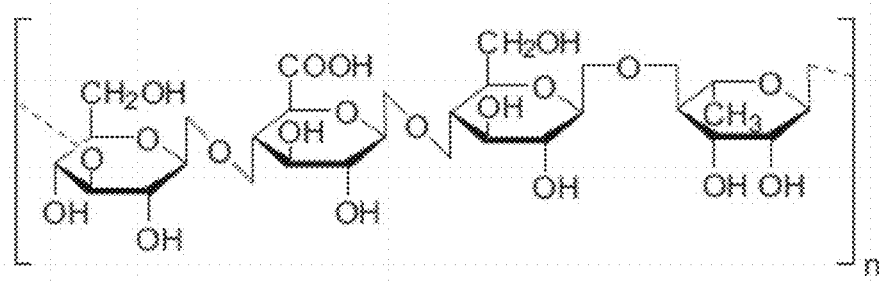
FIG. 1B: Repeating tetrasaccharide unit of low acyl gellan gum. Low acyl gellan gum consists of the repeating tetrasaccharide unit ([D-Glc($\beta1\rightarrow4$)D-GlcA($\beta1\rightarrow4$)D-Glc($\beta1\rightarrow4$)L-Rha($\alpha1\rightarrow3$)]$_n$).

As used herein, the term "LA-GAGR" refers to low acyl gellan gum. LA-GAGR is a polysaccharide based on a tetrasaccharide repeating unit consisting of glucose derivatives such as glucuronic acid, mannose, and rhamnose connected by (1-3)-$\alpha$ and (1-4)-$\beta$, and has an average molecular weight of 99,600 g/mol (LA-GAGR: [D-Glc($\beta$1→4)D-GlcA($\beta$1→4)D-Glc($\beta$1→4)L-Rha($\alpha$1→3)]n) (FIG. 1). The molecular weights of the repeating units are reported to be 700-1,000 g/mol, depending on their functional groups and branches. Gellan gum is produced by fermentation of calcium hydrates in *Sphingomonas elodea* monocultures extracted from natural resources. Primarily used as a food additive, LA-GAGR may be found in food products such as baked goods, cake icings, various sweets, jellies and spreads, jams, puddings, sauces, dairy products, and microwave-ready foods. LA-GAGR can also be used in cosmetic and hygiene products such as makeup, facial masks, creams, and lotions. In pharmaceuticals, LA-GAGR is used to make tablets that are easy to swallow, as well as to adjust the rate of release of medicinal compounds in the body.

As used herein, "GAGR" generally refers to gellan gum which has a molecular weight greater than that of native gellan gum. The term "native gellan gum" generally refers to a gellan gum that has not been modified by physical or chemical means.

As used herein, the term "neurodegenerative disorders" refers to any central nervous system (CNS) or peripheral nervous system (PNS) disease that is associated with neuronal or glial cell defects including but not limited to neuronal loss, neuronal degeneration, neuronal demyelination, gliosis (i.e., astrogliosis), or neuronal or extra-neuronal accumulation of aberrant proteins or toxins (e.g., $\beta$-amyloid, or $\alpha$-synuciein). The neurological disorder can be chronic or acute. Non-limiting examples of various chronic and acute neurological diseases include Parkinson's disease, Alzheimer's disease, amyotrophic lateral sclerosis, myasthenia gravis, multiple sclerosis, microbial infections, stroke, Pick's disease, dementia with Lewy bodies, Huntington disease, chromosome 13 dementias, Down's syndrome, cerebrovascular disease, Rasmussen's encephalitis, viral meningitis, NPSLE, amyotrophic lateral sclerosis, Creutzfeldt-Jacob disease, Gerstrnann-Straussler-Scheinker disease, transmissible spongiform encephalopathies, ischemic reperfusion damage (e.g., stroke), brain trauma, spinal cord injury, microbial infection, chronic fatigue syndrome, Mild Cognitive Impairment, movement disorders (including ataxia, cerebral palsy, choreoathetosis, dystonia, Tourette's syndrome, kernicterus), tremor disorders, leukodystrophies (including adrenoleukodystrophy, metachromatic leukodystrophy, Canavan disease, Alexander disease, Pelizaeus-Merzbacher disease); neuronal ceroid lipofucsinoses, ataxia telangectasia, and Rett Syndrome.

As used herein, the term "neuroprotective" refers to the relative preservation of neuronal structure and/or function. In a case of ongoing neurodegenerative insult, the relative preservation of neuronal integrity implies a reduction in the rate of neuronal loss over time. Neuroprotection aims to prevent or slow disease or injury progression and secondary injuries by halting or at least slowing the loss of neurons.

As used herein, the term "bone disorders" refers to a condition characterized by altered bone metabolism. Non-limiting examples include osteoporosis, including post-menopausal osteoporosis, osteopenia, Paget's disease, osteolytic metastasis in cancer patients, osteodistrophy in liver disease and the altered bone metabolism caused by renal failure or haemodialysis, osteogenesis imperfecta, bone fracture, bone surgery, aging, pregnancy, and malnutrition. "Osteogenesis" refers to the formation and development of bone.

As used herein, the term "effective amount" refers to an amount of an agent that is sufficient to effect a therapeutically significant neuroprotective effect, a therapeutically significant neurotrophic effect, or alternatively, a therapeutically significant osteogenic effect, in a subject diagnosed with a neurodegenerative disorder or bone disorder, respectively. The therapeutically effective amounts to be administered will depend on the severity of the condition and individual subject parameters including age, physical condition, size, weight, and concurrent treatment. In certain embodiments, a maximum dose can be used, that is, the highest safe dose according to sound medical judgment. However, a lower dose or tolerable dose may be administered for medical reasons, psychological reasons, or for virtually any other reason.

The actual dosage amount of a composition administered to the subject, such as a human subject, can be determined by physical and physiological factors such as body weight, severity of condition, the type of disease being treated, previous or concurrent therapeutic interventions, idiopathy of the subject and on the route of administration. The practitioner responsible for administration will, in any event, determine the concentration of active ingredient(s) in a composition and appropriate dose(s) for the individual subject.

As used herein, the term "therapeutic agent" refers to any biologic agent, molecule, compound, and/or substance that is used for the purpose of treating and/or managing a disease or disorder. As used herein, "agent" refers to any biologic agent, molecule, compound, methodology, and/or substance for use in the prevention, treatment, management, and/or diagnosis of a disease or disorder. As used herein, the terms "prevent," "preventing," and "prevention" in the context of the administration of a therapy to a subject refer to the prevention or inhibition of the recurrence, onset, and/or development of a disease or condition, or a symptom thereof, in a subject resulting from the administration of a therapy (e.g., a prophylactic or therapeutic agent), or a combination of therapies (e.g., a combination of prophylactic or therapeutic agents).

As used herein, the terms "treat," "treatment," and "treating" in the context of the administration of a therapeutic agent to a subject refer to the reduction or inhibition of the progression and/or duration of a disease or condition, the reduction or amelioration of the severity of a disease or condition, and/or the amelioration of one or more symptoms thereof resulting from the administration of one or more therapies.

The terms "subject," "individual," and "patient" are defined herein to include animals such as mammals, including but not limited to, primates, cows, sheep, goats, horses, dogs, cats, rabbits, guinea pigs, rats, mice or other bovine, ovine, equine, canine, feline, rodent, or murine species. In one embodiment, the subject is a mammal (e.g., a human) afflicted with a neurodegenerative disorder. In another embodiment, the subject is a mammal (e.g., a human) afflicted with a bone disorder.

The term "gel" refers to a jelly-like material composed of a cross-linked system.

Pharmaceutical compositions are characterized as being sterile and pyrogen-free. As used herein, "pharmaceutical compositions" include compositions for human and veterinary use. Methods for preparing pharmaceutical compositions of the invention are within the skill in the art, for example, as described in *Remington's Pharmaceutical Science*, 17th ed., Mack Publishing Company, Easton, Pa. (1985), the entire disclosure of which is incorporated herein by reference.

Pharmaceutical compositions can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), chelants (such as, e.g., DTPA or DTPA-bisamide) or calcium chelate complexes (e.g., calcium DTPA, CaNaDTPA-bisamide), or, optionally, additions of calcium or sodium salts (e.g., calcium chloride, calcium ascorbate, calcium gluconate, or calcium lactate). Pharmaceutically-acceptable carriers can include water, buffered water, normal saline, 0.4% saline, 0.3% glycine, hyaluronic acid, and the like. Pharmaceutical compositions can be packaged for use in liquid form, or can be lyophilized.

For solid pharmaceutical compositions, nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like. For example, a solid pharmaceutical composition for oral administration can comprise any of the carriers and excipients listed above and 10-95%, preferably 25%-75%, of the neuroprotective or osteogenic agent. A pharmaceutical composition for aerosol (inhalational) administration can comprise 0.01-20% by weight, preferably 1%-10% by weight, of neuroprotective or osteogenic agent encapsulated in a liposome, as described above, and a propellant. A carrier can also be included as desired, e.g., lecithin, for intranasal delivery.

In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. In other non-limiting examples, a dose may also comprise from at least about 1 microgram/kg/body weight, including about 5, about 10, about 50, about 100, about 200, about 350 weight, about 500 microgram/kg/body weight; or at least about 1 milligram (mg)/kg/body weight, such as about 5, about 10, about 50, about 100, about 200, about 350, about 500, to about 1000 mg/kg/body weight or more per administration, and any range derivable therein.

General Description

Described herein are methods for generating midi- and mini-GAGR, compositions comprising midi- and mini-GAGR, and applications and methods employing such compositions.

In particular embodiments described herein are methods of generating digestion products of low acyl gellan gum (LA-GAGR). In these embodiments, LA-GAGR is enzymatically digested by α1→3 glucosidase. Allowing the digestion to proceed for 24, 48, 72 hours, or longer produces three different digestion products: maxi-GAGR, midi-GAGR, and mini-GAGR, respectively.

Low acyl gellan gum (LA-GAGR) is a polysaccharide consisting of a repeating tetrasaccharide, D-Glc(β1→4)D-GlcA(β1→4)D-Glc(β1→4)L-Rha(α1→3). FIG. 1A shows the chemical structure of LA-GAGR ([D-Glc(β1→4)D-GlcA(β1→4)D-Glc(β1→4)L-Rha(α1→3)]n). Arrows point to either α- or β-glucosidic bonds. Low acyl gellan gum is used as food additive, capsule for drug delivery, and coating for surgical device in human. Low acyl gellan gum shows few side effects in human.

LA-GAGR can be enzymatically digested by α(1→3) glucosidase to generate several digestion products. A 24 hour enzymatic digestion of LA-GAGR results in a digestion product having an average molecular weight of approximately 30,245 g/mol. "midi-GAGR" is generated after 48 hours enzymatic digestion of LA-GAGR. Midi-GAGR has a molecular weight of approximately 4,774 g/mol "mini-GAGR" is generated after ≥72 hours enzymatic digestion of LA-GAGR. Mini-GAGR has a molecular weight of approximately 718 g/mol, which is close to the molecular weight of the basic repeating sugar units of LA-GAGR. Both mini-GAGR and midi-GAGR are believed to have few side effects in human. LA-GAGR may be similarly digested by other glucosidases, for example, α(1→4) glucosidase.

In other embodiments described herein are compositions comprising midi-GAGR and/or mini-GAGR. In accordance with the present disclosure, the compositions described herein have been found to be neuroprotective. In certain specific embodiments, the compositions described herein can be used according to methods described herein to treat neurodegenerative disorders, e.g., Alzheimer's disease, Parkinson's disease, multiple sclerosis, amyotrophic lateral sclerosis, spinal cord injury, and brain trauma. In other embodiments, the compositions are useful for wound healing, promoting collagen production, and promoting blood vessel formation.

In yet other embodiments described herein are methods for treating degenerative neurological or disorder, healing wounds, stimulating collagen production, activating FGF receptors, or stimulating blood vessel formation using the compositions described herein.

While not wishing to be bound by any particular theory, the neuroprotective effect of midi-GAGR is now believed to be attributable to its antioxidant activity, and its ability to bind and interact with fibroblast growth factor receptor 1 (FGFR1), neural cell adhesion molecule 180 (NCAM-180), and neurofascin-186. Because of midi-GAGR's antioxidant activity and ability to bind and interact with NCAM-180, compositions described herein comprising midi-GAGR can be used according to the methods described herein for the treatment of degenerative neurological disorders.

In other particular embodiments described herein, compositions comprising midi- and/or mini-GAGR are useful to enhance osteogenesis of adult mesenchymal stem cells. In certain specific embodiments, the compositions described herein can be used according to methods described herein to treat bone disorders, e.g., oseteoporosis, osteoarthritis, osteogenesis imperfect, and bone fractures. In one embodiment, the osteogenic effect of midi- and mini-GAGR is attributable to the polysaccharides enhancing bone cell formation from human adult mesenchymal cells under osteogenic conditions at low concentrations. Because of midi- and mini-GAGR's osteogenic effect, compositions described herein comprising midi- and/or mini-GAGR can be used according to methods described herein for the treatment of bone disorders.

Wound healing is a complex and dynamic process of replacing devitalized and missing cellular structures and tissue layers. It is mediated by a complex and coordinated series of events such as inflammatory, fibroblastic, and remodeling phases. In addition to the phases, angiogenesis (neo-vascularization), re-epithelization, and production/deposition of new glycosaminoglycans (GAGs) and proteoglycans at a wounded site are important for complete wound healing. Various protein growth factors are used in healing dressing to enhance wound healing. Among the protein growth factors, fibroblast growth factors (FGFs) show noteworthy ability in tissue repair and regeneration, even as a component of wound healing dressing. In spite of this ability, the clinical use of FGFs is limited by their low thermal stability and high sensitivity to proteases. Similarly to FGFs, other protein growth factors are also limited by the same problems. Thus, an alternative wound-healing agent has been searched for.

In accordance with the present disclosure, the strong vasculogenic factors mini-GAGR (the basic unit) and midi-GAGR, which are the cleavage products of low acyl gellan gum (FDA 21 CFR 172.665), are useful for wound healing. These cleavage products have strong enhancing effects on blood vessel formation (i.e., strong angiogenic effect) and tissue matrix production, and interact with the FGF receptor. Midi- and mini-GAGR increase the production of GAG and collagen, the major tissue components that refill wound sites. In addition, these GAGR cleavage products do not cause fat formation. Fat hypertrophy interferes with wound healing. All of this demonstrates that these cleavage products are useful as therapeutic agents for wound healing.

Figure 33:
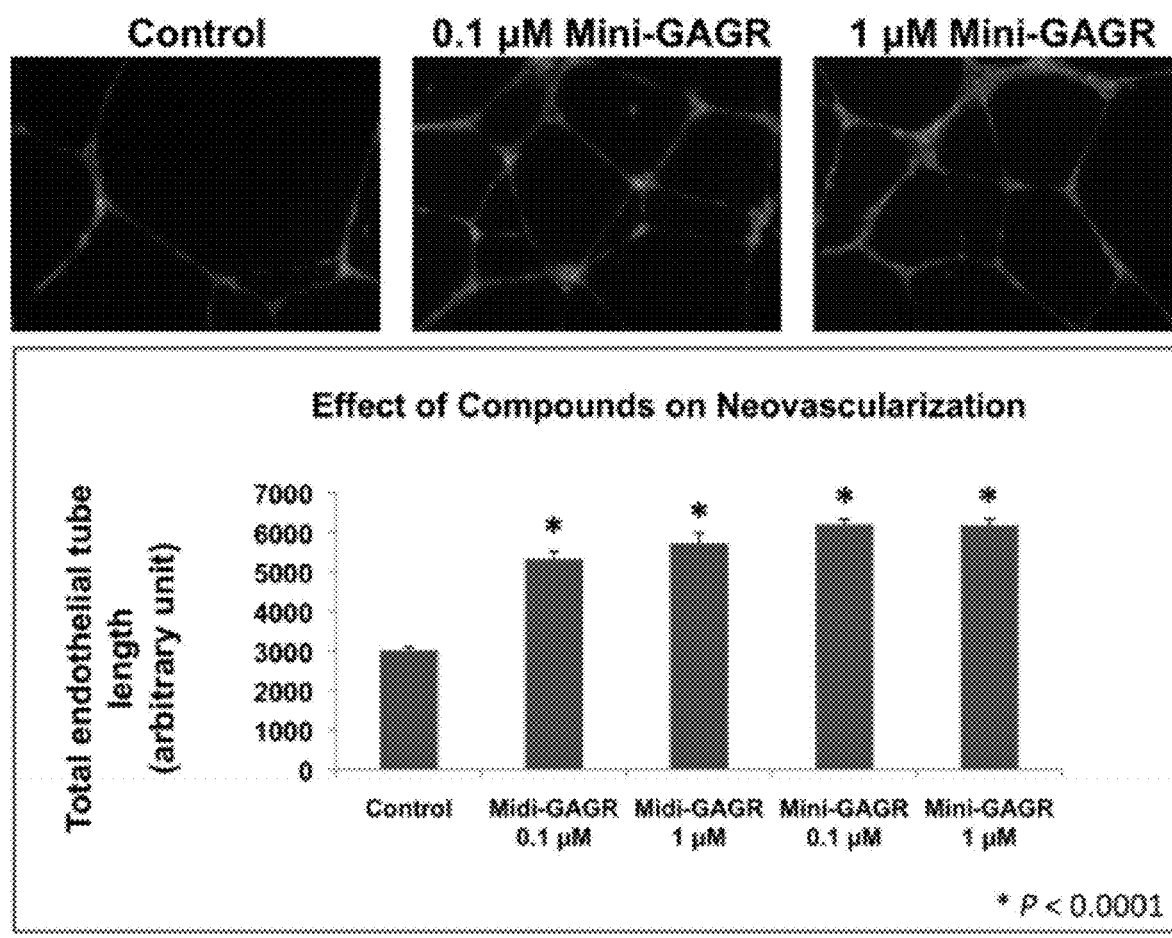
FIG. 33: Human umbilical vein endothelial cells (HU-VECs) were incubated on EGM with 0, 0.1, or 1 μM of mini-GAGR or midi-GAGR for 16-18 h, fixed, and labeled with Acridine Orange. The tubes formed from HUVECs were imaged by fluorescent microscopy. The total length of tubes formed from HUVECs per image was measured by 'Metamorph' software (n=4 experiments).
Figure 34A:
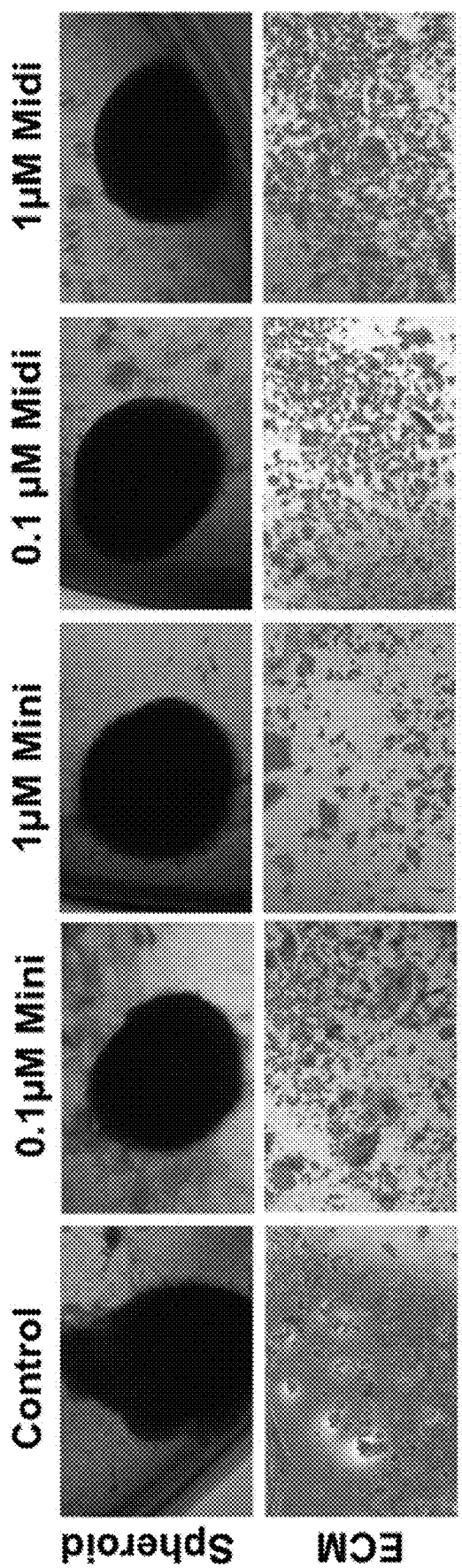
FIGS. 34A-34B: Human bone marrow-derived mesenchymal stem cells (BM-MSCs) in cartilage-forming medium were treated with none or mini-/midi-GAGR (0.1-1 μM) every 2 days in a 24 well plate. On day 14, GAGs were stained with 1% Alcian Blue. The images of Alcian Blue staining of the whole well or individual spheroids were taken by a light microscope.
Figure 34B:
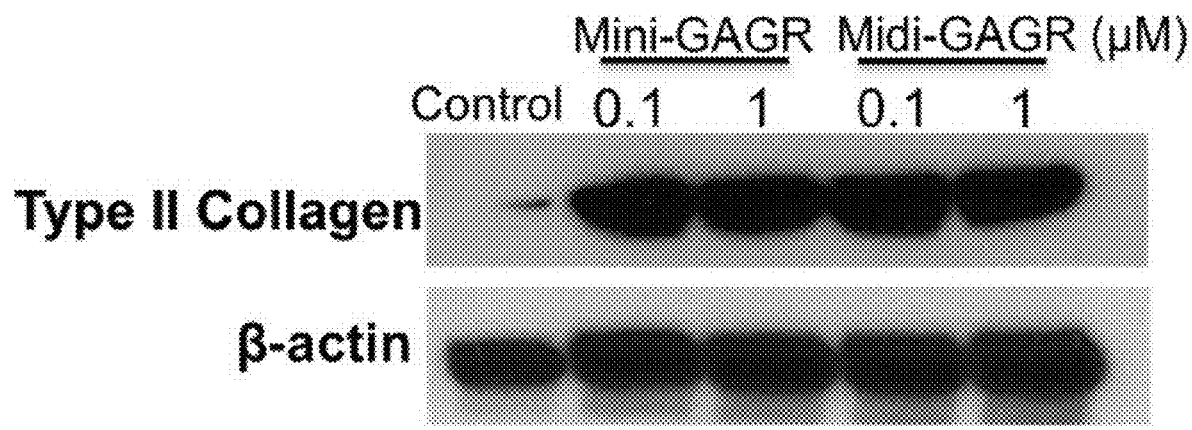
Figure 35:
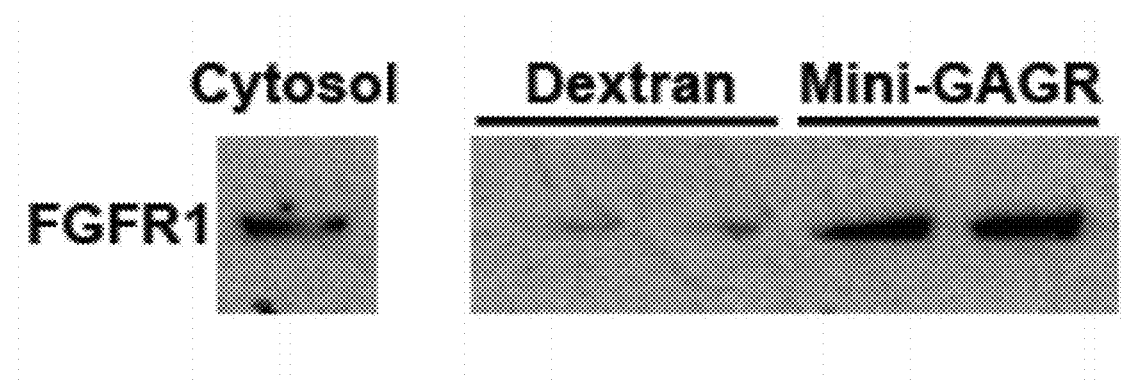
FIG. 35: Dextran or mini-GAGR was conjugated to epoxy sepharose beads according to manufacturer's protocol. The beads were then incubated in the plasma membrane extractions of N2A cells after those were blocked in 2% BSA. FGFR1 protein that bound to the beads was detected by immunoblotting using anti-FGFR1 antibody (n=2).

In the examples herein, treatment with 0.1-1 µM mini-GAGR and midi-GAGR drastically enhanced blood vessel formation from human umbilical vein endothelial cells (HU-VECs) (FIG. 33). Moreover, both mini-GAGR and midi-GAGR increased the production of GAG and collagen, the major tissue components that refill wound sites (FIG. 34). Without wishing to be bound by theory, it is believed that these vasculogenic and GAG-producing effects of mini-GAGR and midi-GAGR are exerted by their interaction with FGF receptor 1 (FGFR1) that binds FGFs and has been shown to be important for wound healing (FIG. 35). In addition, mini-GAGR and midi-GAGR did not enhance cell proliferation and adipogenesis (FIG. 36), indicating that both do not cause tumorigenesis and tissue adipogenesis. Thus, midi- and mini-GAGR have neither mitogenic effect nor adipogenic effect. Importantly, midi-GAGR (likely mini-GAGR, too) shows a long functional half-life (~24 hours) in the body, indicating that they are thermo-stable and degradation-resistant inside the body; that is, they overcome the limitation of protein factors. Moreover, the examples herein show that midi- and mini-GAGR can form blood vessels and extracellular matrix to an extent similar to protein growth factors. Taken together, this demonstrates that midi-GAGR, mini-GAGR, and even their precursor, low acyl gellan gum, have a significant therapeutic ability for wound healing treatment. Moreover, since low acyl gellan gum is already used in human (FDA-approved), it can be readily used for the clinical application in humans.

LA-GAGR and/or its cleavage products midi-GAGR and mini-GAGR can be formulated in a gel product for wound healing applications. In some embodiments, the gel formula can controllably release an effective dose of the LA-GAGR, midi-GAGR, or mini-GAGR at a skin wound site on a subject, such as a human or animal. LA-GAGR and/or its cleavage products are easily encapsulated in a clinical gel for application onto wound sites, and provide the additional benefit of an anti-fouling property. To formulate a gel, the polysaccharide component of LA-GAGR and/or its cleavage products is/are bound to a gelling component. Non-limiting examples of suitable gelling components are chitosan, alginate, hyaluronic acid, hyaluronates, collagen, xanthan gum, pectins, carboxymethylcellulose, arabic gum, and/or the like.

GAGR and/or its cleavage products can be incorporated into the various types of wound dressings currently available, such as hydrogel dressings, perforated plastic film absorbent dressings, hydrocolloid dressings, or alginate dressings. Most commercially available gel dressing do not contain a wound healing agent, but rather merely provide a scaffold for tissue regeneration. Wound healing agents are typically expensive and require a special encapsulation system for focal delivery at the wound site. However, LA-GAGR and its cleavage products are cost-effective and are easily incorporated into a gel dressing. Thus, LA-GAGR and/or its cleavage products can provide for an efficient gel dressing that includes a wound healing agent.

Gel compositions containing LA-GAGR or its cleavage product naturally release the LA-GAGR or its cleavage product over time. Once applied, the gel degrades naturally over time, causing the release of the LA-GAGR or cleavage product.

In certain embodiments of a gel formulation, the formulation includes mini-GAGR. Without wishing to be bound by theory, it is believed that because mini-GAGR is smaller than midi-GAGR, mini-GAGR diffuses better. In certain embodiments of a gel formulation, the formulation includes midi-GAGR. Without wishing to be bound by theory, it is believed that midi-GAGR has a higher antioxidant capacity than mini-GAGR, and is therefore more efficient than mini-GAGR.

Therapeutic/Prophylactic Methods and Compositions

Further described herein are methods of treatment and prophylaxis by administration to a subject an effective amount of a therapeutic compound, i.e., mini- and/or midi-GAGR. In a preferred aspect, the therapeutic is substantially purified. The subject is preferably an animal, including but not limited to, animals such as cows, pigs, chickens, etc., and is preferably a mammal, and most preferably human.

Various delivery systems are useful to administer a therapeutic compound, e.g., encapsulation in liposomes, microparticles, microcapsules, etc. Methods of introduction include, but are not limited to, intradermal, intramuscular, intraperitoneal, intravenous, subcutaneous, intranasal, and oral routes. The therapeutic compounds are administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the therapeutic compositions locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers.

Pharmaceutical Compositions

Such compositions comprise a therapeutically effective amount of a therapeutic, such as mini- and/or midi-GAGR, and a pharmaceutically acceptable carrier or excipient. Such a carrier includes, but is not limited to, saline, buffered saline, dextrose, water, glycerol, ethanol, and combinations thereof. The carrier and composition can be sterile. The formulation will suit the mode of administration.

In one embodiment, pharmaceutical compositions disclosed herein comprise a neuroprotective agent, wherein the agent is LA-GAGR or its digestion product, mixed with a pharmaceutically acceptable carrier. In one particular embodiment, the agent is the digestion product midi-GAGR, mini-GAGR, or a combination thereof.

In another embodiment, the present pharmaceutical compositions comprise an osteogenic agent, wherein the agent is LA-GAGR or its digestion product, mixed with a pharmaceutically acceptable carrier. In one particular embodiment, the agent is the digestion product midi-GAGR, mini-GAGR, or a combination thereof.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In one embodiment, the composition is formulated in accordance with routine procedures as a pharmaceutical composition adapted for intravenous administration to human beings. For example, compositions for intravenous administration are solutions in sterile isotonic aqueous buffer. Where necessary, the composition also includes a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it is be dispensed with an infusion bottle containing sterile pharmaceutical grade water or saline. Where the composition is administered by injection, an ampoule of sterile water for injection or saline is provided so that the ingredients are mixed prior to administration.

The therapeutic formulation can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic formulation which will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation will also depend on the route of administration, and the seriousness of the disease or disorder, and is decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Kits

Also provided are pharmaceutical packs or kits comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

Any of the compositions described herein may be comprised in a kit. In one embodiment, provided herein is a pharmaceutical pack or kit comprising one or more dosage units of LA-GAGR or its digestion product sufficient for one or more courses of treatment for an adult mesenchymal stem cell or wound healing. Associated with such pharmaceutical pack or kit are instructions for administering the LA-GAGR digestion product. Optionally associated with such pharmaceutical pack or kit is a notice in the form prescribed by a governmental agency regulating the manufacture, use or sale of pharmaceuticals or biological products, which notice reflects approval by the agency of manufacture, use or sale for human consumption.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial.

When the components of the kit are provided in one and/or more liquid solutions, the liquid solution is an aqueous solution, with a sterile aqueous solution being one preferred solution.

However, the components of the kit may be provided as dried powder(s). When components are provided as a dry powder, the powder can be reconstituted by the addition of a suitable solvent. It is envisioned that the solvent may also be provided in another container means. It may also include components that preserve or maintain the polysaccharides mini- and midi-GAGR, or that protect against their degradation.

The compounds, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention and without departing from the spirit and scope thereof, can make various changes and modifications of the invention to adapt it to various usages and conditions.

Example 1

Generation of Midi-GAGR and Mini-GAGR

Low acyl gellan gum (LA-GAGR) has an average molecular weight of 99,600 g/mol, based on a tetrasaccharide repeating unit consisting of glucose and glucose derivatives such as glucuronic acid, mannose, and rhamnose connected by (1-3)-α and (1-4)-β (LA-GAGR: [D-Glc($\beta1\rightarrow4$)D-GlcA($\beta1\rightarrow4$)D-Glc($\beta1\rightarrow4$)L-Rha($\alpha1\rightarrow3$)]$_n$). Depending on their functional groups and branches, the molecular weights of the repeating units are 700-1,000 g/mol.

LA-GAGR was enzymatically digested by enzymatic hydrolysis using $\alpha1\rightarrow3$ glucosidase, generating midi-GAGR and mini-GAGR. The digestion was performed in 0.1M acetate buffer (pH 5) containing 1% salicin (cofactor) in glass tubes. A 1% salicin solution was prepared by dissolving 1 g salicin in 100 ml of 0.1 M acetate buffer at pH 5. The salicin solution was then incubated for 6-8 minutes before use. The mixture was shaken lightly in an incubator at 37° C. and 80 rpm. At 24, 48, and 72 hours after the start of enzymatic hydrolysis, the glass tubes were removed from the incubator, placed in a hot water bath for 5 minutes, and then moved to an ice bath to stop the digestion reaction. The 24, 48, and 72 hour digestion products were named mega-GAGR, midi-GAGR, and mini-GAGR, respectively. The samples were refrigerated until molecular weight measurement.

Prior to molecular weight measurement, samples were placed in a vacuum dryer at –60 cmHg gauge at 70° C. The tubes were removed from the vacuum dryer after approximately 8 ml of 0.1 M acetate buffer had evaporated. 1 g of LA-GAGR digestion sample was re-suspended in 30 ml of distilled water. Molecular weights of the resulting LA-GAGR fragments were then measured using a Parallel Plate Rheometer (PPR, Rheometrics, Inc.) equipped with rheometer software (TA Orchestrator, TA Instrument, Inc.). Molecular weights of the LA-GAGR digestion products were determined on the basis of the viscosity-storage modulus profiles of the samples using the RheoAnalyzer program developed by TomCoat Oy, Inc., Finland. The validity of the RheoAnalyzer program was verified by running polystyrene standard (NBS 706) on the PPR and determining the molecular weight of NBS 706 from its viscosity profile. The results of the molecular weight measurements are show in Table 1.

TABLE 1

The molecular weights of LA-GAGR enzymatic digestions.

| | GAGR Before Enzymatic Digestion | 24-hour Enzymatic Digestion | 48-hour Enzymatic Digestion: midi-GAGR | 72-hour Enzymatic Digestion: mini-GAGR |
|---|---|---|---|---|
| Molecular Weight (g/mol) | 99,639 | 30,245 | 4,774 | 718 |

The hydrolysis of LA-GAGR may be also carried out by chemical, physical, or other enzymatic means or any combination thereof.

The chemical hydrolysis of LA-GAGR may be carried out by treatment with an acid but is preferably carried out by treatment with an alkali. The physical hydrolysis may be carried out by shear.

The physical hydrolysis of LA-GAGR may be performed at high pressure (e.g., greater than 500 psi) through a small orifice. This process causes the polymer to break into smaller segments. The homogenization process may be repeated to achieve further reduction in the molecular weight of the polymer.

Sonication may be used to cleave water soluble LA-GAGR into midi-GAGR and mini-GAGR. This method involves exposing the polymer sample to high frequency waves.

The use of gamma radiation from either cobalt or electron beam sources also can cleave water soluble LA-GAGR into midi-GAGR and mini-GAGR. The molecular weight reduction occurs most readily when the polymer is in the hydrated, rather than dry, form. For liquid samples, radiation levels from 0.25 to 5 Mrad provide significant reductions in molecular weight.

The hydrolysis of LA-GAGR may be performed by exposing the polymer to an oxidizing agent such as hydrogen peroxide. This oxidative degradation is enhanced by transition metal cations such as iron. It is inhibited by oxygen and free radical scavengers such as ascorbate or propyl gallate.

Acid hydrolysis can be used to reduce the molecular weight of polymers. Also, acid hydrolysis can be used in chemical analysis of polysaccharides to break them down to their constituent sugars. In certain embodiments, although many different acids may be used, generally weak acids are easier to work with than strong acids.

Midi-GAGR and mini-GAGR may be generated by enzymatic biosynthesis using nucleoside diphosphate glycosyl derivative (e.g., uridine/thymidine diphosphate [UDP/TDP] glycosyl derivative) from a nucleotide triphosphate (e.g., uridine/thymidine triphosphate) and a glycosyl phosphate ester (e.g., glucose-1-phosphate, rhamnose-1-phosphate, glucuronic acid-1-phosphate). UDP/TDP-rhamnose may be generated from UDP/TDP-glucose by chemical/enzymatic reaction (e.g., epimerization). UDP/TDP-glucuronic acid may be generated from UDP/TDP-glucose by chemical/enzymatic reaction.

Figure 2:
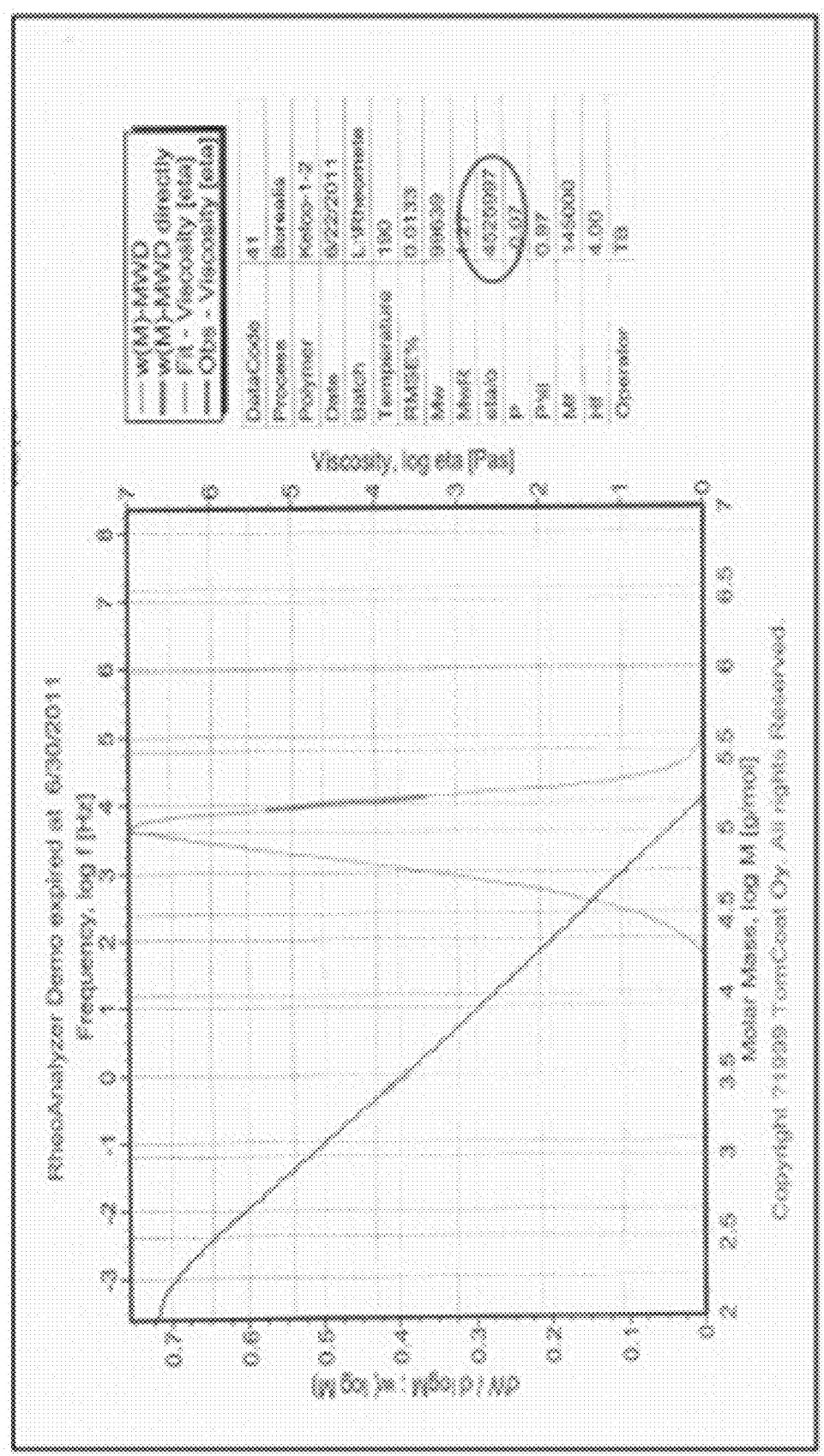
FIG. 2: Rheometer measurement of low acyl gellan gum (LA-GAGR). LA-GAGR shows an average molecular weight of approximately 99,639 g/mol.

FIG. 2 shows the readout of the rheometer measurement for LA-GAGR. The undigested LA-GAGR had an average molecular weight of approximately 99,636 g/mol, which is close to the reported average of 99,600 g/mol.

Figure 3:
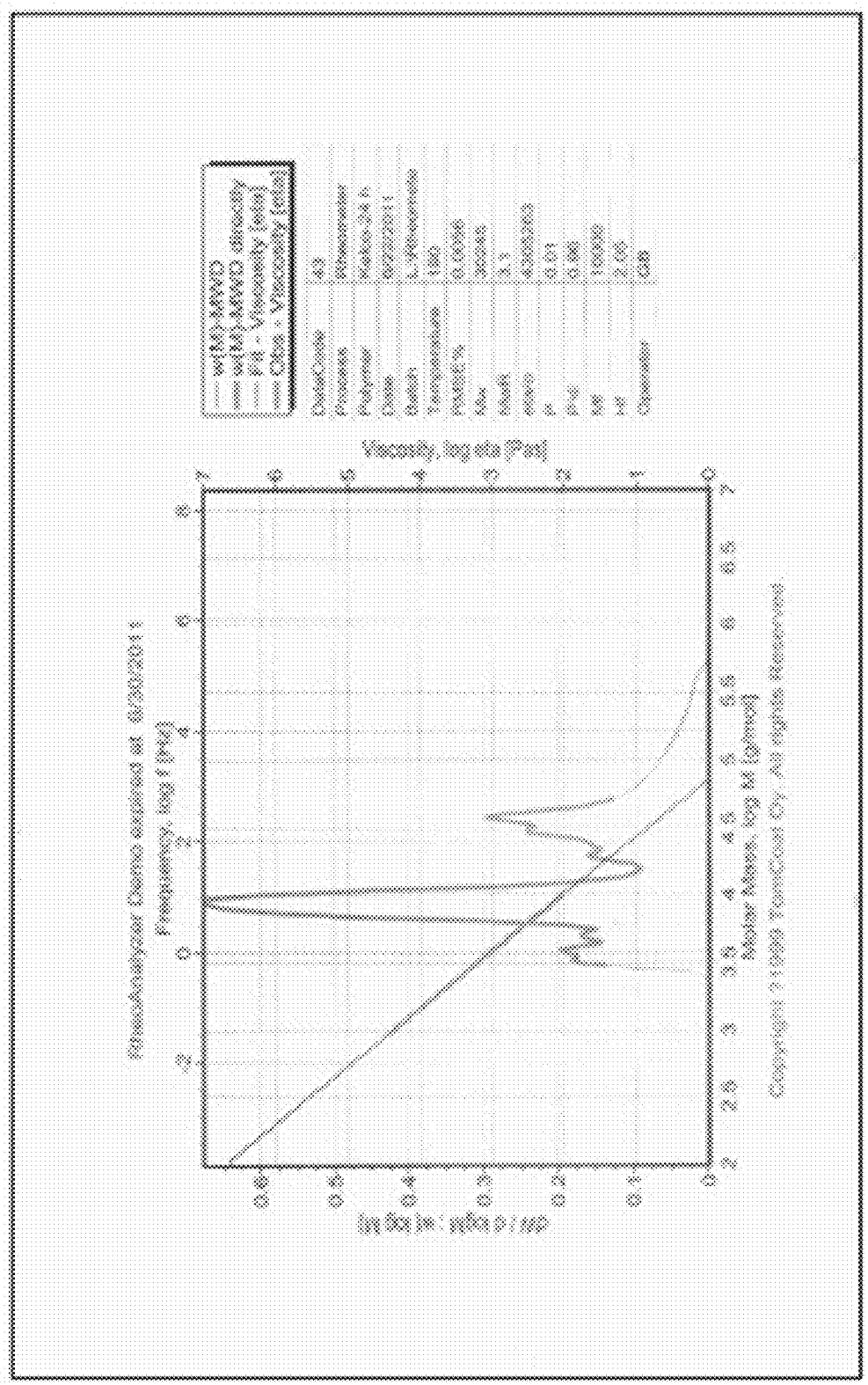
FIG. 3: Rheometer measurement of 24 hour LA-GAGR digestion product. After 24 hours of enzymatic hydrolysis, the average molecular weight of LA-GAGR digestion product was reduced to approximately 30,245 g/mol. The three peaks shown indicate that $\alpha(1\rightarrow3)$-glucosidase breaks down LA-GAGR in multiple steps.

After 24 hours of enzymatic digestion, the average molecular weight of the LA-GAGR digestion product was reduced to approximately 30,245 g/mol (FIG. 3). The three peaks shown in FIG. 3 indicate that $\alpha1\rightarrow3$ glucosidase breaks down LA-GAGR in multiple steps. The 48-hour digestion of LA-GAGR, midi-GAGR, yielded a product of approximately 4,775 g/mol (FIG. 4).

Figure 4:
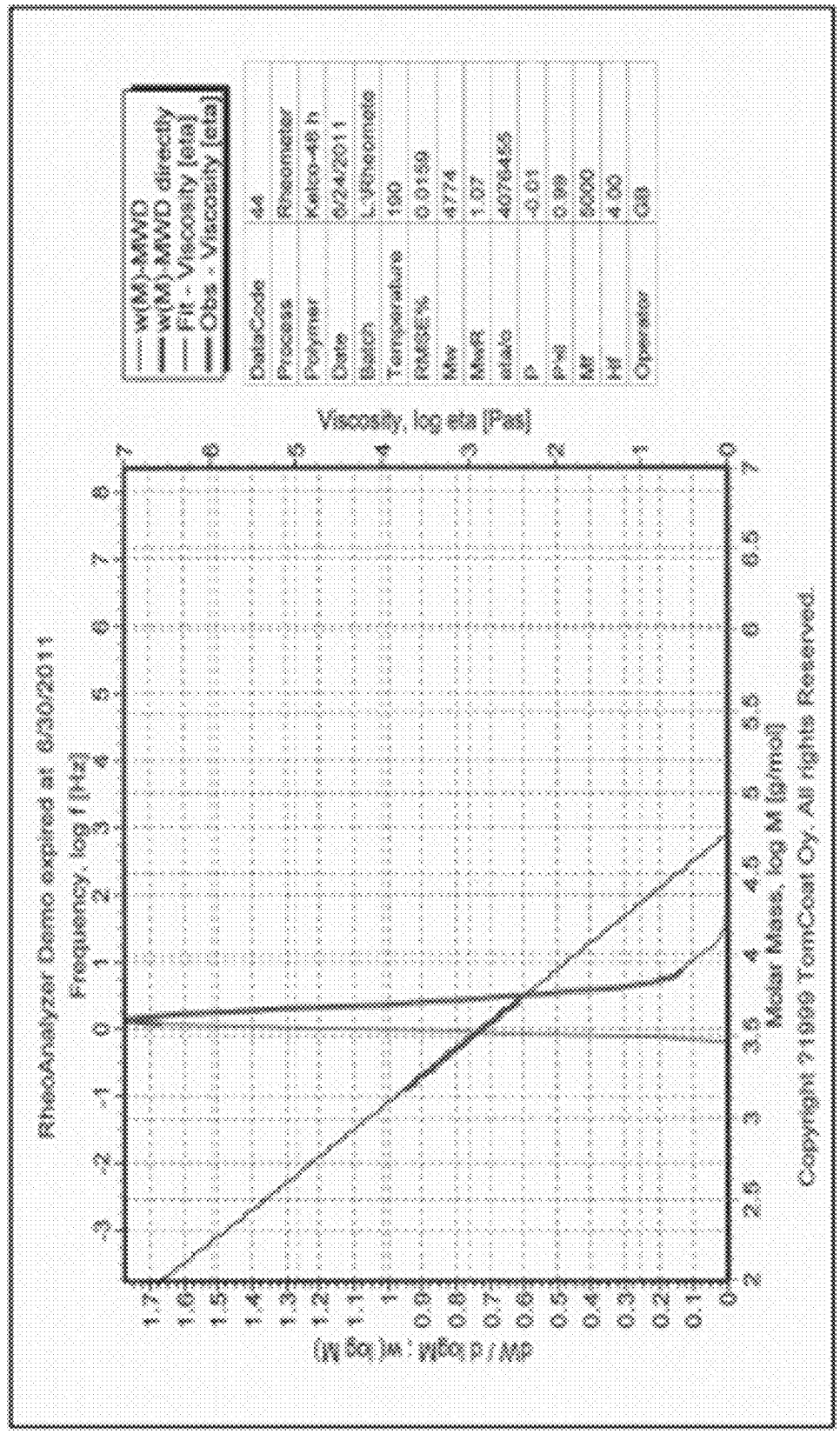
FIG. 4: Rheometer measurement of 48 hour LA-GAGR digestion product, midi-GAGR. 48 hour enzymatic digestion of LA-GAGR yielded a product of approximately 4,775 g/mol (midi-GAGR). The single narrow peak shown indicates that 48 hour digestion yielded a single product of an approximate equivalent length (molecular weight).
Figure 5:
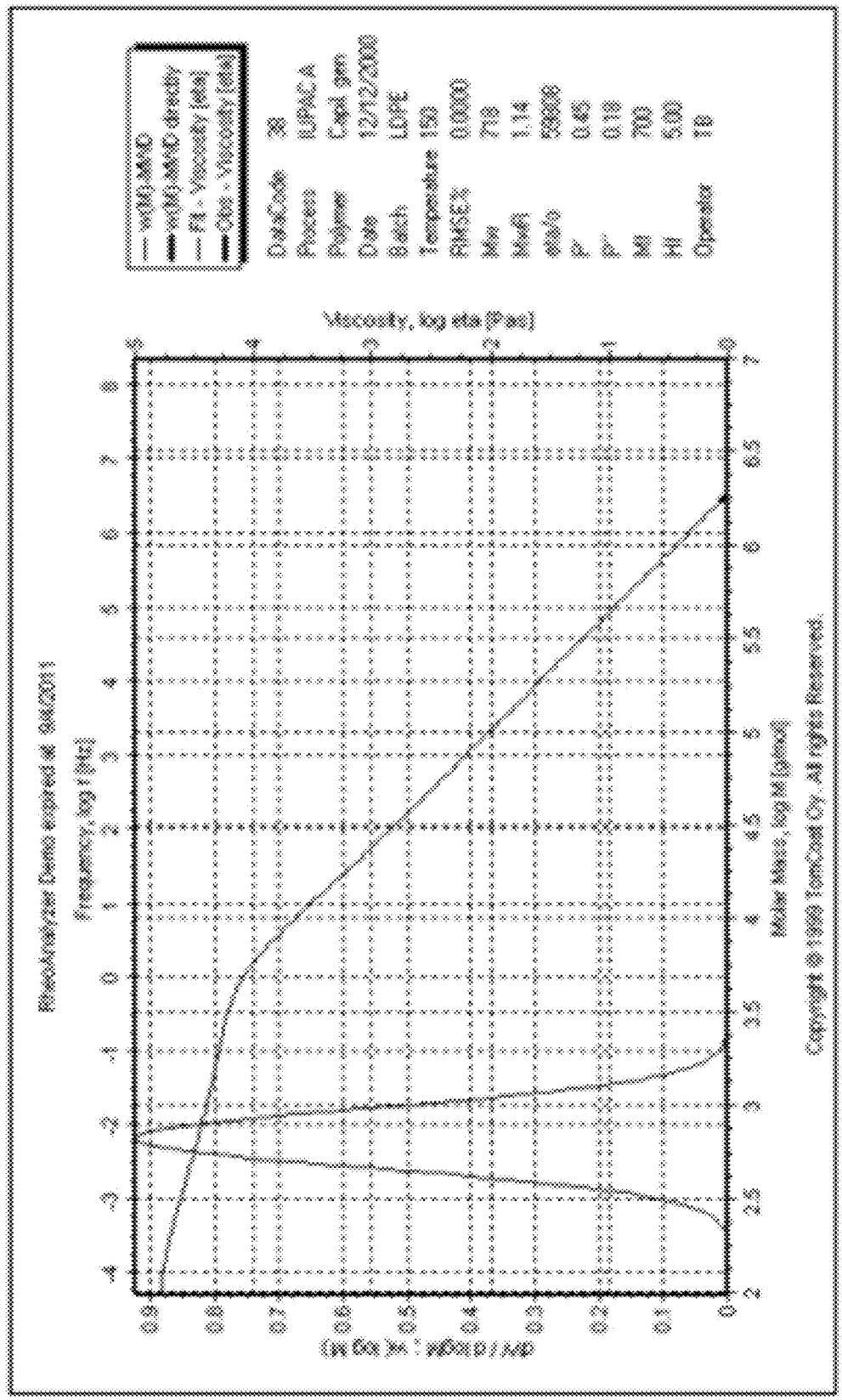
FIG. 5: Rheometer measurement of 72 hour LA-GAGR digestion product, mini-GAGR. 72 hours of enzymatic digestion of LA-GAGR yielded a product of approximately 718 g/mol (mini-GAGR).

The single narrow peak shown in FIG. 4 indicates that 48-hour enzymatic digestion yielded a polysaccharide product of an approximate equivalent length (molecular weight). 72-hour enzymatic digestion of LA-GAGR yielded a product of approximately 718 g/mol (mini-GAGR), which is close to the molecular weight of the basic repeating sugar units of LA-GAGR (FIG. 5).

Example 2

Mini-GAGR as a Novel Neurotrophic Agent midi-GAGR protects cortical neurons from the neurocytotoxicity of amyloid β peptide.

Primary cultures of mouse embryonic cortical neurons (embryonic days of 17 [E17], 14 days in vitro [DIV14]) were treated with mock ($H_2O$) or 1 μM of dextran, alginate, high acyl gellan gum (HA-GAGR), or midi-GAGR for 6 h and then with 10 μM $Aβ_{42}$ for 48 h.

Figure 6A:
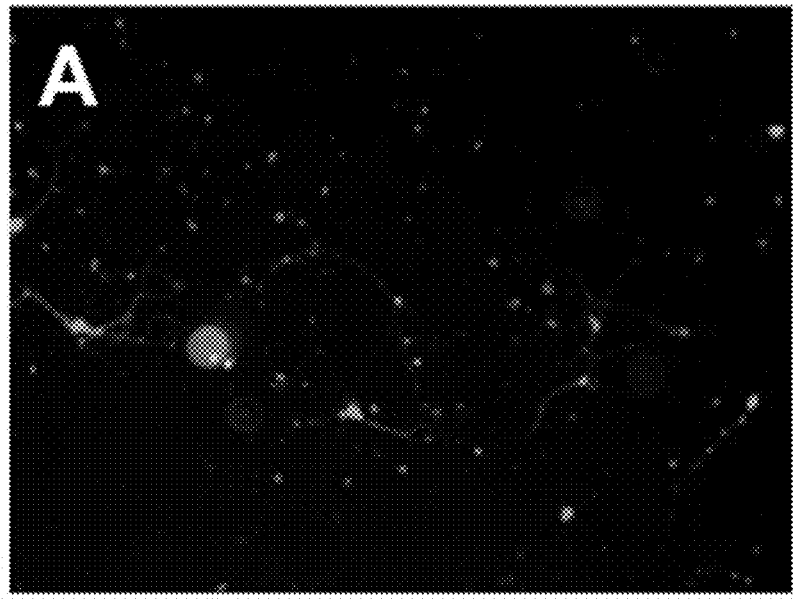
FIGS. 6A-6B: Midi-GAGR protects cortical neurons from the neurotoxicity of amyloid β peptide. Primary cortical neurons were treated with mock or 1 μM of dextran (FIG. 6A), alginate, high acyl gellan gum, or midi-GAGR (FIG. 6B) for 6 h prior to the treatment with 10 μM amyloid β peptide for 48 h. The viability of neurons was assessed using LIVE/DEAD Viability/Cytotoxicity Assay Kit. Dead cells appear red and live cells appear green.
Figure 6B:
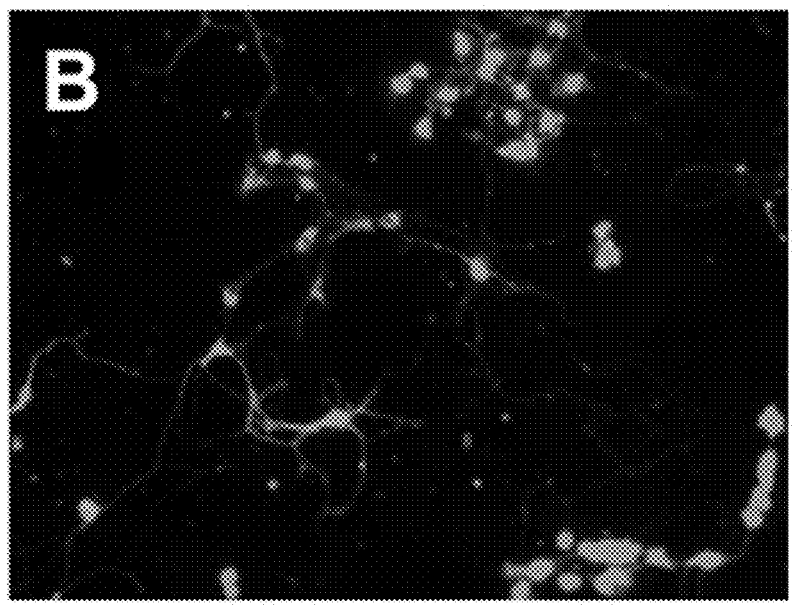
Figure 6C:
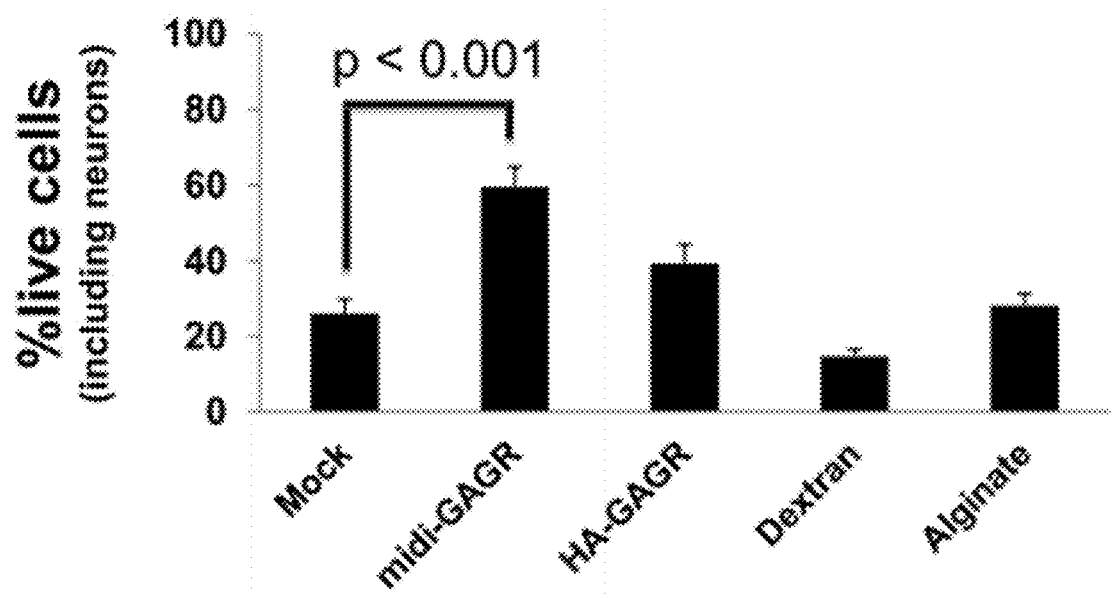
FIG. 6C: Midi-GAGR protects cortical neurons from the neurotoxicity of amyloid β peptide. Depicted is a bar graph showing the percent of live cells (n>200 cells per condition× 3, Mean±SEM).
Figure 6D:
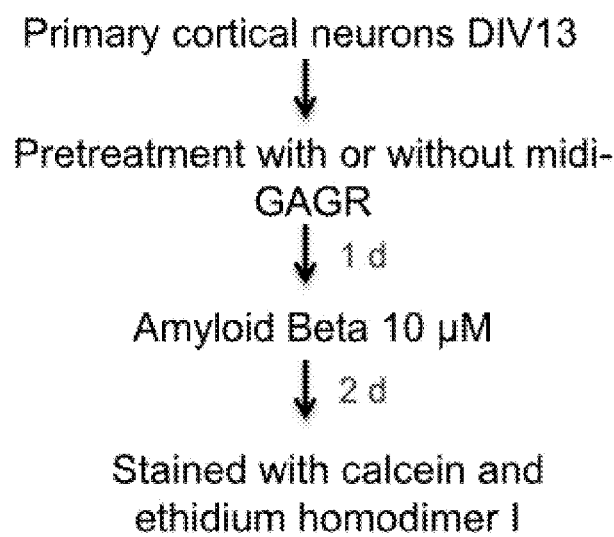
FIG. 6D: Midi-GAGR protects cortical neurons from the neurotoxicity of amyloid β peptide. Depicted is a flow chart summarizing the treatment protocol of primary cortical neurons used to generate FIGS. 6A-6C.

The viability of neurons was assed using LIVE/DEAD Viability/Cytotoxicity Assay Kit (Invitrogen Inc.). midi-GAGR increased the percent of cell survival in neurons exposed to 10 μM $Aβ_{42}$ by ~2.2 fold (FIGS. 6A-6C). The other sugar polymers had no effect.

Midi-GAGR is a Strong Antioxidant

The antioxidant capacity of midi-GAGR was measured using ABTS Antioxidant Assay Kit (Zenbio Co.). Midi-GAGR showed strong anti-oxidant capacities (10 μM midi-GAGR=16.9 μM trolox). This was slightly stronger than antioxidant capacity of LA-GAGR (10 μM LA-GAGR=15.4 μM trolox) (Table 2).

TABLE 2

Antioxidant Capacity of LA-GAGR and midi-GAGR

| ABTS assay | μM Trolox |
|---|---|
| LA-GAGR | 15.4 |
| midi-GAGR | 16.9 |

Figures 7A, 7B:
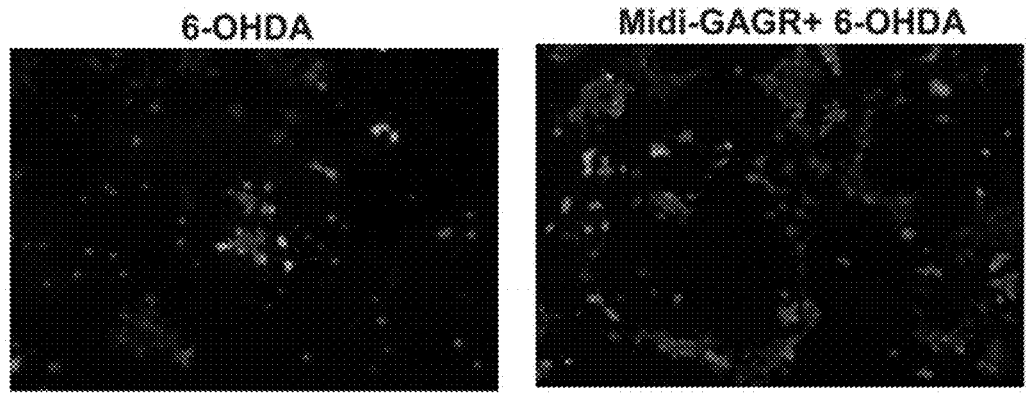
FIGS. 7A-7B: Midi-GAGR has neuroprotective effects on differentiated PC12 cells and primary neurons. PC12 cells were differentiated in 100 ng/ml NGF, treat with mock (FIG. 7A), midi-GAGR (FIG. 7B), dextran, or alginate for 6 h, and then with 6-OHDA for 24 h. Dead cells in red and live cells in green.
Figure 7C:
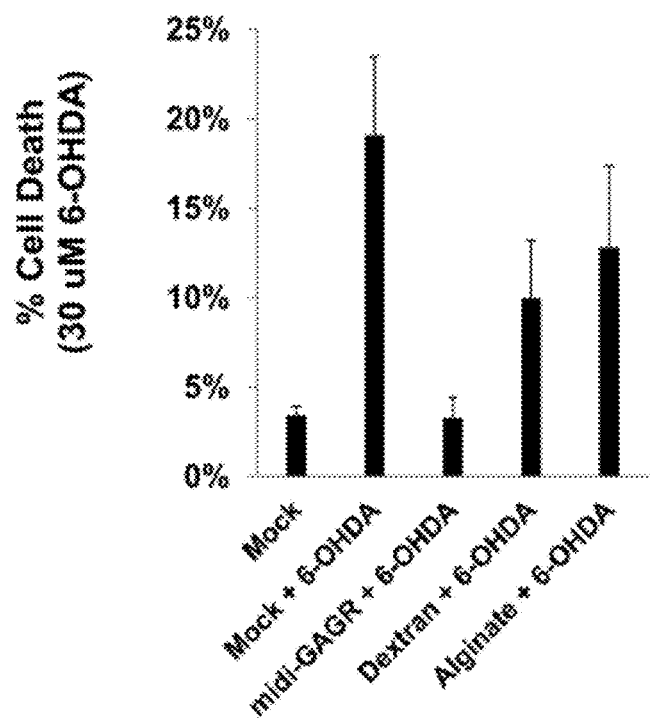
FIG. 7C: Midi-GAGR has neuroprotective effects on differentiated PC12 cells and primary neurons. Depicted is a bar graph showing the percent of dead cells (n>800 cells per condition×3, mean±SEM).
Figure 8A:
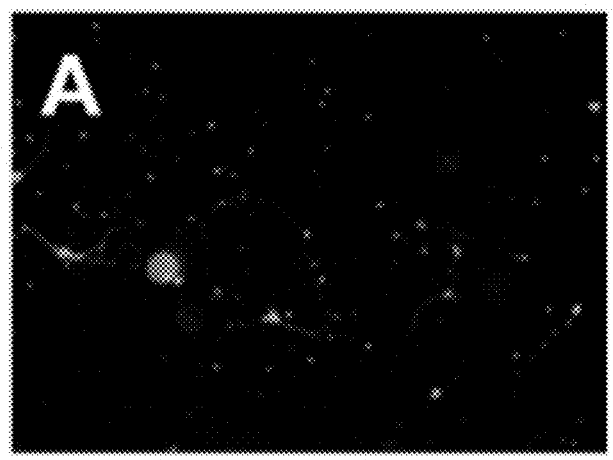
FIGS. 8A-8B: Midi-GAGR has neuroprotective effects on differentiated PC12 cells and primary neurons. Primary cortical neurons were treated with mock (FIG. 8A) or 1 µM of midi-GAGR (FIG. 8B), dextran, alginate, or high acyl gellan gum for 6 h prior to the treatment with amyloid β peptide for 24. Dead cells in read and live cells in green.
Figure 8B:
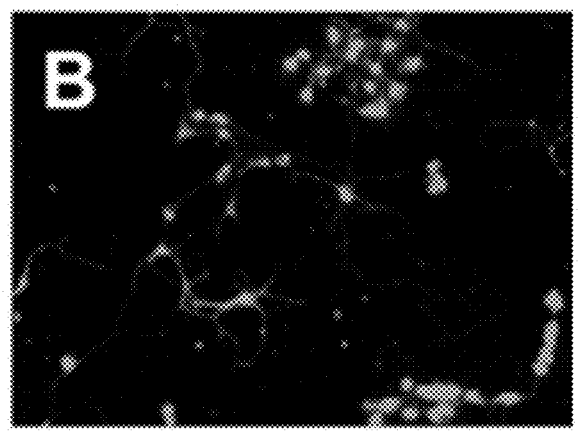
Figure 8C:
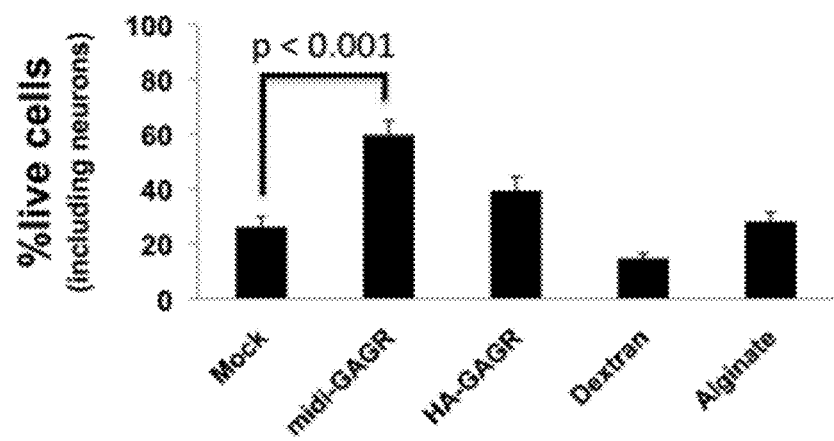
FIG. 8C: Midi-GAGR has neuroprotective effects on differentiated PC12 cells and primary neurons. Depicted is a bar graph showing the percent of live cells (n>200 cells per condition×3, mean±SEM).

Midi-GAGR has Neuroprotective Effect on Differentiated PC12 Cells and Primary Neurons Differentiated dopaminergic PC12 cells and primary mouse embryonic cortical neurons (E17, DIV14) were treated with mock ($H_2O$) or 1 μM of dextran, alginate, HA-GAGR, or midi-GAGR for 6 h and insulated by oxidative stressors (30 μM 6-OHDA [PC12] and 10 μM amyloid β peptide [cortical neurons]) for 24 h. The viability of neurons was assessed using LIVE/DEAD Viability/Cytotoxicity Assay Kit (Invitrogen). midi-GAGR prevented 6-OHDA-induced cell death in differentiated PC12 cells while mock, dextran, and alginate did not (FIGS. 7A-7C). midi-GAGR also increased the percent of live neurons exposed to amyloid β peptide by ~2.2 fold while other sugars did not (FIGS. 8A-8C). This shows that midi-GAGR has neuroprotective effect on both dopaminergic PC12 cells and primary neurons.

Treatment with midi-GAGR increased the levels of phosphorylated CREB in the nuclei of cortical neurons.

Figure 9A:
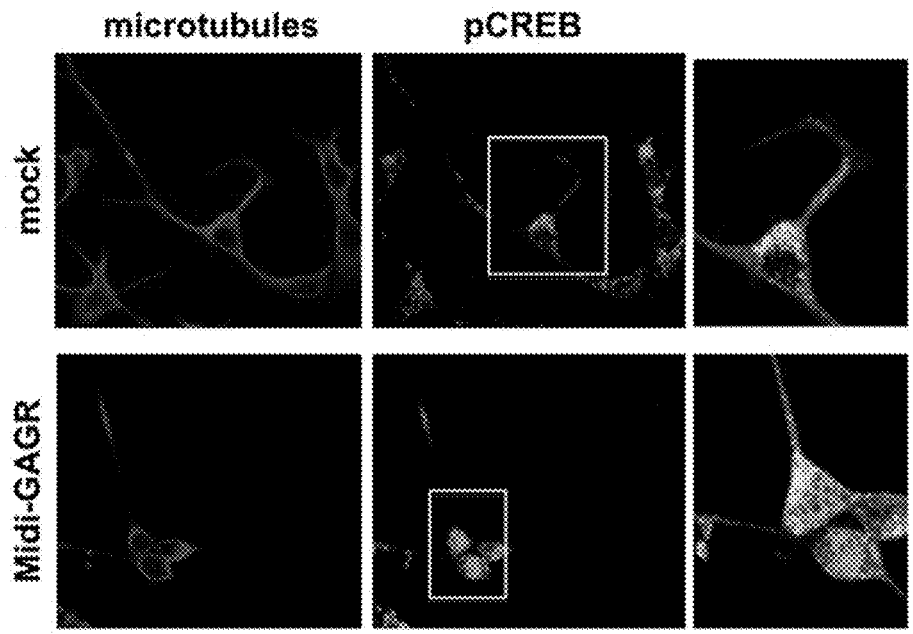
FIG. 9A: Midi-GAGR increases the levels of phosphorylated CREB in the nucleus. Differentiated PC12 cells were treated with mock or 1 µM midi-GAGR, dextran, or alginate and stained with antibodies to α-tubulin (red) and pCREB (green) along with DAPI (blue).
Figure 9B:
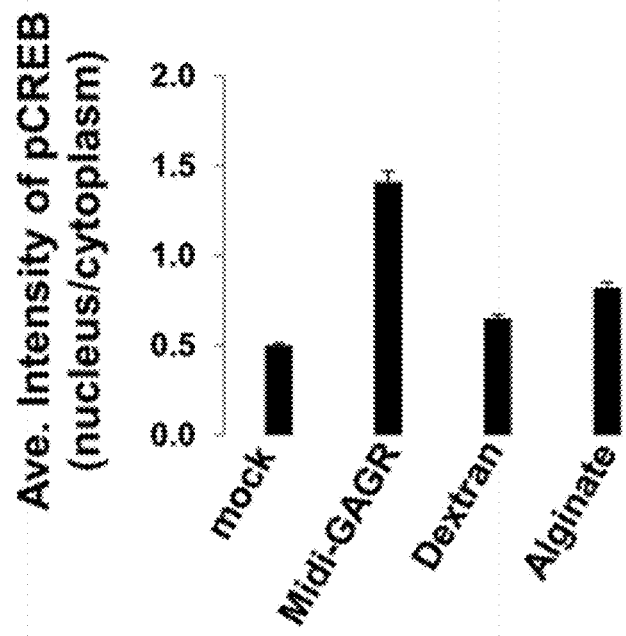
FIG. 9B: Midi-GAGR increases the levels of phosphorylated CREB in the nucleus. Depicted is a bar graph showing the average intensities of pCREB in the nucleus/cytoplasm (n=100 cells, mean±SEM).
Figure 10A:
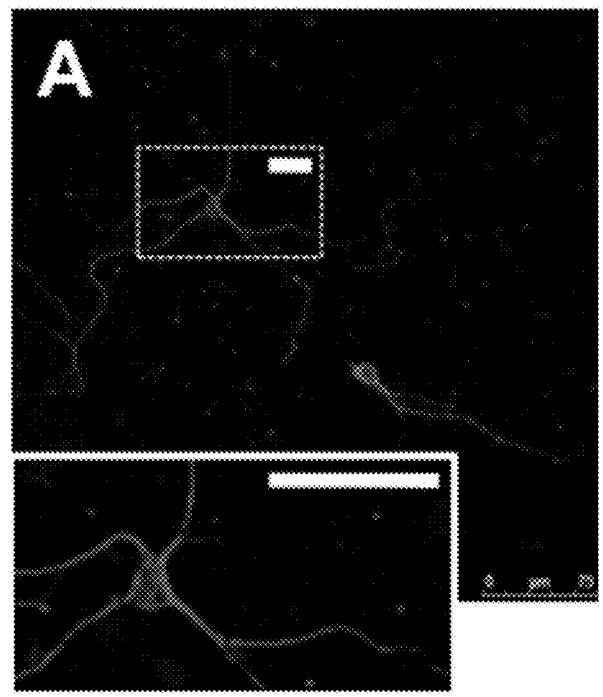
FIGS. 10A-10B: Midi-GAGR increases the levels of phosphorylated CREB in the nucleus. Mouse embryonic cortical neurons were treated with mock or 1 µM dextran (FIG. 10A), alginate, high acyl gellan gum, or midi-GAGR (FIG. 10B) and processed for immunocytochemistry using antibodies to α-tubulin (red) and pCREB (green) along with DAPI (blue).
Figure 10B:
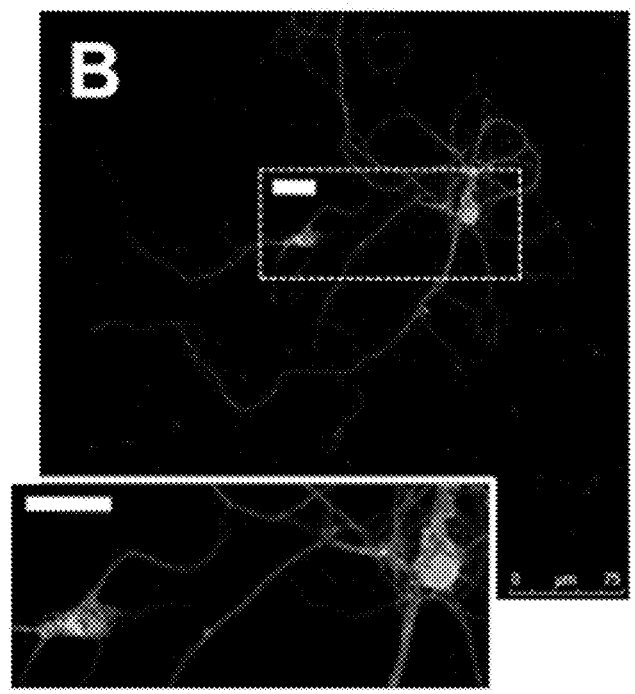
Figure 10C:
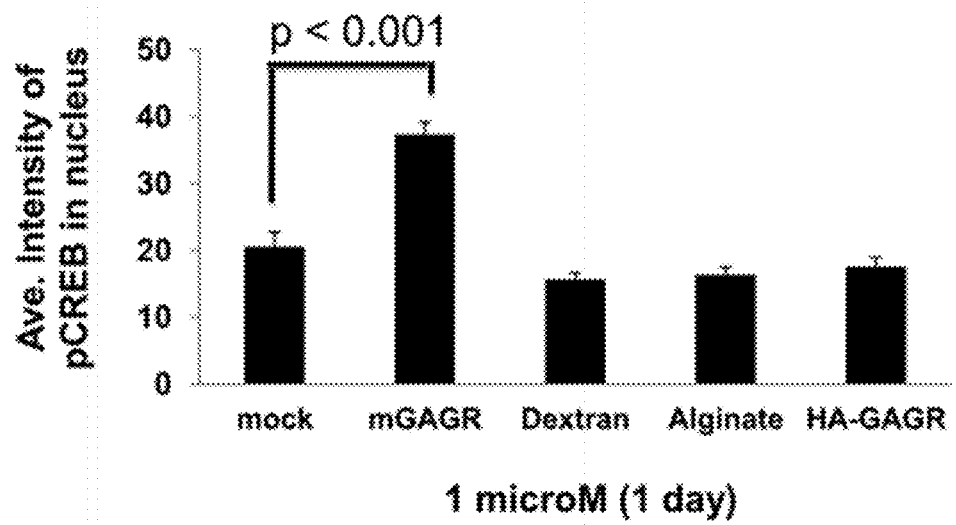
FIG. 10C: Midi-GAGR increases the levels of phosphorylated CREB in the nucleus. Depicted is a bar graph showing the average intensities of pCREB in the nuclei (n=50 neurons, mean±SEM).
Figure 10D:
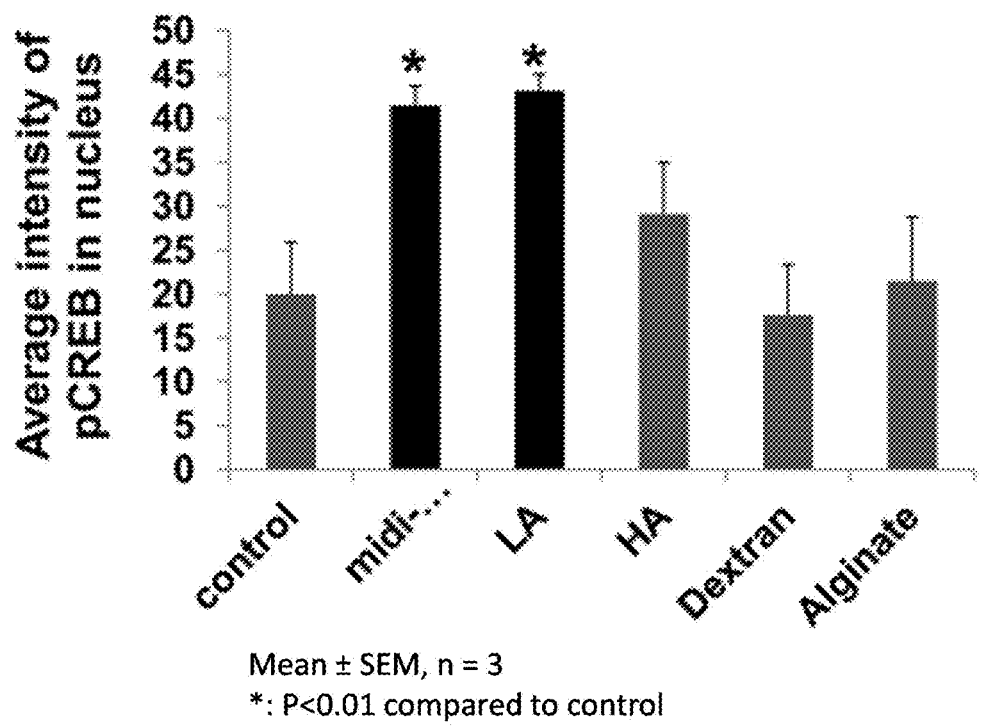
FIG. 10D: Midi-GAGR increases the levels of phosphorylated CREB in the nucleus. Depicted is a bar graph showing the average intensities of pCREB in the nuclei.

Differentiated PC12 cells and mouse embryonic cortical neurons (E17, DIV14) were treated with mock, dextran, alginate, HA-GAGR, or midi-GAGR (1 μM) for 24 h and fixed in 3.7% paraformaldehyde. The fixed cells and neurons were immunostained with antibodies against α-tubulin and phospho-CREB (p-CREB) along with DAPI (nucleus). 1 μM midi-GAGR increased the levels of nuclear p-CREB by ~3 fold in PC12 cells (FIGS. 9A-9B) and by ~1.7 fold in cortical neurons (FIGS. 10A-10C), while nuclear levels of nuclear p-CREB were not significantly increased by mock, dextran, alginate, or HA-GAGR. These data show that midi-GAGR activates a neurotrophic signaling pathway.

Midi-GAGR has a Neuritogenic Activity

Figure 11A:
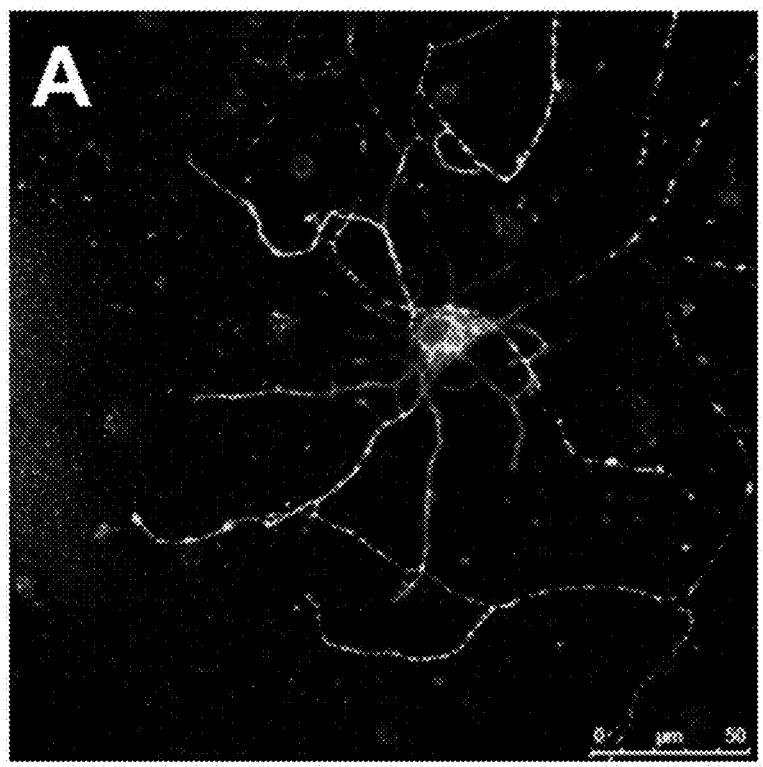
FIGS. 11A-11D: Midi-GAGR has a neuritogenic activity. Embryonic cortical neurons were treated with mock (FIG. 11A) or 1 µM midi-GAGR (FIG. 11B) for 2 days and then with 25 µM 4-HNE (FIG. 11C: pretreated with mock.
Figure 11B:
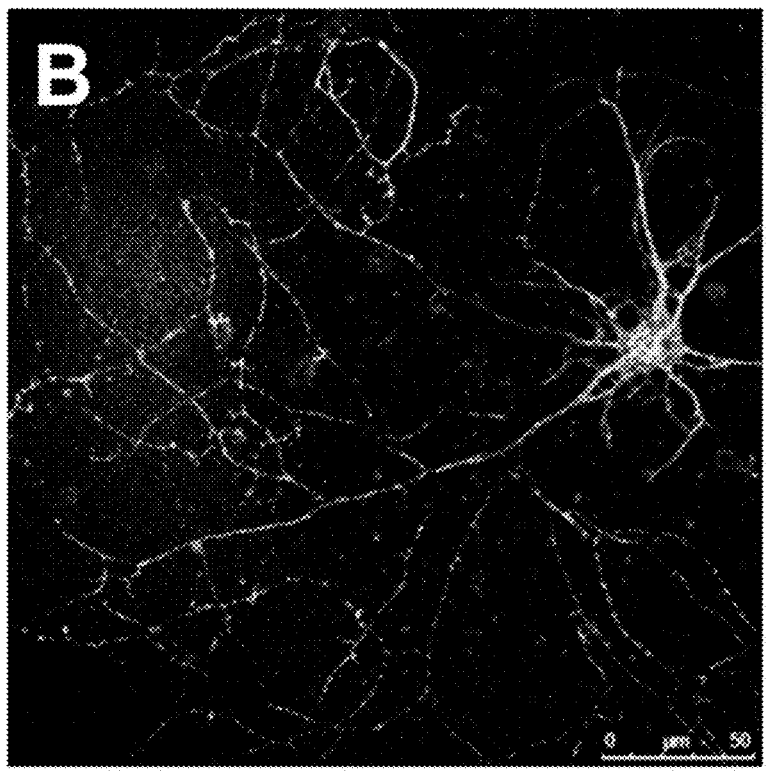
Figure 12A:
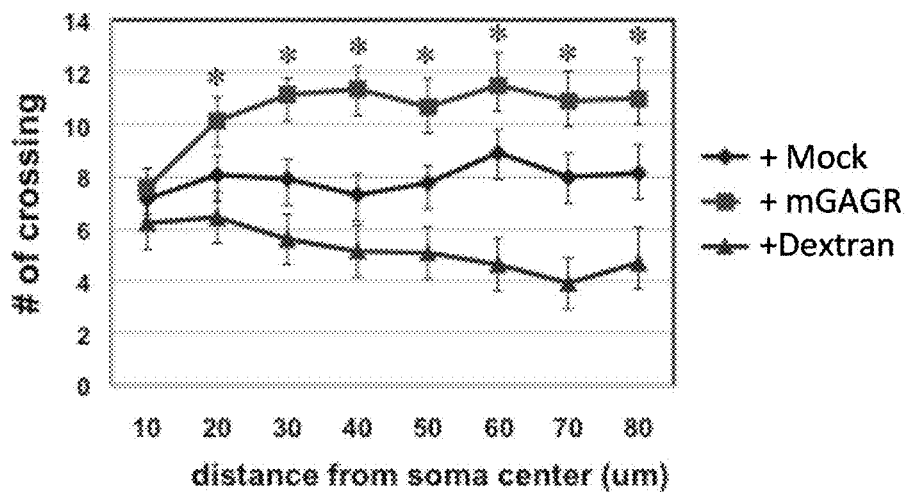
FIGS. 12A-12B: Midi-GAGR has a neuritogenic activity. Depicted is a line graph showing the numbers of dendrite crossings (FIG. 12A), and a bar graph showing the number of synaptic clusters (per 15 µm) (FIG. 12B) in cortical neurons treated with mock, 1 µM dextran or 1 µM midi-GAGR. The numbers of dendritic crossing and synaptic clusters were quantified by Scholl ring analysis and Metamorph (n=30 neurons×2, mean±SEM, *=p<0.001).
Figure 12B:
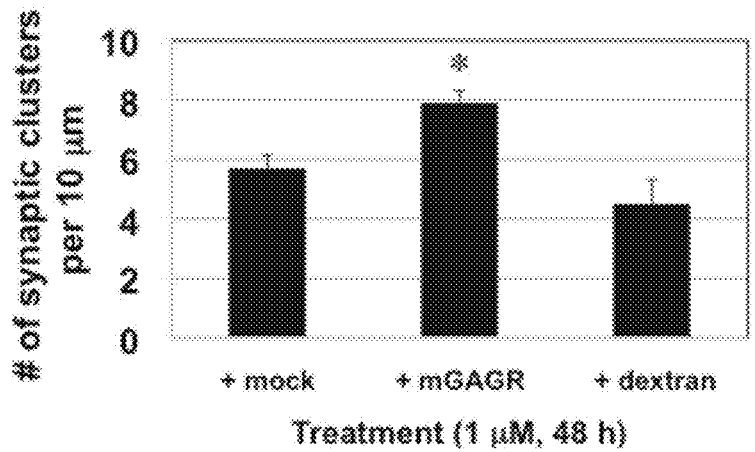
Figure 12C:
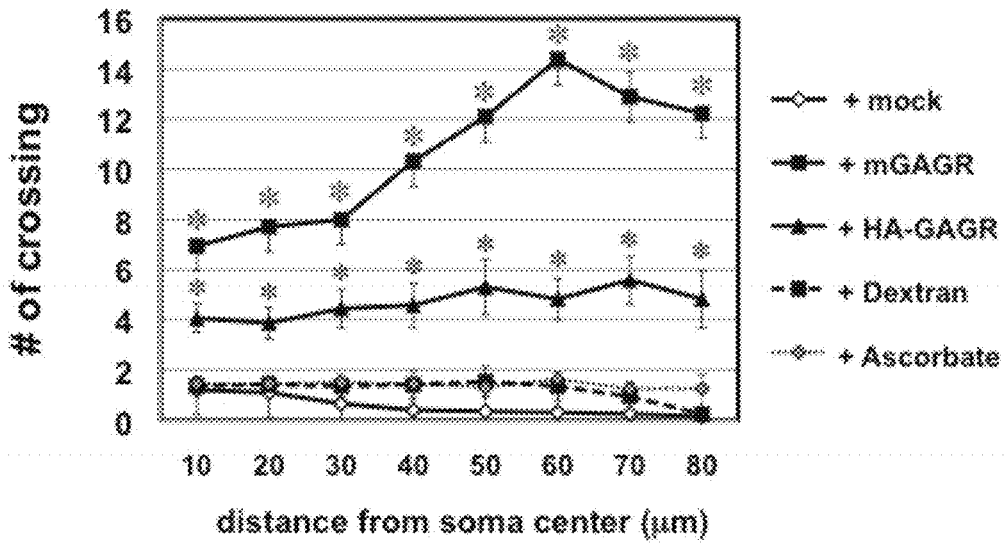
FIG. 12C: Midi-GAGR has a neuritogenic activity. Depicted is a line graph showing the numbers of crossings counted in neurons pretreated with mock, 1 µM dextran, 100 µM ascorbate, 1 µM high acyl gellan gum, or 1 µM midi-GAGR, and then treated with 25 µM 4-HNE (n=30 neurons×2, mean±SEM, * (dark colored star)=p<0.01, * (light colored star)=p<0.001 compared to mock).

E16 rat embryonic cortical neurons (DIV14) were treated for 2 days with mock (FIG. 11A), 1 μM dextran, or 1 μM midi-GAGR (FIG. 11B), fixed and immunostained with anti-synaptophysin antibody (green) and rhodamine-labeled phalloidin (actin: red). Scholl ring analysis was performed to quantify dendritic arbors—the number of crossings as a function of distance from the soma between 0 and 120 μm (mean±S.E.M.). The average number of synaptic clusters per 10 μM of distal dendrite was also quantified. The number of crossings (0-120 μm) was higher in neurons treated with 1 μM midi-GAGR than mock- and dextran-treated neurons (FIG. 12A). The density of synaptic clusters was increased by ~20% ($p<0.03$) in neurons treated with 1 μM midi-GAGR (FIG. 12B).

Neurons Treated with Midi-GAGR Maintain their Neurites

Figure 11C:
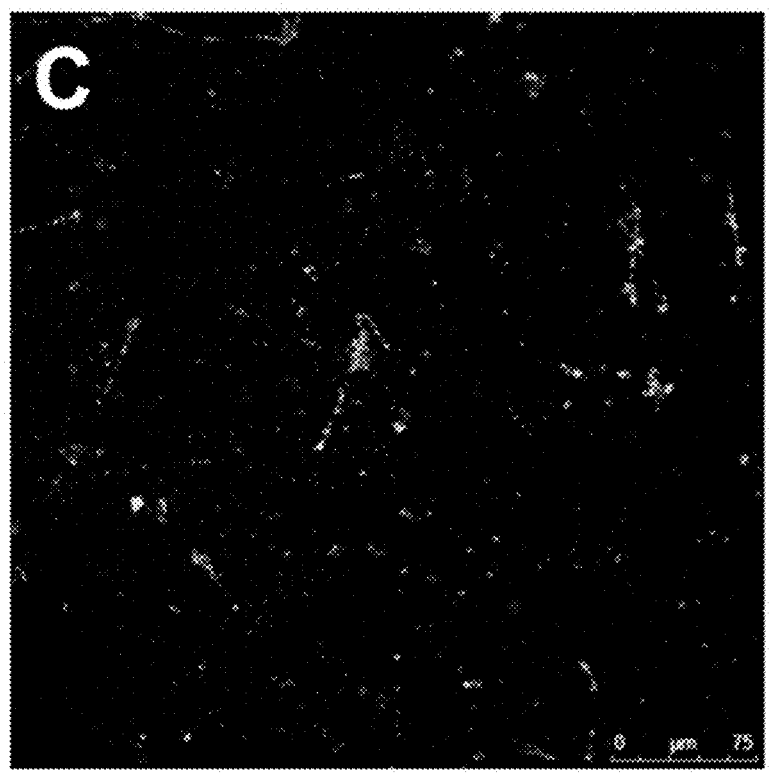
Figure 11D:
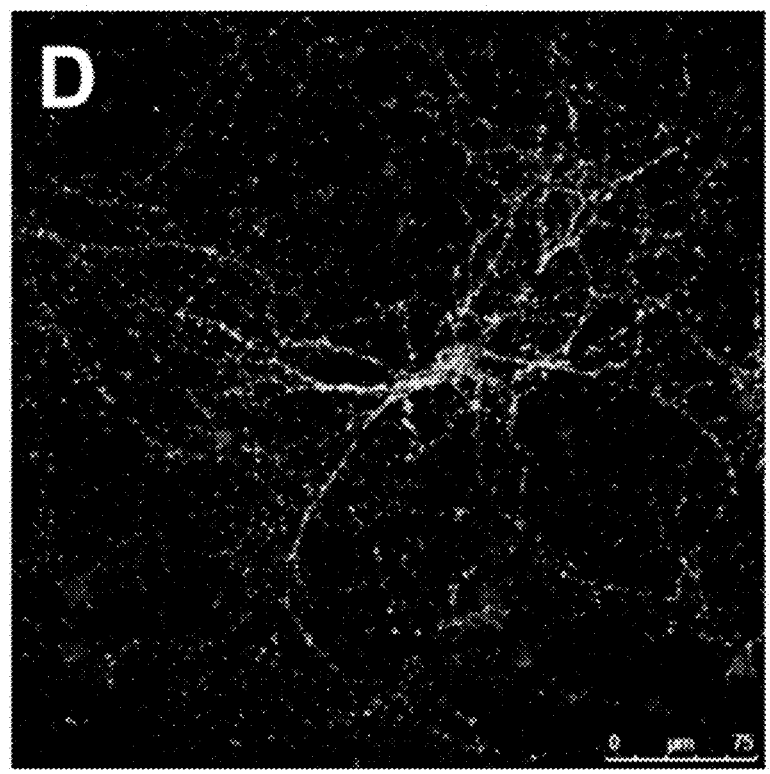
Figure 13A:
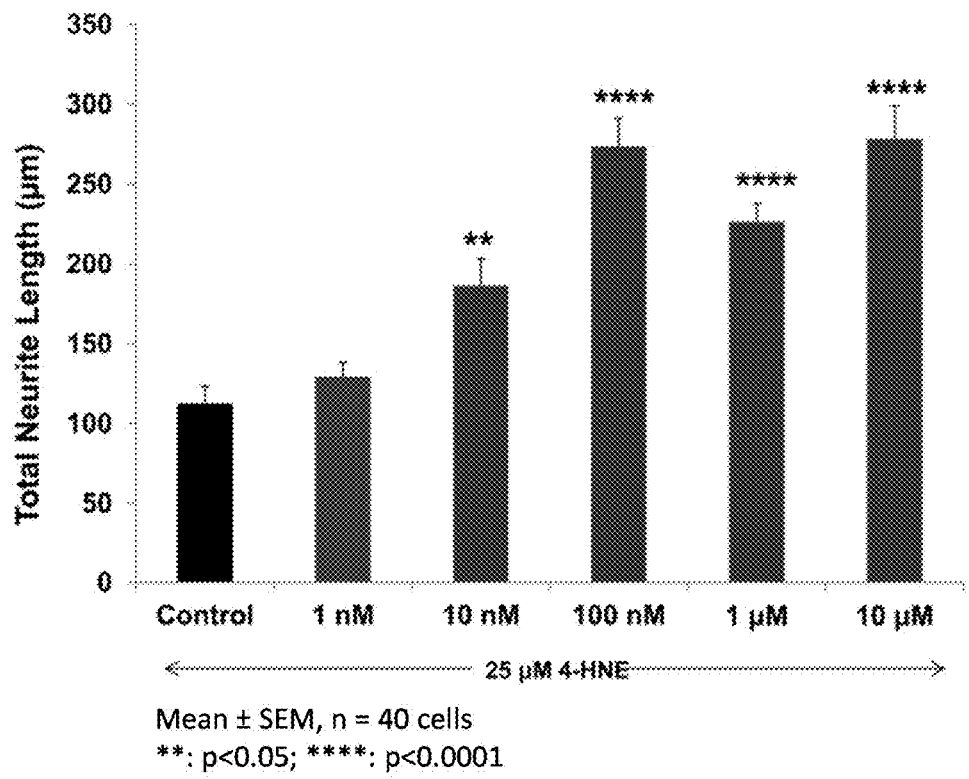
FIG. 13A: Midi-GAGR has a neurite outgrowth enhancing effect in the presence of 25 µM 4-HNE. Depicted is a bar graph showing the total neurite length (µM) of cortical neurons treated with mock or 1 nM, 10 nM, 100 nM, 1 µM, or 10 µM midi-GAGR in the presence of 25 µM 4-HNE (mean±SEM, n=40 cells. One way ANOVA, Bonferroni post hoc test, : p<0.05; **: p<0.0001).
Figure 13B:
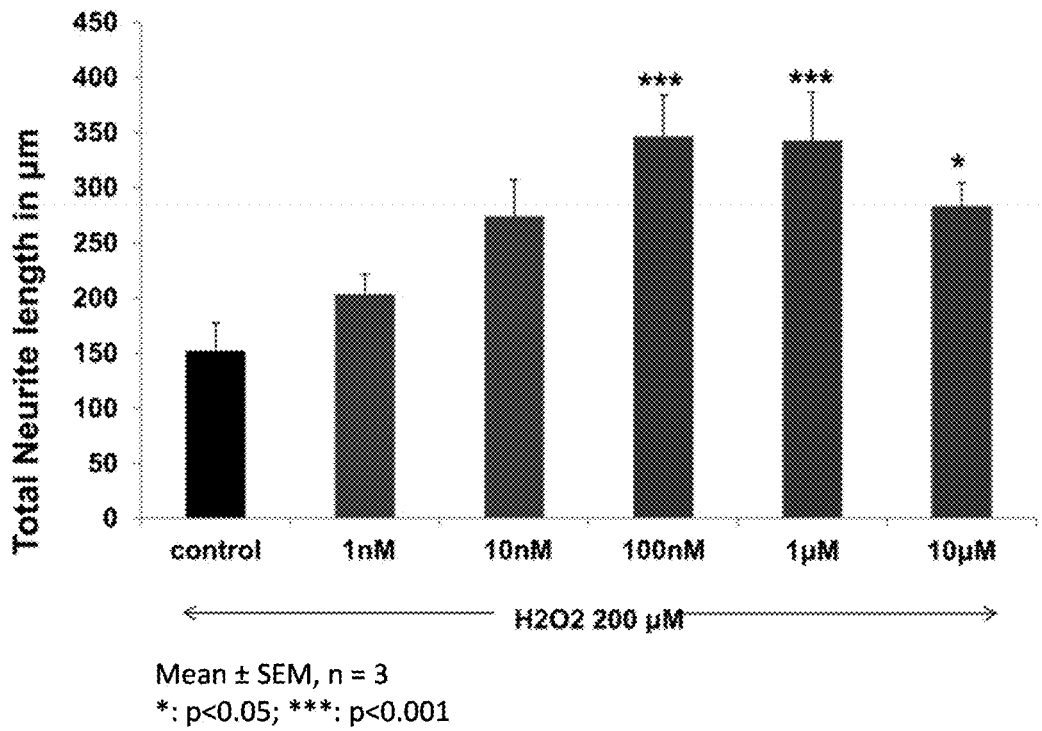
FIG. 13B: Midi-GAGR has a neurite outgrowth enhancing effect in the presence of 200 µM $H_2O_2$. Depicted is a bar graph showing the total neurite length (µM) of cortical neurons treated with mock or 1 nM, 10 nM, 100 nM, 1 µM, or 10 µM midi-GAGR in the presence of 200 µM $H_2O_2$ (mean±SEM, n=3 cells. One way ANOVA, Bonferroni post hoc test, *: p<0.05; ***: p<0.0001).

Rat embryonic cortical neurons were treated with mock (FIG. 11C), 1 μM HA-GAGR (high acyl gellan gum), 1 μM dextran, 100 μM ascorbate, or 1 μM midi-GAGR (FIG. 13A) for 2 days and then with 25 μM 4-hydroxynonenal (4-HNE), a lipid peroxide, for 1 day. After fixation, neurons were immunostained with anti-synaptophysin antibody (green) and rhodamine-phalloidin (actin: red). Scholl ring analysis was performed. Neurons pre-treated with mock, dextran, or ascorbate lost neuritis (neuritic atrophy) in the presence of 4-HNE. Conversely, neurons pretreated with 1 μM HA-GAGR prior to 25 μM 4-HNE formed neuritis, but less branched. 25 μM 4-HNE did not cause severe neuritic atrophy in neurons pre-treated with 1 μM midi-GAGR (FIG. 13B). This result indicates that midi-GAGR prevents neuritic atrophy caused by 4-HNE.

Figure 14A:
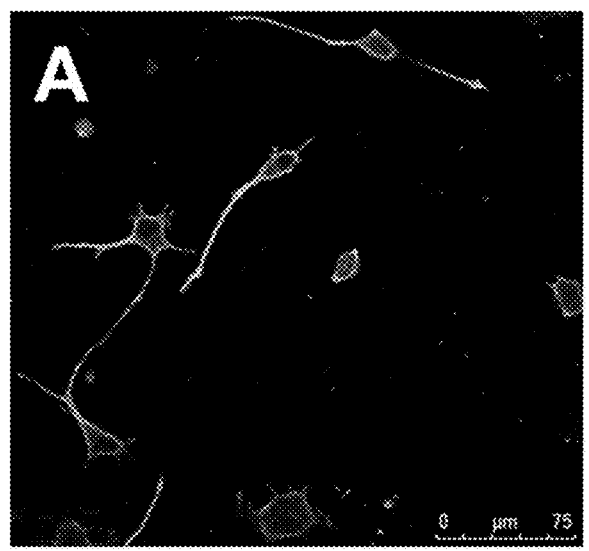
FIGS. 14A-14F: Midi-GAGR enhances neuritogenesis and actin filopodia formation in differentiated neuro2A (N2A) cells. N2A cells were starved in serum-free medium plus mock (FIG. 14A) or 1 µM midi-GAGR (FIG. 14B) for 3 days and stained by antibody to α-tubulin (green) and phalloidin (actin: red). The actin filopodia were observed in neurites of midi-GAGR-treated cells (FIG. 14D), but not in mock treated cells (FIG. 14C). After treatment with mock or midi-GAGR, cells were treated with mock (FIG. 14E) or 100 µM $H_2O_2$ (FIG. 14F) for one day and processed for immunocytochemistry as described above. (Scale bars in FIG. 14A-FIG. 14F=75 µm.)
Figure 14B:
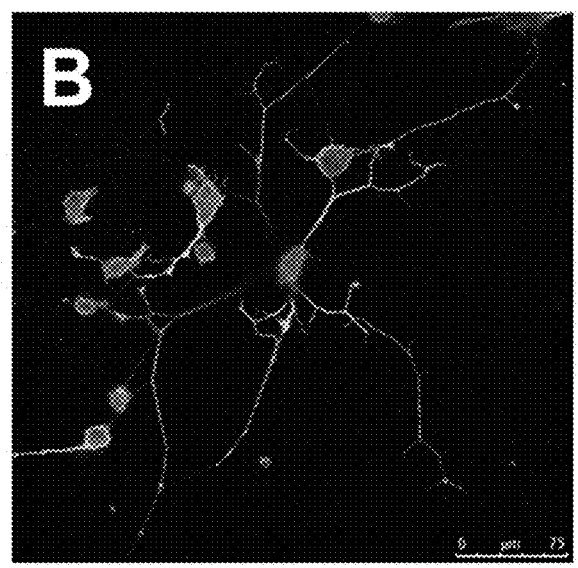
Figure 14C:
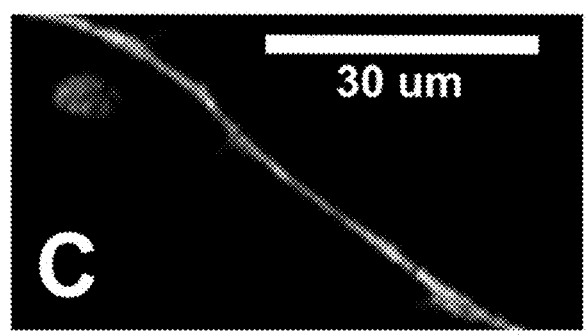
Figure 14D:

Midi-GAGR Enhances Neurito Genesis and Actin Filopodia Formation in Differentiated neuro2A (N2A) Cells N2A cells were starved in serum-free medium for 3 days with mock (FIG. 14A) or 1 μM midi-GAGR (FIG. 14B), fixed, and immunostained with anti-α-tubulin antibody (green) and rhodamine-phalloidin (actin: red). The number and total length of neurites in differentiated N2A cells were measured. The number and total length of neurites in midi-GAGR-treated N2A cells were ~1.7 fold higher than mock-treated cells. midi-GAGR also increased formation of actin filopodia along neurites (FIG. 14D) while mock did not (FIG. 14C).

Figure 14E:
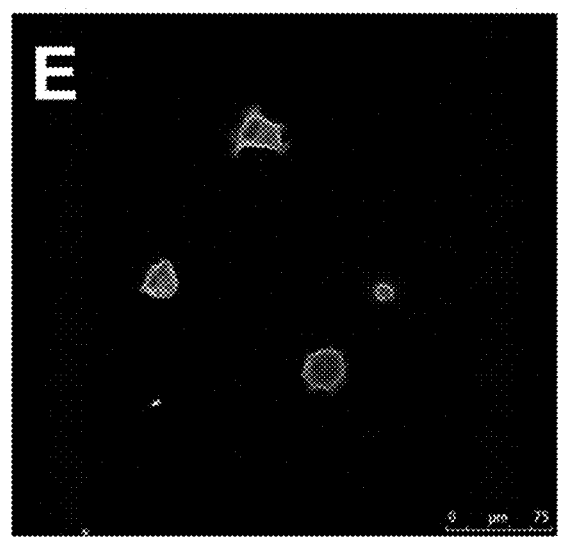
Figure 14F:
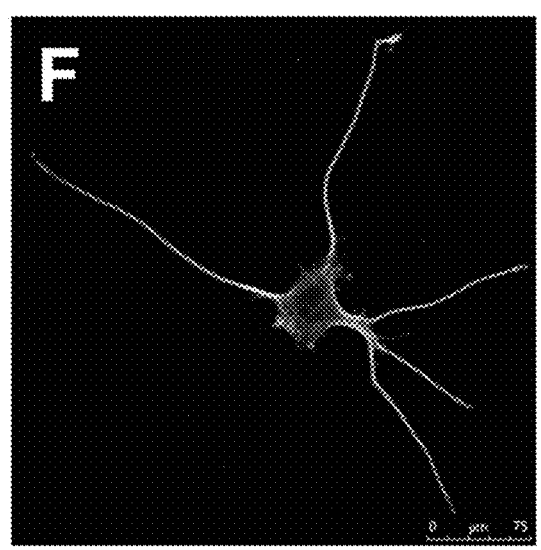

Following differentiation for 3 days with mock or 1 μM midi-GAGR, N2A cells were added with 10% FBS plus mock (FIG. 14E), 4-HNE (25 or 50 μM) or $H_2O_2$ (100 or 200 μM) (FIG. 14F: 200 μM $H_2O_2$) for 1 day. Cells were then fixed and immunostained with anti-α-tubulin antibody (green) and phalloidin (actin: red). The total neurite lengths in N2A cells were measured using Metamorph.

Figure 15A:
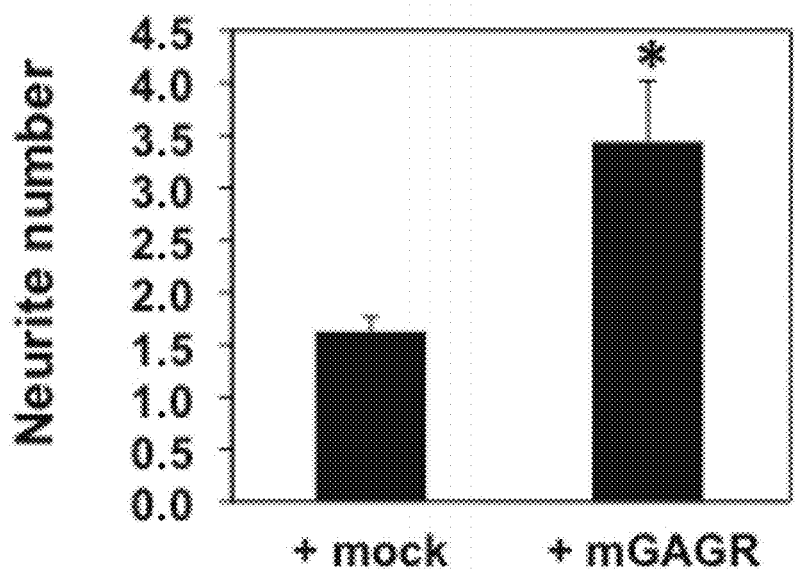
FIG. 15A: Midi-GAGR treated N2A cells form neurites in the presence of 25 µM 4-HNE and 200 µM $H_2O_2$. Depicted is a bar graph showing the numbers of neurites in N2A cells starved in serum-free-medium plus mock or 1 µM midi-GAGR for 3 days (n=90, 30 cells×3 independent experiments, mean±SEM, *=p<0.001).

Midi-GAGR-Treated N2A Cells Form Neurites in the Presence of 25 μM 4-HNE and 200 μM $H_2O_2$ Midi-GAGR treated N2A cells form neurites in the presence of 25 μM 4-HNE and 200 μM $H_2O_2$ (FIG. 15A). Depicted is a bar graph showing the numbers of neurites in N2A cells starved in serum-free-medium plus mock or 1 μM midi-GAGR for 3 days (n=90, 30 cells×3 independent experiments, Mean±SEM, *=$p<0.001$).

Figure 15B:
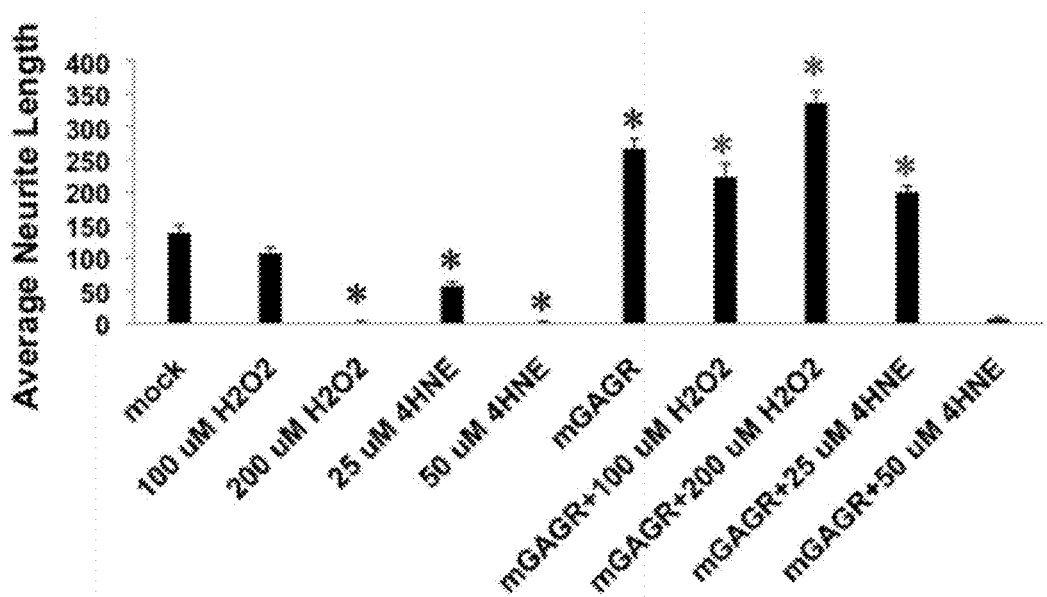
FIG. 15B: Midi-GAGR treated N2A cells form neurites in the presence of 25 µM 4-HNE and 200 µM $H_2O_2$. Depicted is a bar graph showing the average total neurite lengths of N2A cells starved in serum-free medium plus mock or 1 µM midi-GAGR for 3 days and then treated with mock, 100 or 200 µM $H_2O_2$, or 25 or 50 µM 4-HNE (n=90, 30 cells×3 independent experiments, mean±SEM, * (blue star) =p<0.001 compared to mock, * (red star)=p<0.001 compared to treatment with free radicals minus midi-GAGR.

Midi-GAGR treated 4-HNE cells form neurites in the presence of 25 μM 4-HNE and 200 μM $H_2O_2$ (FIG. 15B).

Depicted is a bar graph showing the average total neurite lengths of N2A cells starved in serum-free medium plus mock or 1 μM midi-GAGR for 3 days and then treated with mock, 100 or 200 μM $H_2O_2$, or 25 or 50 μM 4-HNE (n=90, 30 cells×3 independent experiments, mean±SEM, * (blue star)=p<0.001 compared to mock, * (red star)=p<0.001 compared to treatment with free radicals minus midi-GAGR).

The average total neurite length in mock-treated cells was decreased to ~50% of mock treatment by 4-HNE (25 μM) and to ~1% or mock by $H_2O_2$ (200 μM) while cells pre-treated with 1 μM midi-GAGR maintained their neurites in the presence of 25 μM 4-HNE and 200 μM $H_2O_2$ (FIG. 15B). These data indicate that midi-GAGR prevents neurite atrophy caused by 4-HNE and $H_2O_2$.

Figure 16:
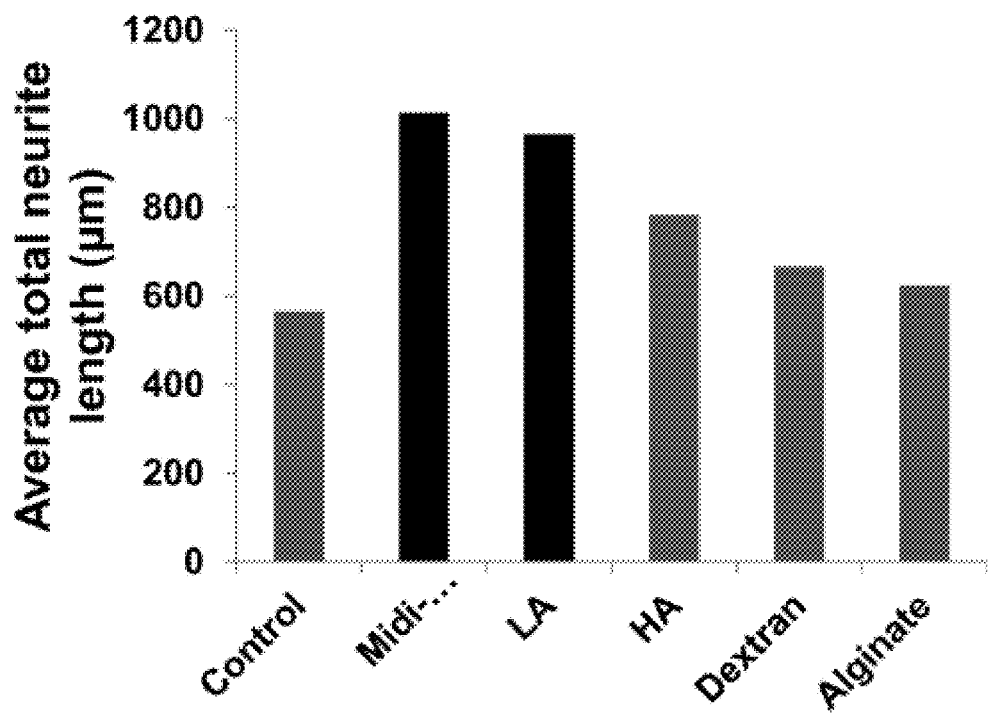
FIG. 16: Midi-GAGR enhances total neurite length of primary cortical neurons. Depicted is a bar graph showing the average total neurite length (µM) of primary cortical neurons treated with mock or midi-GAGR, low acyl gellan gum (LA), high acyl gellan gum (HA), dextran, or alginate (mean±SEM).

Midi-GAGR enhances total neurite length of primary cortical neurons (FIG. 16). Midi-GAGR enhances total neurite length of primary cortical neurons. Depicted is a bar graph showing the average total neurite length (μM) of primary cortical neurons treated with mock or midi-GAGR, low acyl gellan gum (LA), high acyl gellan gum (HA), dextran, or alginate (mean±SEM).

Midi-GAGR Penetrates an In Vitro BBB Layer

Figure 17:
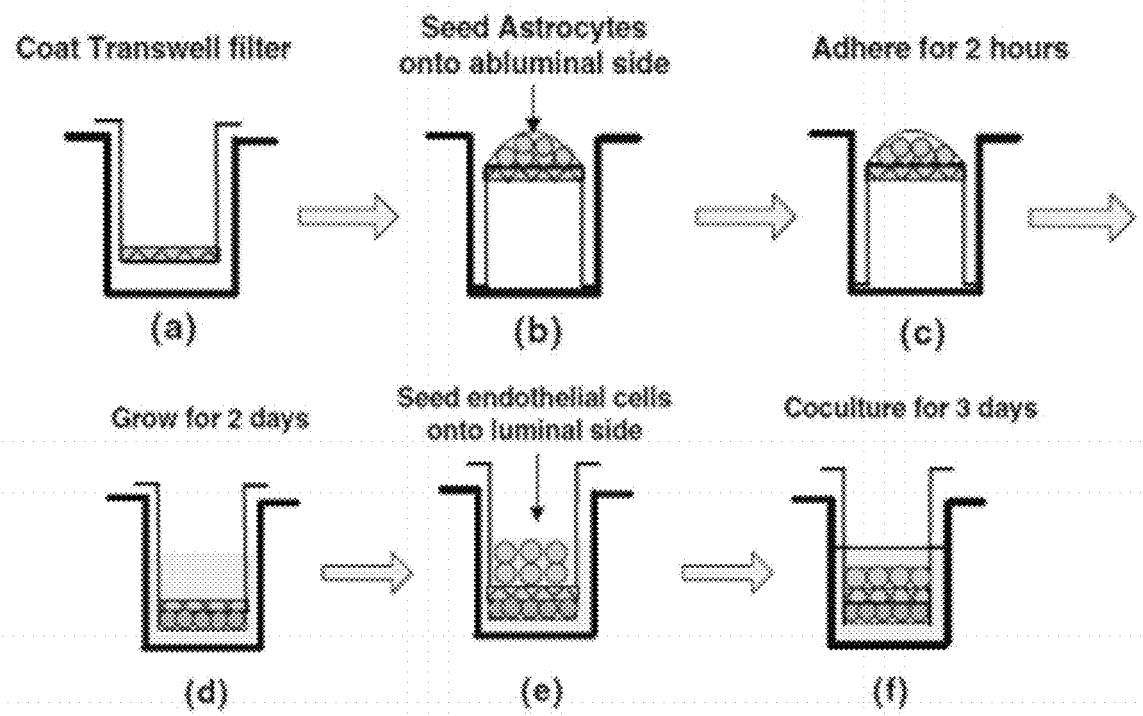
FIG. 17: In vitro blood-brain barrier (BBB) filter system. Depicted is a schematic showing the generation of an in vitro BBB consisting of bEND3 cells and astrocytes.
Figure 18:
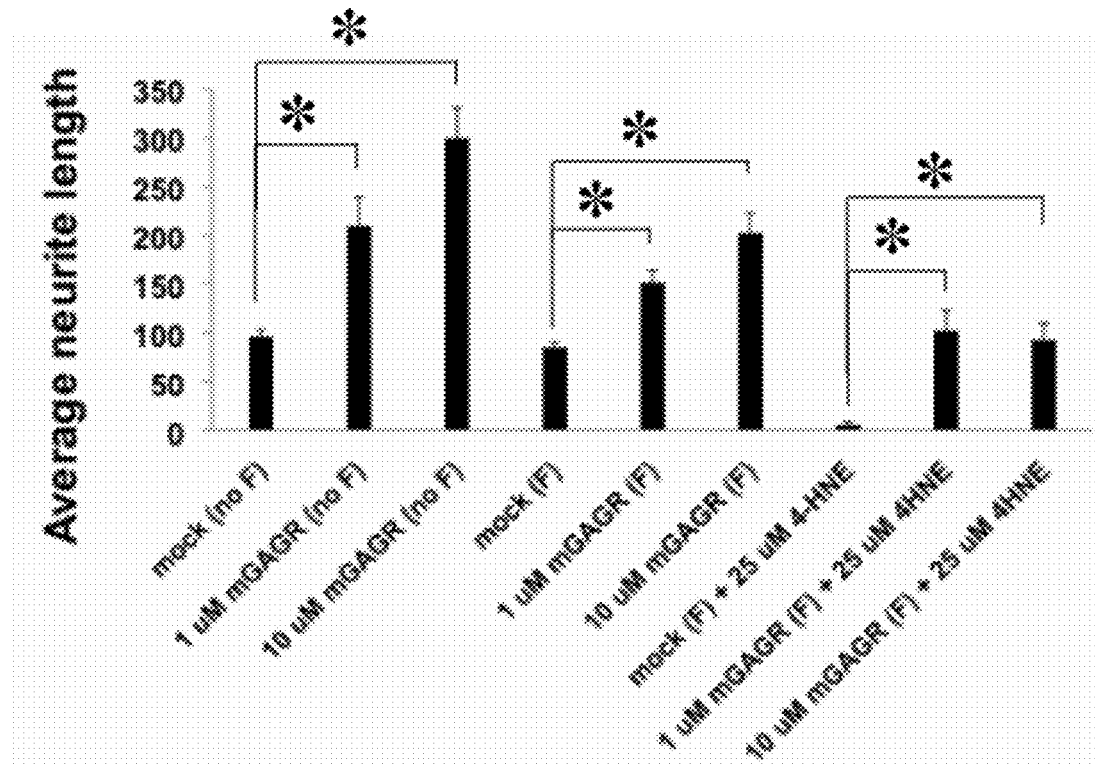
FIG. 18: Midi-GAGR penetrates an in vitro blood-brain barrier (BBB). Depicted is a bar graph showing the average total neurite length of N2A cells starved for 3 days in serum-free medium without (no F) or under the in vitro BBB filter system (F) on which mock or 1 or 10 µM midi-GAGR was added and then treated with mock or 25 µM 4-HNE (n=60, 30 cells×2 independent experiments, mean±SEM, *=p<0.001).

An in vitro blood-brain barrier (BBB) filter system was generated that consisted of bEND3 cells and astrocytes, as shown in the schematic illustration in FIG. 17. The filter system was placed on the top of each well of a 24-well plate, under which N2A cells were seeded on coverslips and incubated in serum-free DMEM. Mock, 1 or 10 μM midi-GAGR (mGAGR) was injected onto the top of the filter system. After 3 days differentiation, the filter systems were removed and N2A cells were treated with mock or 25 μM 4-HNE for 1 day. N2A cells that were under the filters into which 1 or 10 μM midi-GAGR was injected showed longer neurites that those injected with mock (FIG. 18). N2A cells that were under the filters into which 1 or 10 μM midi-GAGR was injected from long neurites even in the presence of 25 μM 4-HNE while cells injected with mock did not. This shows that that midi-GAGR can penetrate the in vitro BBB filter system.

Midi-GAGR Binds to NCAM-180

A midi-GAGR-epoxy-sepharose 6B column (GE Healthcare Biosciences, Pittsburgh, Pa.) was used to purify midi-GAGR-interacting protein(s) from the plasma membrane fraction of mouse brain synaptosomes. Multiple purification experiments yielded the same result, showing the presence of a ~180 kD protein only in the eluate from midi-GAGR beads. Mass spectrometry analysis showed that the 180 kD protein was NCAM-180. Activation of NCAM and FGFR induces MAPK pathways, resulting in activation of CREB. midi-GAGR thus exerts its neurotrophic effect via its interaction with NCAM-180.

Figure 19:
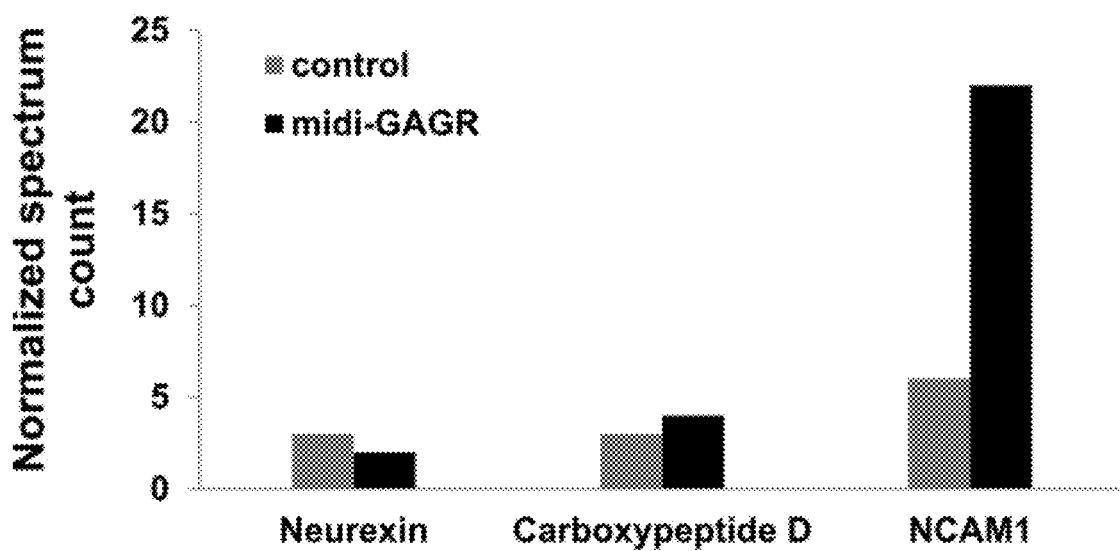
FIG. 19: Midi-GAGR binds to NCAM1. Depicted is a bar graph showing the normalized spectrum count for mock (control) or midi-GAGR binding to neurexin, carboxypeptide D, or NCAM1. Data is the result of two independent experiments.
Figure 20A:
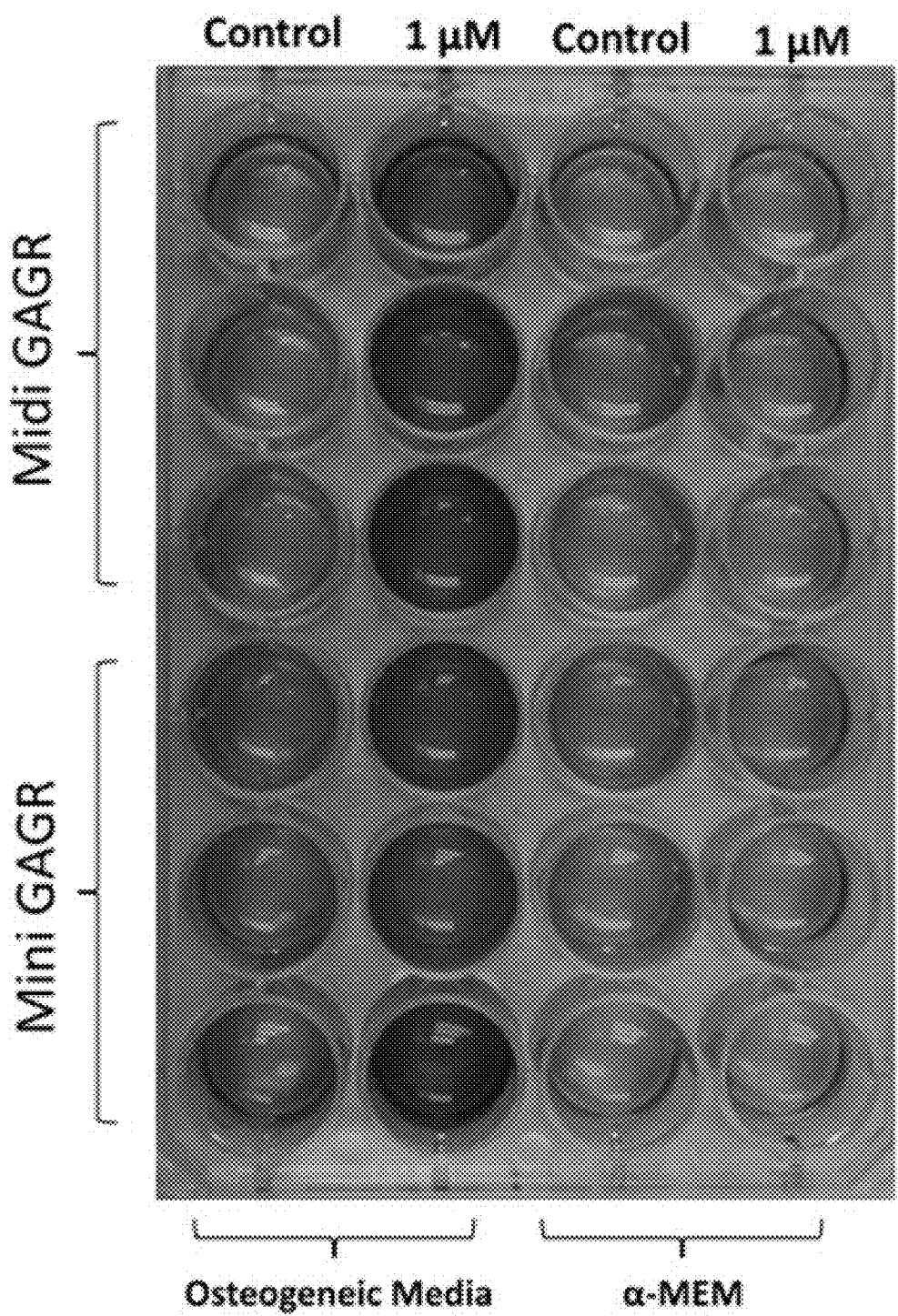
FIG. 20A: Mini- and midi-GAGR enhance osteogenesis of adult mesenchymal stem cells. Human bone marrow-derived mesenchymal stem cells were cultured in osteogenic media and α MEM media on 24-well plates for 14 day. Cells were treated with control, 1 μM mini-GAGR or 1 μM midi-GAGR every two days.
Figure 20B:
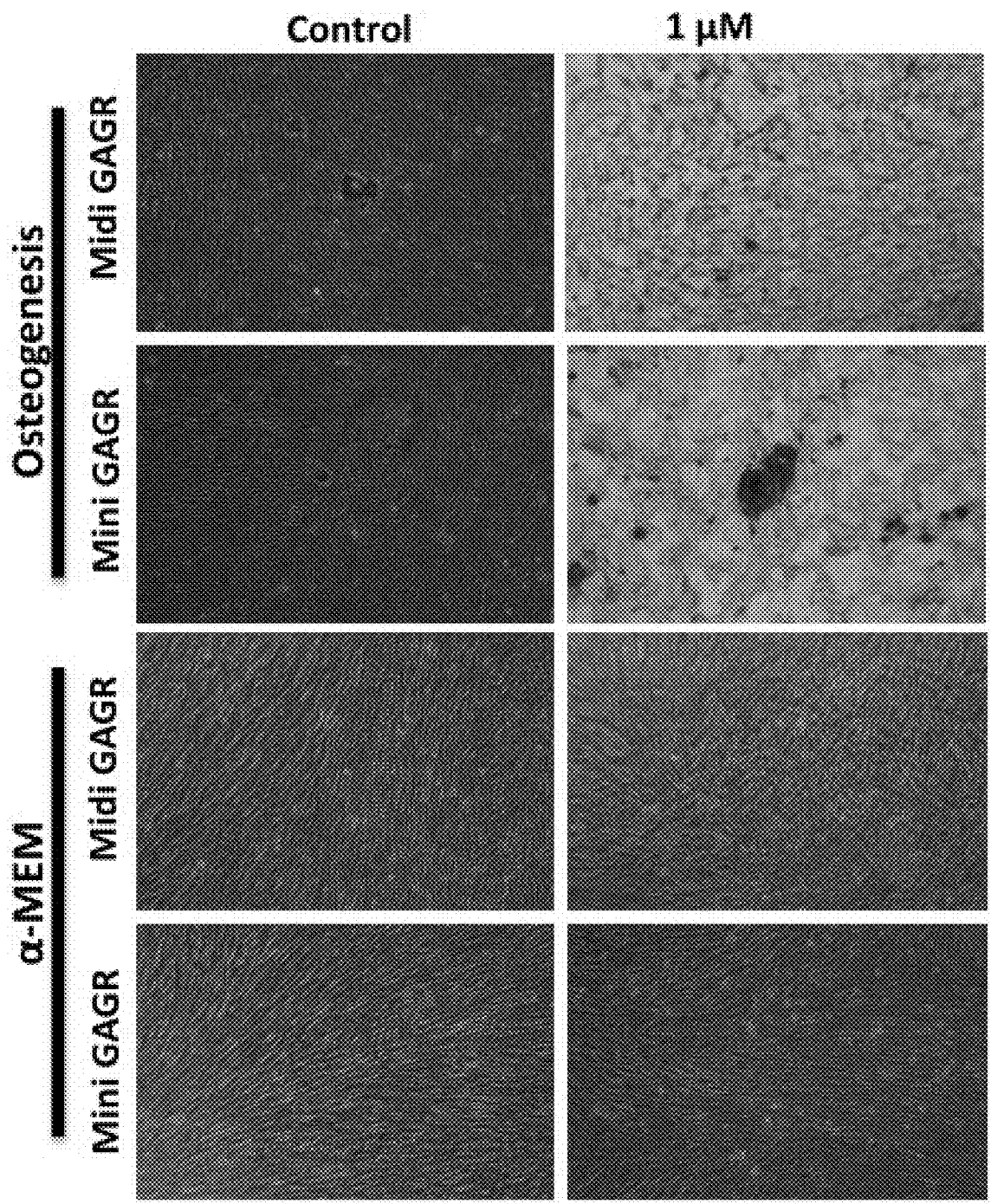
FIG. 20B: Mini- and midi-GAGR enhance osteogenesis of adult mesenchymal stem cells. Human bone marrow-derived mesenchymal stem cells were cultured in osteogenic media and α MEM media on 24-well plates for 14 day. Cells were treated with control, 1 μM mini-GAGR or 1 μM midi-GAGR every two days. After 14 days, cells were stained with Alizarin S and photographed using a light phase microscope.
Figure 21A:
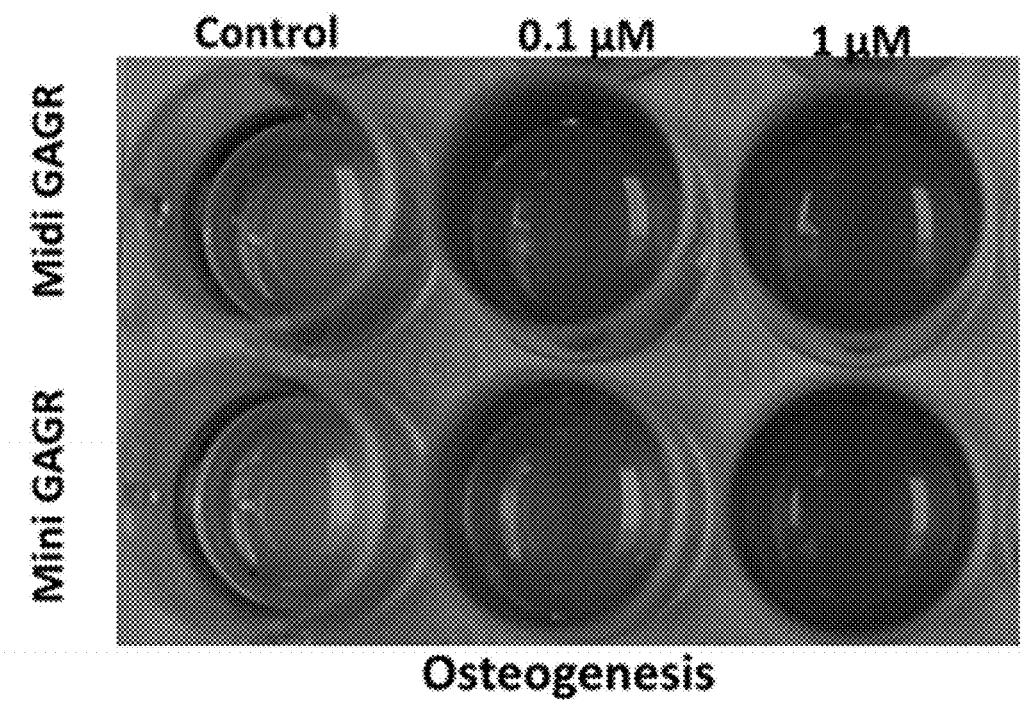
FIGS. 21A-21B: Mini- and midi-GAGR enhance osteogenesis of adult mesenchymal stem cells. Human bone marrow-derived mesenchymal stem cells were cultured in osteogenic media and α MEM media on 24-well plates for 14 day. Cells were treated with control, 0.1 μM mini- or midi-GAGR, or 1 μM mini- or midi-GAGR (FIG. 21A). After 14 days, cells were stained with Alizarin S and photographed using a light phase microscope (FIG. 21B).
Figure 21B:
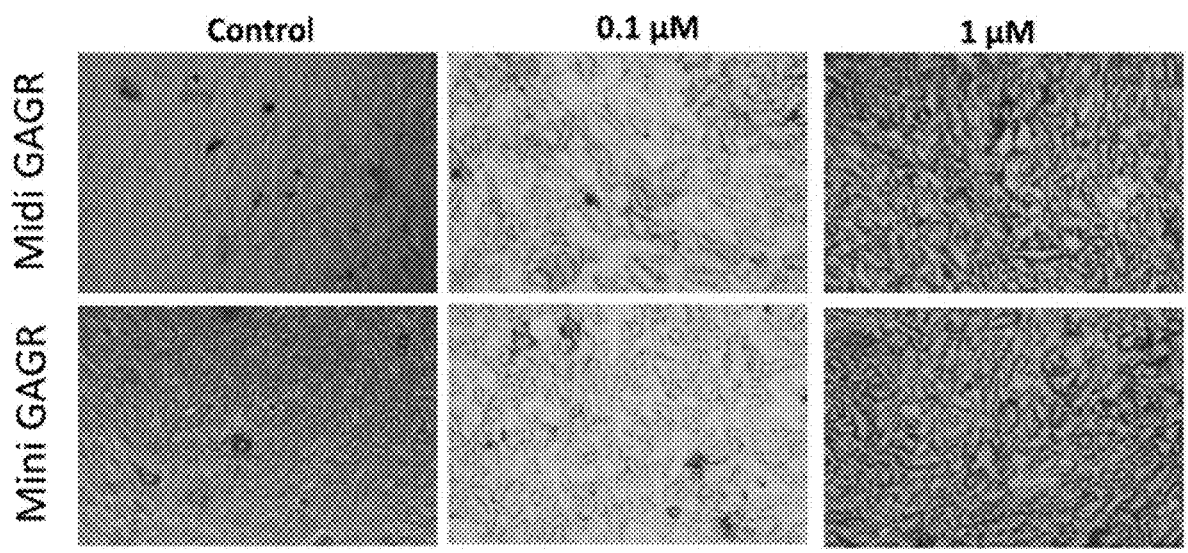

FIG. 19 shows that Midi-GAGR binds to NCAM1. Depicted is a bar graph showing the normalized spectrum count for mock (control) or midi-GAGR binding to neurexin, carboxypeptide D or NCAM1. Data is the result of two independent experiments.

Example 3

Enhancement of Osteogenesis of Adult Mesenchymal Stem Cells by Mini- and Midi-GAGR Human bone marrow-derived mesenchymal stem cells were cultured in either minimum osteogenic media or α MEM media on 24 well plates for 14 days. Cells were treated with control, 0.1 μM mini-GAGR, 1.0 μM mini-GAGR, 0.1 μM midi-GAGR, or 1.0 μM midi-GAGR every two days. After 14 days, cells were stained with Alizarin S and imaged using a light phase microscope.

Both mini- and midi-GAGR enhanced bone cell formation from human adult mesenchymal stem cells in the minimum osteogenic medium at very low concentrations (0.1 μM and 1.0 μM) (FIGS. 20A-20B and FIGS. 21A-21B) mini- and midi-GAGR enhanced bone cell formation ~500 fold compared to control minimum osteogenic media alone. Neither mini- nor midi-GAGR induced or enhanced osteogenesis in α MEM (non-osteogenic condition) (FIGS. 20A-20B and FIGS. 21A-21B).

Both mini- and midi-GAGR enhanced bone cell formation from adult mesenchymal stem cells in the osteogenic micro-environment found within bone. The osteogenic effect of mini- and midi-GAGR is limited to bone, and has no osteogenic effect in other intra-body regions.

Neither mini- nor midi-GAGR enhanced the expansion of stem cells, which excludes the possible implication of tumorigenesis of stem cells by mini- and/or midi-GAGR, a major setback for stem-cell based therapeutic approaches.

Example 4

BBB-Permeable, Neuroprotective and Neurotrophic Polysaccharide, Midi-GAGR

Materials and Methods

In order to increase water solubility and diffuse-ability, LA-GAGR was cleaved into smaller sizes by enzymatic digestion (α[1→3] glycosidase) for 24, 48, and 72 h. The MWs of its cleavage products were determined using Parallel Plate Rheometer that measures shear storage modulus and loss modulus and yields the viscosity profile of polysaccharides. From the viscosity-storage modulus profiles, the MW distributions of the cleavage products were determined using RheoAnalyzer program. The validity of the RheoAnalyzer program was verified by running polystyrene standard (NBS 706) on the Parallel Plate Rheometer and determining MW from the viscosity profile. The average MW of LA-GAGR was ~99,639 g/mole. The MWs of 24-h, 48-h, and 72-h cleavage products were ~30,245 g/mole, ~4,775 g/mole, and ~718 g/mole, respectively. The average MW of ~4,775 g/mole (named 'midi-GAGR') is equivalent to six repeating units and that of ~718 g/mole (named 'mini-GAGR') is to one repeating unit. Two small-size LA-GAGR products, midi-GAGR and mini-GAGR, were chosen for further examination regarding their neuroprotective effect.

Embryos (at the embryonic day of 17 [E17]) from female pregnant mice (BALB/C, Charles River Laboratories International Inc., Wilmington, Mass.) and female pregnant rats (E17, Sprague Dawley [SD], bred-in-house) were used to isolate primary cortical neurons for in vitro primary culturing. Adult female SD rats (12-16 weeks old, bred-in-house) were used for in vivo studies to examine the BBB-permeability and neurotrophic effect of midi-GAGR. 12-month-old 3×Tg-AD mice (female, B6; 129-Psen1tm1Mpm Tg [APPSwe, tauP301L] 1Lfa/Mmjax, Jackson Laboratory, Bar Harbor, Me.) were used for the studies to examine the effects of midi-GAGR on neurotrophic and neurodegenerative markers in 3×Tg-AD mouse brains. Animals were housed at room temperature under a 12-h light/dark cycle. Food and water were provided ad libitum. All experiments were performed during the light phase (7 am-7 pm). All the procedures of animal use described in this study were approved by the Institutional Animal Care and Use Committee (IACUC) of University of Toledo College of Medicine and Life Science in accordance with National Institutes of Health guidelines.

Antibodies

Antibodies to FGFR1 (SAB4300488), neurofilament 200 (NF200, N4142), and α-tubulin (T9026), synaptophysin (S5768), and βIII-tubulin (T2200) were purchased from Sigma (St. Louis, Mo.). Antibodies to PSD95 (sc-32290), pCREB (P-Ser133, sc-7978), CREB (sc-377154), glyceraldehyde-3-phosphate dehydrogenase (GAPDH, sc-32233), and growth associated protein 43 (GAP-43, sc-17790) were purchased from Santa Cruz Biotechnology, Inc. (Santa Cruz, Calif.). Antibody to PHF-tau (P-Ser202, AT8, MN1020B) was purchased from Thermo Scientific (Rockford, Ill.). Antibodies to Iba1 (ab5076) and pCREB (P-Ser133, ab30651) were purchased from Abcam Inc. (Cambridge, Mass.). Antibody to tau (610672) was purchased from BD Transduction Laboratories (Lexington, Ky.).

Hydrolysis of Low Acyl Gellan Gum 1 mL of 1% salicin solution (1 g salicin [Sigma] in 100 mL of 0.1 M acetate buffer [pH 5]) was pre-warmed at 37° C. for 6-8 minutes and mixed with 2 mg of α(1→3)-glucosidase (Sigma) to make the enzyme solution for the hydrolysis of low acyl gellan gum (LA-GAGR, CPKelco Co. [Atlanta, Ga.]). The enzyme solution was diluted to 0.1 mg/mL before use. 0.48 g of LA-GAGR was dissolved in 80 mL of the acetate/salicin solution. 8 mL of LA-GAGR solution was mixed with 2 mL of the enzyme solution in 15 mL polypropylene comical tubes and incubated at 37° C. (80 rpm) for 24, 48, or 72 h for the enzymatic digestion of LA-GAGR. Enzyme reaction was stopped by incubation in a hot water bath for 5 min and dried in a vacuum dryer (−60 cm Hg gauge) at 70° C. Dried gel pellet was then washed extensively in de-ionized water by stirring for 48 h (fresh water replaced every 12 h) to wash off salts and enzyme from the pellet and processed for viscosity measurement using a parallel plate rheometer (PPR, Rheometrics, Inc., Piscataway, N.J.) equipped with rheometer software, TA Orchestrator (TA Instrument, Inc., New Castle, Del.). From the viscosity-storage modulus profiles, the MW distributions of the cleavage products were determined using the RheoAnalyzer program (TomCoat Oy, Inc., Finland). The pellet was dissolved in 100 mL de-ionized water, autoclaved at 120° C. for 45 min, aliquoted, and kept at −80° C. until use.

Drug Treatment of Neuro2A (N2A) Cells

N2A cells (passage 7-10 [ATCC® CCL-131™]) were sparsely seeded on coverslips in Dulbecco's modified Eagle's medium (DMEM, Life Technologies, Grand Island, N.Y.) containing 10% heat-inactivated fetal bovine serum (FBS), 5 g/L D-glucose, 110 mg/L sodium pyruvate, and 1×Pen Strep (Life Technologies) and incubated at 37° C. in a humidified 5% $CO_2$ incubator for 48 h. Then, serum-containing medium was replaced with serum-free medium containing vehicle ($H_2O$) or different concentrations of midi-GAGR (0.001, 0.01, 0.1, 1, and 10 μM) and incubated for 3 days prior to immunocytochemistry using anti-α-tubulin antibody followed by secondary Alexa$_{488nm}$ antibody (Life Technologies). Coverslips were then mounted on glass slides using Fluoromount G (Fisher Scientific, Pittsburgh, Pa.). The images of cells were taken using a TCS SP5 multi-photon laser scanning confocal microscope (Leica Microsystems, Bannockburn, Ill.). The confocal microscope is equipped with conventional solid state, a ti-sapphire tunable multi-photon laser (Coherent, Santa Clara, Calif.), and acousto optical beam splitter AOBS. Images were taken with either 40× or 20×Zeiss alpha plan fluor oil objective (1.4 NA). Cells having the neurite length longer than 2 times the diameter of cell body were chosen for image analysis. To examine the protective effect of midi-GAGR against oxidative stress-induced neurite atrophy, differentiated N2A cells were pre-treated with midi-GAGR (0, 0.001, 0.01, 0.1, 1, and 10 μM) and then with either 4-hydroxynonenal (4HNE) (Cayman Chemical, Ann Arbor, Mich.) or $H_2O_2$ (Sigma). First, the toxic dose ranges of 4HNE and $H_2O_2$ that cause neurite atrophy were determined by treating differentiated N2A cells with 0, 1, 5, 10, or 25 μM of 4HNE for 48 h or 0, 1, 10, 50, 100, or 200 μM of $H_2O_2$ for 24 h. Then, the doses that showed maximum inhibitory effects were used to treat differentiated N2A cells along with 0, 0.001, 0.01, 0.1, 1, and 10 μM of midi-GAGR. The total neurite lengths of N2A cells in different conditions were measured using 'Metamorph' software (Molecular Devices, Sunnyvale, Calif.) and used to calculate average total neurite lengths.

Drug Treatment of Primary Rodent Cortical Neurons

The protective effect of polysaccharides on primary cortical neurons from 4HNE, $H_2O_2$, and $Aβ_{42}$ peptide (Sigma) was examined using LIVE/DEAD® Viability/Cytotoxicity Assay Kit (Life Technologies). Female pregnant mice (BALB/C, E17, Charles River Laboratories International, Inc.) or female pregnant SD rats (E17, bred in house) were anesthetized and dissected to obtain 8-9 embryos per animal. Cortical neurons were isolated from embryonic brains and differentiated on poly-L-lysine-coated coverslips in B27/neurobasal medium. For drug treatment before free radical treatment, mouse cortical neurons (5 days in vitro [DIV5]) were treated with vehicle ($H_2O$), 1 μM of 5 kD dextran (Sigma), alginate (Sigma), midi-GAGR, 0.01 μM of high acyl gellan gum (HA-GAGR, CPKelco Co.), or 0.1 μM of LA-GAGR for 24 h and then treated with 10 μM 4HNE or 50 μM $H_2O_2$ for 24 h, or 2 μM $Aβ_{42}$ peptide for 48 h prior to viability/cytotoxicity assay. For drug co-treatment with free radicals, rat cortical neurons (DIV5) were treated with 1 μM of dextran, alginate, or midi-GAGR, 0.01 μM of HA-GAGR, or 0.1 μM of LA-GAGR along with either 10 μM 4HNE (24 h) or 2 μM $Aβ_{42}$ peptide (48 h). To examine the extent to which midi-GAGR-mediated neuroprotection depends on FGFR1, rat cortical neurons (E17, DIV5) were pre-treated with 4 μM SU5402 (Sigma) for 6 h and treated with 10 μM 4HNE and either vehicle or 1 μM midi-GAGR for 24 h prior to cell viability/cytotoxicity assay. As controls, neurons were treated with SU5402, midi-GAGR, 4HNE, 4HNE plus midi-GAGR, or SU5402 plus midi-GAGR.

For cell viability/cytotoxicity measurement, neurons on glass coverslips were incubated in 1×PBS containing 2 μM calcein AM (live cells: green) and 4 μM ethidium homodimer-1 (dead cells: red) for 10 min at 37° C. Immediately thereafter, neurons were imaged by 10×objective using a fluorescence Olympus IX71 microscope (Olympus America Inc., Center Valley, Pa.) and, for the acquisition of high-quality images, using TCS SP5 multi-photon laser scanning confocal microscope.

Co-Culturing of Microglial Cells and Primary Rat Cortical Neurons

Microglial cell culture was prepared from the whole brain tissues (except of the cerebellum) of rat pups at postnatal day 3 (P3). Briefly, whole brain tissues except of the cerebellum were dissected and re-suspended in L-15 media on ice. Brain tissues were centrifuged at 1,000×g for 3 min at 4° C. After the supernatant over brain tissue pellet was removed, the pellet was re-suspended in fresh L-15 media, followed by mechanical digestion using pasteur pipette. After the digestion, the resuspension was filtered through cell strainer (pore diameter=70 μm). The flow-through was centrifuged at 1,000×g for 3 min at 4° C. Then, cell pellet was resuspended in DMEM media containing 10% FBS and 1× penicillin/streptomycin and plated at a high density in T75 culture flasks. The medium was exchanged with fresh medium every four days. After 8-10 days, culture flask caps were covered with parafilm to prevent gas exchange with environmental air. Flasks were then shaken in an orbital shaker at 220 rpm for 4 h at 37° C. Media was then collected into a conical tube and centrifuged at 800×g for 10 min. The resulting cell pellet (mostly microglial cells) was then resuspended in a neurobasal media containing B27 supplement and plated in filter insert (0.4-μm pore diameter) at a density of $2\times10^5$ cells. The filter inserts containing microglial cells were transferred to a 24 well plate containing rat cortical neuron cultures (DIV6) at the bottom of each well. Microglial cells were treated with either 2 μM $A\beta_{42}$ peptide or vehicle ($H_2O$) and neurons with either 1 μM midi-GAGR or vehicle ($H_2O$) for 48 h prior to live-dead assay. In addition, whether microglial cells penetrated the filter and fell down to neurons at the bottom of well or not were examined by staining the cells on coverslips at the bottom of well by staining the coverslips with anti-Iba1 antibody for immunocytochemistry and confocal microscopy.

Analysis of Neurite Outgrowth and pCREB in Primary Mouse Cortical Neurons

To analyze the effect of polysaccharides on neurite outgrowth, primary mouse cortical neurons were treated with vehicle ($H_2O$) or 1 μM of dextran, alginate, or midi-GAGR, 0.01 μM of HA-GAGR, or 0.1 μM of LA-GAGR for 2 days prior to immunocytochemistry using anti-α-tubulin antibody and secondary $Alexa_{488nm}$ antibody. An etched grid coverslip containing 200 numbered boxes was used to select neurons objectively for image acquisition and analysis. A total of 24 boxes were randomly selected per treatment group. All the neurons having total neurite length longer than 4 times of the diameter of neuron cell body were chosen for image analysis. The total length of the neurites of each neuron was measured using Metamorph and used to calculate average total neurite length. To examine the effect of polysaccharides on the phosphorylation (activation) of nuclear CREB, neurons were stained with anti-pCREB antibody (Abcam & Santa Cruz biotechnologies, 2nd antibody with $Alexa_{568nm}$), anti-α-tubulin antibody (Sigma, 2nd antibody with $Alexa_{488nm}$), and DAPI (Sigma) after two-day incubation with vehicle ($H_2O$) or 1 μM of dextran, alginate, or midi-GAGR, 0.01 μM of HA-GAGR, or 0.1 μM of LA-GAGR. Then, to identify midi-GAGR-induced signaling pathway that induces CREB phosphorylation, primary mouse cortical neurons were pre-treated with the inhibitors of FGFR1 (SU5402 [Santa Cruz Biotechnologies], 4 μM), PKC (staurosporine [Sigma], 3 nM), MEK (U0126 [Sigma], 10 μM), PI3K (LY294002 [Sigma], 20 μM), CaMKII (KN-62 [Calbiochem, Billerica, Mass.], 10 μM), or FAK (PF-573228 [Sigma], 1 μM) for 6 h and then with 1 μM midi-GAGR for 48 h prior to the staining of pCREB and α-tubulin. The images of neurons on coverslips were taken by confocal microscopy at the same gain (850), offset (−0.01), and exposure time (2 sec). The intensity of the staining of nuclear pCREB was measured using Metamorph and used to calculate average intensity. In addition, the phosphorylation of CREB in the cytosols of mouse cortical neurons treated with polysaccharides were detected by immunoblotting. Primary mouse neurons were dissected from 16 mouse embryos (E17) and plated in the wells of 6-well plates ($1\times10^6$ cells/well), differentiated for 6 days, and treated with polysaccharides for 48 h. Then, neurons were harvested and lysed in 1% Igepal CA-630 (Sigma)-containing PMEE buffer plus protease and phosphatase inhibitor cocktails (Sigma) for protein extraction. Extracted proteins were separated in 4-12% NuPAGE Bis-Tris protein gels (Life Technologies) and transferred to nitrocellulose membrane (GE Healthcare Life Science, Pittsburgh, Pa.) using a semidry blotter (Hoefer, Inc., San Francisco, Calif.). The protein bands on blots recognized by anti-pCREB (Santa Cruz Biotechnologies) and anti-CREB antibodies were detected on Amersham Hyperfilm™ ECL films (GE Healthcare Life Science) using SuperSignal® West Pico Chemiluminescent Substrate (Thermo Scientific).

Examination of the In Vivo Neurotrophic Effect of Midi-GAGR

40 μL of 1 mM midi-GAGR or sterile $H_2O$ (vehicle) was administered intranasally into the nostrils (20 μL/nostril) of SD rats (4 rats per each) using a pipette. Animals were kept in anesthetized condition using 4% isoflurane and at supine position during administration to prevent the squirting-out of drug. Animals were sacrificed by decapitation at 6 h, 24 h, or 48 h after the administration. Whole brain was microdissected into the frontal cortex, hippocampus, and the rest of brain. Then, tissues were homogenized in the 2-fold volume of 1×PMEE buffer containing 1% Igepal CA-630 and protease inhibitor cocktail using a 2-mL Teflon homogenizer. The homogenization was then incubated on ice for 30 min at 4° C., followed by centrifugation at 14,500×g for 30 min. The supernatant was collected and its protein concentration was measured by Bradford assay. 20 μg of proteins was loaded onto each well of NuPage 4-11% Bis-Tris protein gels. Immunoblotting was performed using the antibodies to NF200, GAP-43, and GAPDH. The densities of protein bands were measured using Image J and normalized to that of the loading control, GAPDH. Normalized values were used to calculate average normalized band densities.

Examination of the Interaction of Midi-GAGR with FGFR1 in Brain Synaptosomal Plasma Membrane To examine whether midi-GAGR interacts with synaptosomal FGFR1 or not, an affinity chromatography using midi-GAGR-conjugated sepharose beads was performed. Either midi-GAGR or dextran were conjugated to epoxy-activated sepharose 6B that is a pre-activated medium that can be conjugated to the hydroxyl groups of carbohydrates. Briefly, 200 μL of 7.4 mM midi-GAGR or 5 kD dextran in $H_2O$ was mixed with 200 μL of epoxy-activated sepharose beads in a microtube and incubated on a rotator (16 h, 37° C.). The mixture was spun down at 1,000×g (10 min) to separate bead-bound polysaccharides from unbound. Unoccupied active sites on beads were blocked by incubation (4 h, 45° C.) in 1 M ethanolamine (pH 8). Then, beads were washed with three cycles of alternating pH solutions—0.1 M acetate buffer (pH 4) and 0.1 M Tris-HCl buffer (pH 8), both containing 0.5 M NaCl. The conjugation of polysaccharides to beads was confirmed by phenol-sulfuric acid colorimetry. Cerebral cortices were dissected from four female mice (BALB/C, 8 wks old) and homogenized with a hand grinder in 1 mL of PMEE homogenization buffer plus 1% Igepal CA-630 and protease inhibitors (PIs). The homogenate was centrifuged at 1,000×g (10 min) to remove nuclei and undisrupted cells. The supernatant was subjected to 5-6 strokes through 27G needle. Post-nuclear supernatant was centrifuged at 1,000×g (15 min). The supernatant was diluted to 1:2 with Igepal CA-630-free PMEE buffer (to make 0.5% Igepal CA-630) and stored at −80° C. until use. Then, the supernatant was incubated with 100 μL of either midi-GAGR-conjugated or dextran-conjugated beads. After 24-h incubation on a rotator at 4° C., the beads were washed three times with 0.5 mL of PMEE buffer to remove proteins that nonspecifically bind to beads. Then, the beads were boiled for protein elution in a SDS loading buffer. Eluted proteins were separated in a SDS-NuPAGE gel and processed for immunoblotting using FGFR1 antibody.

Examination of the Effects of Midi-GAGR on Neuronal Activity and Neurodegenerative Markers in 3×Tg AD Mice 12-week-old 3×Tg-AD mice (female, ~20 g, B6.Cg-Psen1tm1Mpm Tg [APPSwe, tauP301L]1Lfa/J) were used to examine the efficacy of midi-GAGR in restoring neuronal activity and reducing neurodegeneration in AD mouse brains. Three 3×Tg AD mice were intranasally administered with either sterile $H_2O$ (vehicle) or 7.4 mM midi-GAGR (40 μL total, 20 μL/nostril) every day for 14 days after 4% isoflurane anesthetization and then sacrificed by decapitation. Whole brain was micro-dissected to obtain the cortices and hippocampi. The tissues were homogenized in the 2-fold volume of 1×PMEE buffer containing 1% Igepal CA-630 plus phosphatase and protease inhibitor cocktail using a miniature cell grinder for 1.5 mL microtube. The homogenization was then incubated on a rotator for 30 min at 4° C., followed by centrifugation at 14,500×g for 30 min. The supernatant was collected and its protein concentration was measured by Bradford assay. 30 μg of proteins was loaded onto NuPage 4-11% Bis-Tris protein gels. Immunoblotting was performed using the antibodies to NF200, GAP-43, PSD95, synaptophysin, pCREB, CREB, p-tau (AT8), tau, and GAPDH. The densities of protein bands were measured using Image J and normalized to that of the loading control, GAPDH. Normalized values were used to calculate average normalized band densities.

Statistical Analysis

All cell culture experiments were replicated multiple times with different batches of cell cultures. Microscopic analysis was performed blindly by students. Statistical significance between two groups was calculated using unpaired student's t-test with a value of $p<0.05$ that was considered statistically significant. Multiple comparisons were performed using one-way ANOVA followed by Dunnett's or Bonferroni's multiple comparisons tests (GraphPad Prism software, La Jolla, Calif.).

Generation of Cleavage Products from LA-GAGR

LA-GAGR was cleaved into smaller sizes by enzymatic digestion ($\alpha(1\rightarrow3)$-glycosidase) for 24, 48, and 72 h. The MWs of LA-GAGR's cleavage products were determined using Parallel Plate Rheometer that measures shear storage modulus and loss modulus and yields the viscosity profile of polysaccharides. From the viscosity-storage modulus profiles, the MW distributions of the cleavage products were determined using RheoAnalyzer program. The validity of the RheoAnalyzer program was verified by running polystyrene standard (NBS 706) on the Parallel Plate Rheometer and determining MW from the viscosity profile.

The average MW of LA-GAGR was ~99,639 g/mole, which is close to the value reported by CPKelco Co. The MWs of 24-h, 48-h, and 72-h cleavage products were ~30,245 g/mole, ~4,775 g/mole, and ~718 g/mole, respectively. The average MW of ~4,775 g/mole (named 'midi-GAGR') is equivalent to six repeating units and that of ~718 g/mole (named 'mini-GAGR') is equivalent to one repeating unit.

Results for Example 4

Midi-GAGR Rescues Neurites from the Atrophy Caused by 4HNE and $H_2O_2$

Differentiated N2A cells were used to examine if midi-GAGR and mini-GAGR protect neurites from the oxidative insults of 4HNE and $H_2O_2$ as LA-GAGR does. The atrophic dose ranges of the radicals were determined by treating differentiated N2A cells with increasing concentrations of 4HNE and $H_2O_2$ for 48 h and 24 h, respectively. Treated cells were fixed, immunostained by anti-α-tubulin antibody, imaged by confocal microscopy, and examined regarding total neurite length. The average total neurite length of N2A cells was decreased in a dose-dependent manner in response to 4HNE and $H_2O_2$ to maximum extents at 25 μM 4HNE (FIG. 22B, FIG. 22D) and 200 μM $H_2O_2$ (FIG. 22C, FIG. 22E) compared to vehicle (FIG. 22A).

25 μM and 200 μM were the maximum doses of 4HNE and $H_2O_2$, respectively, that caused almost complete neurite atrophy in differentiated N2A cells. Differentiated N2A cells were treated with increasing concentrations of midi-GAGR prior to the treatment with either 25 μM 4HNE or 200 μM $H_2O_2$. Treatment with 0.1 and 1 μM midi-GAGR prior to 4HNE treatment rescued neurites up to ~70% of the control level (vehicle) (FIG. 22F, FIG. 22H).

Similarly, treatment with 0.1 and 1 μM midi-GAGR prior to $H_2O_2$ treatment rescued neurites up to ~100% of the control level (FIG. 22G, FIG. 22I). The protective effect of mini-GAGR was examined, but it was found that mini-GAGR was not as potent as midi-GAGR in protecting neurites from the free radicals. Therefore, midi-GAGR (which showed stronger neuroprotective effect against 4HNE and $H_2O_2$) was used in further experiments.

Midi-GAGR Reduces the Apoptosis of Rodent Cortical Neurons Caused by 4HNE, $H_2O_2$, and Amyloid β Peptide Midi-GAGR attenuated neurite atrophy caused by free reactive radicals. It is now shown herein that midi-GAGR protect neurons from the death caused by free radical insults. The extent to which midi-GAGR protects the primary culture of rodent cortical neurons from 4HNE and $H_2O_2$ was determined. In addition to the radicals, amyloid β peptide ($A\beta_{42}$) was also tested. $A\beta_{42}$ peptide is a major causative factor that causes oxidative stress and neuron death. Mouse cortical neurons (E17, DIV5) were treated with 10 μM 4HNE (24 h), 50 μM $H_2O_2$ (24 h), or 2 μM $A\beta_{42}$ peptide (48 h) after the treatment of the neurons with vehicle ($H_2O$), midi-GAGR (1 μM), dextran (1 μM), alginate (1 μM), LA-GAGR (0.1 μM), or HA-GAGR (0.01 μM) for 24 h. The concentrations of 4HNE, $H_2O_2$, and $A\beta_{42}$ peptide were chosen according to their patho-physiological concentrations. The concentrations of LA-GAGR and HA-GAGR were chosen because, within the same volume, the total numbers of sugar units in the polysaccharides at the concentrations are close to that of 1 μM midi-GAGR. The viability of neurons was assessed using LIVE/DEAD® Viability/Cytotoxicity Assay Kit in which membrane-permeant calcein AM is cleaved by esterase in live cells, thus yielding green fluorescence, and membrane-impermeant ethidium homodimer-1 stains the nucleic acids of plasma membrane-compromised cells with red fluorescence. The numbers of green (live) and red (dead) neurons in each condition were counted using Metamorph. Although the intensities of green fluorescent signals in neurons treated with either free radicals or $A\beta_{42}$ peptide were weak, the neurons were included in the counting. About 8-9% of vehicle-treated neurons died during the process of live/dead cell assay (FIGS. 23A-23F, FIGS. 24A-24C).

Figure 23D:
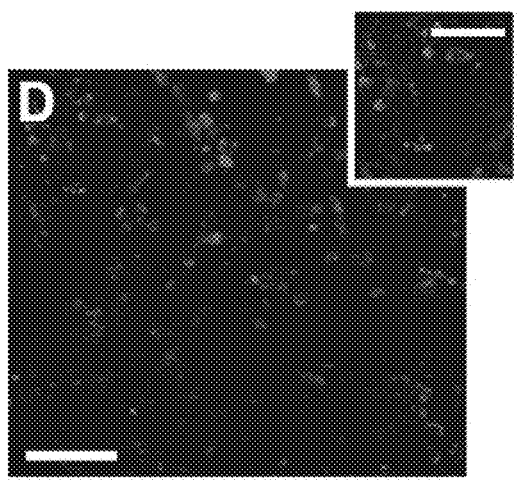
Figure 23E:
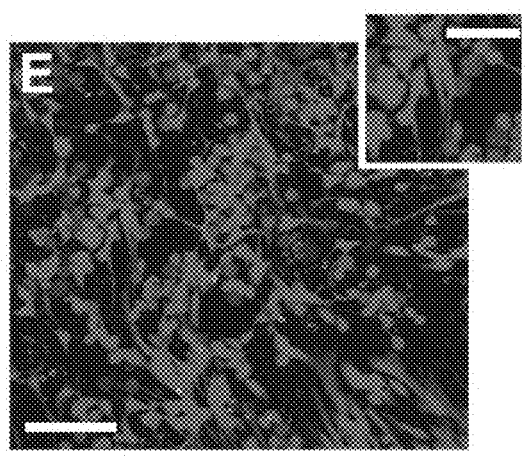
Figures 24A, 24B, 24C:
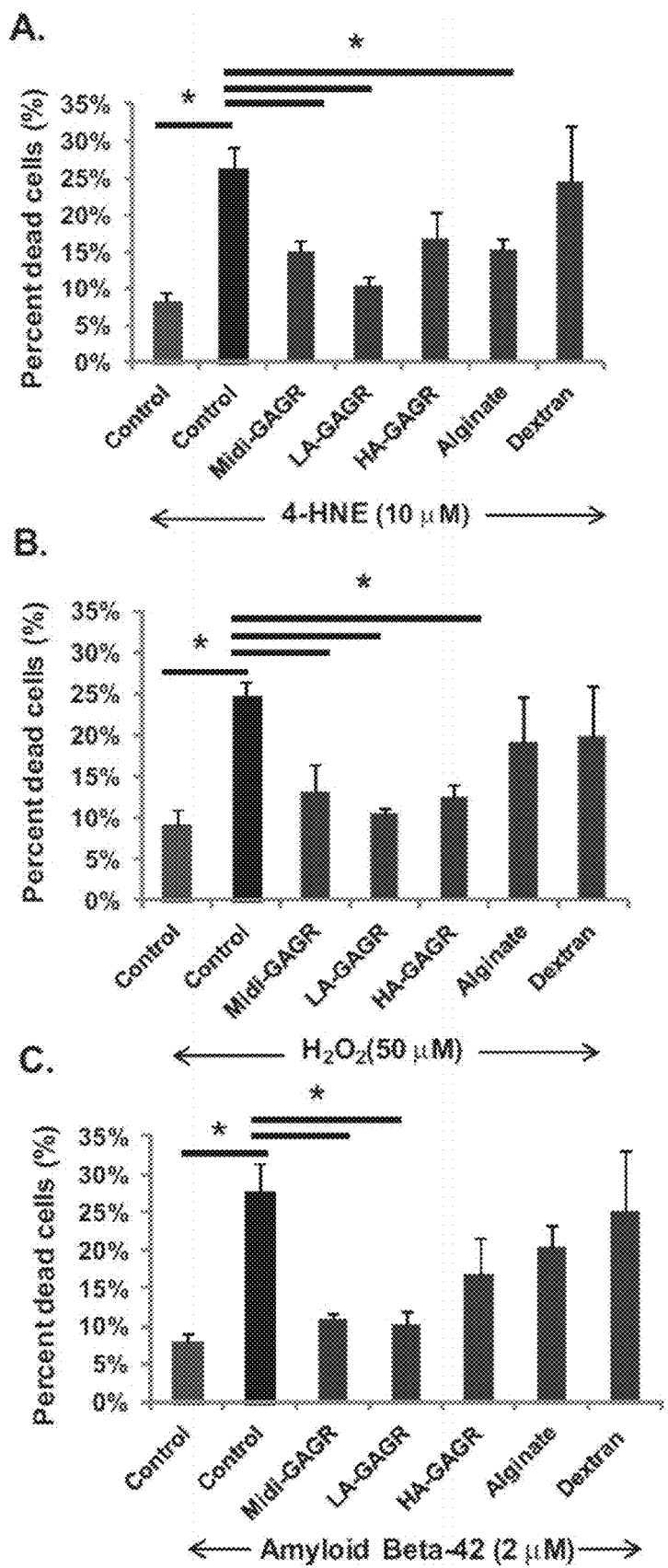
FIGS. 24A-24C: Quantification of neuron death in response to oxidative insults in the presence of different polysaccharides. The numbers of live and dead cells were counted using Metamorph software. Bar graphs represent the percents of dead cells after the pre-treatments with different polysaccharides followed by treatment with 4HNE (FIG. 24A), $H_2O_2$ (FIG. 24B), or $Aβ_{42}$ (FIG. 24C). Data represent mean±SEM of three independent experiments. For each experiment, at least, 1,000 cells per group were counted. *, $p<0.05$.

Upon exposure to 10 μM 4HNE, ~26% of mouse cortical neurons died (FIG. 23B, FIG. 24A) while pre-treatment with 1 μM midi-GAGR (FIG. 23C) and 0.1 μM LA-GAGR reduced neuron death to 14% and 10%, respectively (FIG. 24A). HA-GAGR and alginate also reduced the percent of neuron death caused by 4HNE while dextran did not (FIG.

24A). Exposure to 50 µM $H_2O_2$ caused neuron death in ~25% of cortical neurons that were pre-treated with vehicle (FIG. 23D, FIG. 24B). Pre-treatment with either alginate or dextran did not reduce $H_2O_2$-caused neuron death (FIG. 24B). Conversely, pre-treatment with midi-GAGR (FIG. 23E), LA-GAGR, or HA-GAGR reduced neuronal death to ~13% (FIG. 24B). These results show that midi-GAGR, LA-GAGR, and HA-GAGR protects rodent cortical neurons from both $H_2O_2$ and 4HNE while dextran and alginate cannot.

Figure 23F:
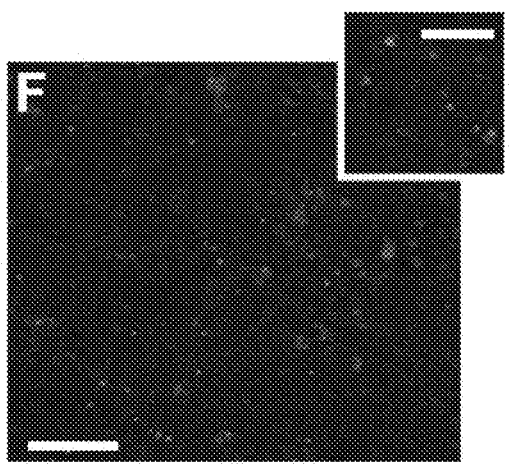
Figure 23G:
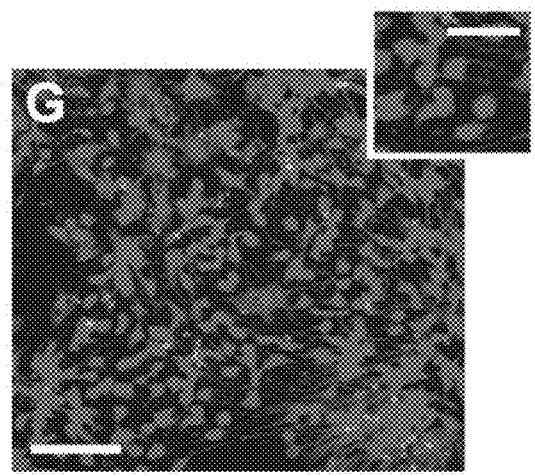

The extent to which midi-GAGR protects cortical neurons from $A\beta_{42}$ peptide was examined. Exposure to 2 µM $A\beta_{42}$ peptide caused the death of about 30% of neurons pre-treated with vehicle (FIG. 23F, FIG. 24C). Pre-treatment with HA-GAGR, alginate, or dextran did not decrease the percent of neuron death compared to pre-treatment with vehicle (FIG. 24C). Conversely, pre-treatment with either midi-GAGR or LA-GAGR reduced neuron death to ~10%, the control level (FIG. 23G, FIG. 24C). Thus, only midi-GAGR and LA-GAGR protects cortical neurons from $A\beta_{42}$ peptide, while other polysaccharides cannot.

Figure 25A:
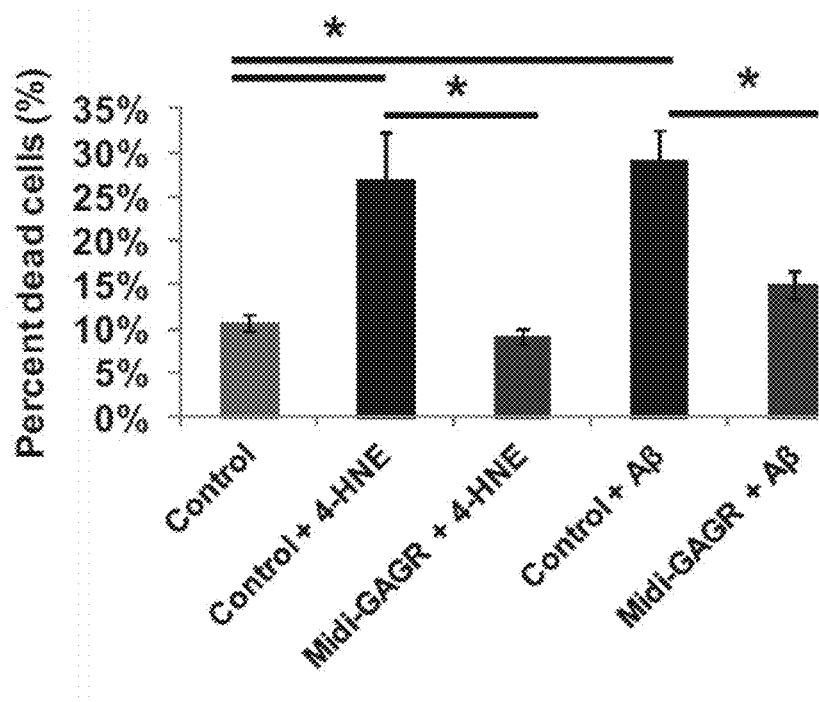
FIGS. 25A-25B: Midi-GAGR protects rodent cortical neurons from co-treated 4HNE, $Aβ_{42}$ peptide, and activated microglial cells.

Midi-GAGR Reduces the Apoptosis of Rodent Cortical Neurons from Co-Treated 4HNE or $A\beta_{42}$ Peptide It was determined whether midi-GAGR protects cortical neurons from co-treated 4HNE or $A\beta_{42}$ peptide. Rat cortical neurons (E17, DIV5) were treated with either 10 µM 4HNE (24 h) or 2 µM $A\beta_{42}$ peptide (48 h) and either vehicle or 1 µM midi-GAGR. Then, the viability of neurons was assessed using LIVE/DEAD® Viability/Cytotoxicity Assay Kit. Exposure to 10 µM 4HNE caused apoptosis in ~27% of vehicle-treated neurons while co-treatment with midi-GAGR reduced the percent of neuron death to ~9% (FIG. 25A). Treatment with 2 µM $A\beta_{42}$ peptide caused death in ~29% of vehicle-treated neurons, while co-treatment with midi-GAGR reduced the percent of neuron death to ~15% (FIG. 25A). These results show that midi-GAGR also protects rodent cortical neurons from co-treated 4HNE or $A\beta_{42}$ peptide.

Figure 25B:
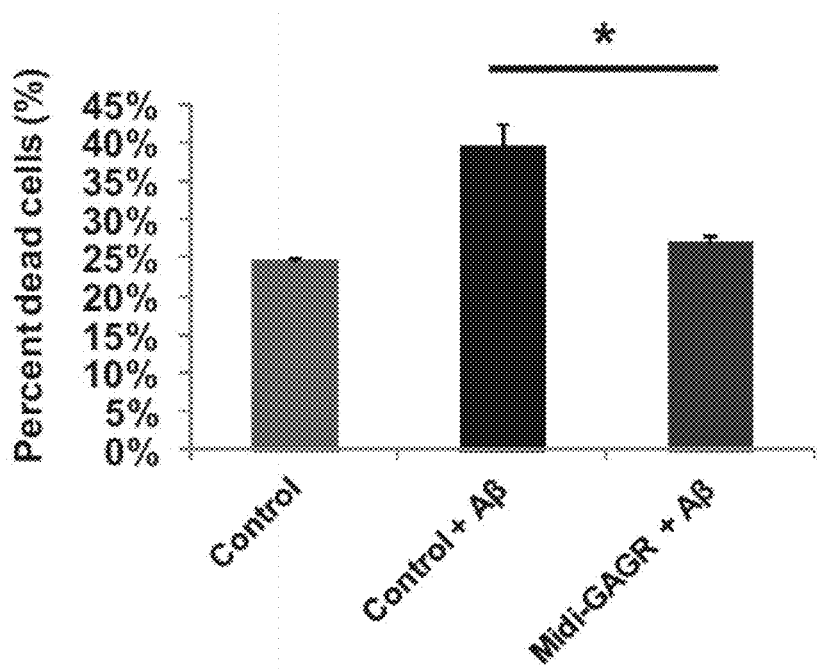

Midi-GAGR Protects Rodent Cortical Neurons from Microglial Cells Activated by $A\beta_{42}$ Peptide It was determined whether midi-GAGR protects primary rodent cortical neurons from microglia cells activated by $A\beta_{42}$ peptide. Microglial cells were isolated from rats on the postnatal day 1 and seeded in 0.4-µm-pore-size filter insert that fits into the well of 24-well plate. The filter inserts were transferred to a 24-well plate in which primary rat cortical neurons (E17) were cultured at the bottoms of wells for 6 days (DIV6). Then, microglia cells were treated with 2 µM $A\beta_{42}$ and neurons with either vehicle or 1 µM midi-GAGR. After 48 h, the viability of neurons was assessed using LIVE/DEAD Viability/Cytotoxicity Assay Kit. Around 25% of the neurons treated with vehicle died under untreated microglial cells (FIG. 25B). Upon treatment of microglial cells with $A\beta_{42}$ peptide, the percent of death in neurons treated with vehicle was increased to ~40%. Conversely, treatment of neurons with 1 µM midi-GAGR reduced death to ~27% that was close to the percent of dead neurons under untreated microglial cells (FIG. 25B). Thus, it is clear that midi-GAGR protects rodent cortical neurons from activated microglial cells.

Midi-GAGR Enhances Neurite Outgrowth in N2A Cells and Rodent Cortical Neurons

Figures 26A, 26B:
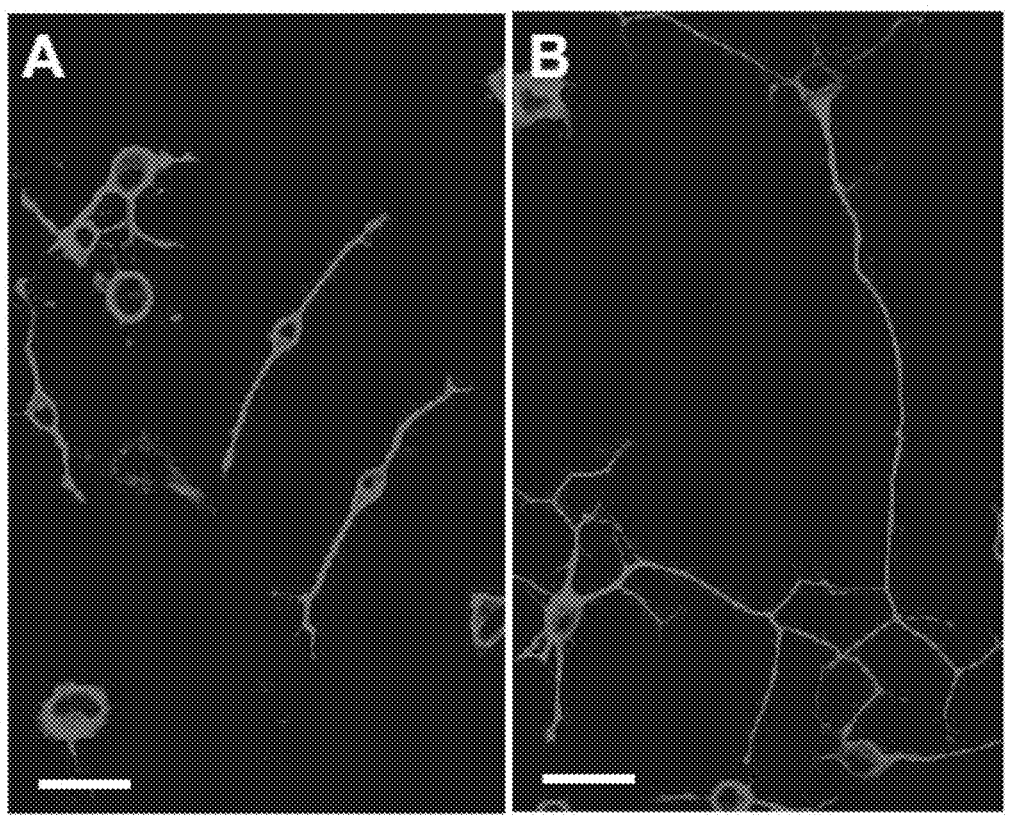
FIGS. 26A-26C: Midi-GAGR enhances neurite outgrowth in N2A cells. Differentiated N2A cells were treated with different concentrations of midi-GAGR for 48 h and immunostained using anti-α-tubulin antibody. Representative confocal images of N2A cells treated with either $H_2O$ (vehicle) (FIG. 26A) or 1 μM midi-GAGR (FIG. 26B). Scale bar=30 μm. Bar graphs in FIG. 236C show the average total neurite lengths of N2A cells treated with different concentrations of midi-GAGR (mean±SEM of, at least, three independent experiments). *, $p<0.05$ compared to control.
Figure 26C:
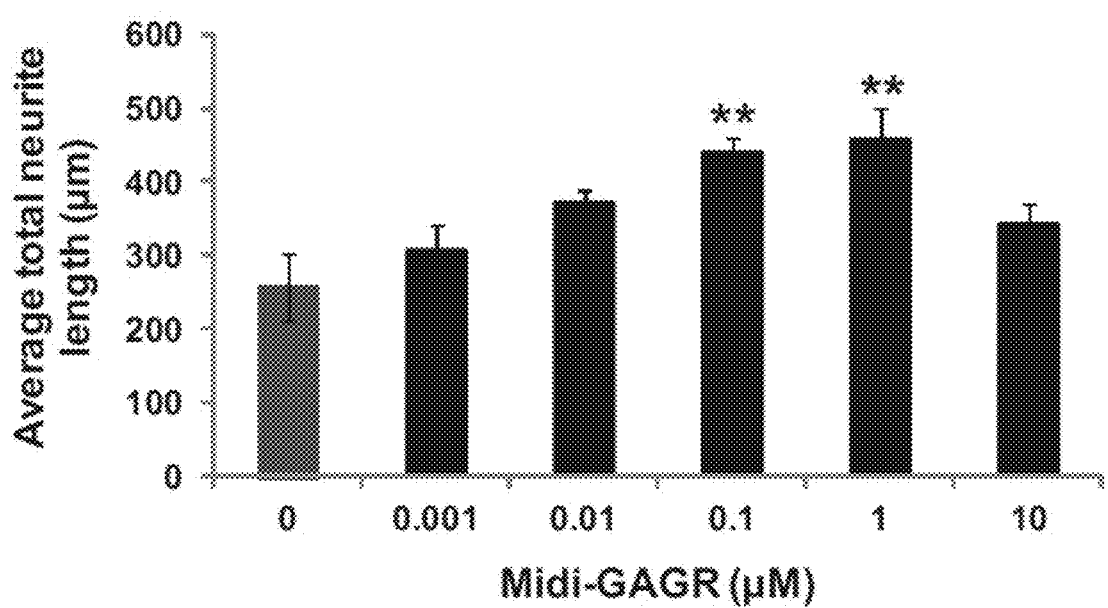

The neuritogenic effect of midi-GAGR on N2A cells was examined. N2A cells were differentiated with increasing concentrations (0, 0.001, 0.01, 0.1, 1, and 10 µM) of midi-GAGR for 48 h. Then, cells were fixed and immunostained with anti-α-tubulin antibody. The total length of neurites per cell was measured using Metamorph and used to calculate average total neurite length per treatment group. At 0.1 and 1 µM, the average total neurite length of midi-GAGR-treated N2A cells reached ~1.7 fold higher than that of vehicle-treated cells (FIGS. 26A-26C; 438.21±20.55 µm [0.1 µM] and 457.76±41.66 um [1 µM] vs. 257.51±45.16 µm [vehicle], p<0.05). At 10 µM, average total neurite length was decreased, which is similar to the pattern of neuritogenesis in cells treated with FGL. The neuritogenic effect of midi-GAGR on primary mouse cortical neurons (E17, DIV4) was examined. Neurons were incubated with vehicle, midi-GAGR (1 µM), dextran (1 µM), alginate (1 µM), LA-GAGR (0.1 µM), or HA-GAGR (0.01 µM) for 2 days and immunostained with the antibody to βIII tubulin (FIGS. 27A-27F). The total neurite length of each neuron was measured to calculate average total neurite length per condition. Then, average total neurite length per condition was divided by that of vehicle treatment to obtain fold change in average total neurite length per condition. Compared to vehicle treatment (FIG. 27A), midi-GAGR (FIG. 27B) and LA-GAGR (FIG. 27C) increased average total neurite length by ~1.6 fold (FIG. 27G). Conversely, HA-GAGR (FIG. 27D), alginate (FIG. 27E), and dextran (FIG. 27F) did not enhance neuritogenesis (FIG. 27G). Thus, midi-GAGR and LA-GAGR have strong neuritogenic effect on rodent cortical neurons.

Figure 28F:
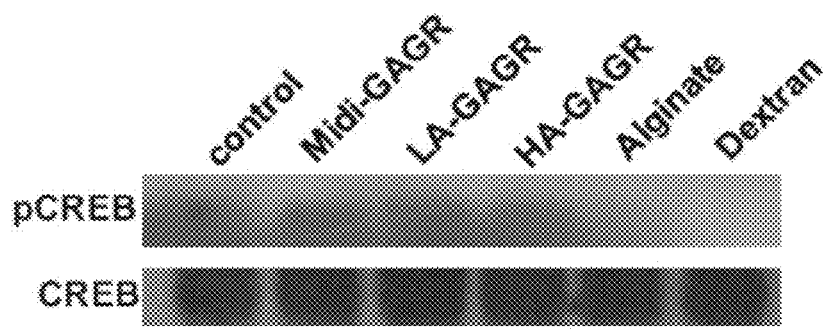

Midi-GAGR Activates CREB, a Neurotrophic Transcriptional Factor midi-GAGR-treated mouse cortical neurons were stained with the antibody to pCREB, a marker for activated neurotrophic signaling pathways. Mouse cortical neurons (E17, DIV4) were treated with vehicle (FIG. 28A), midi-GAGR (1 µM, FIG. 28B), alginate (1 µM, FIG. 28C), dextran (1 µM, FIG. 28D), LA-GAGR (0.1 µM), or HA-GAGR (0.01 µM) for 48 h, fixed, immunostained with the antibodies to α-tubulin and pCREB along with DAPI. The fluorescence intensity (arbitrary number) of stained pCREB in the nucleus was measured using Metamorph. Vehicle-treated neurons showed the basal levels of pCREB in the nuclei (FIG. 28A). Conversely, treatment with either midi-GAGR (FIG. 28B) or LA-GAGR significantly increased the level of nuclear pCREB while the other polysaccharides did not (FIG. 28C, FIG. 28D). Treatment with HA-GAGR slightly increased the level of nuclear pCREB. The average intensity of stained pCREB in the nuclei of the neurons was calculated. Treatment with either midi-GAGR or LA-GAGR increased the average intensity of nuclear pCREB by ~2 fold compared to vehicle treatment (FIG. 28E). To confirm the result of the optical measurement of the level of pCREB, immunoblotting was performed to detect the phosphorylation of CREB protein using the cytosols extracted from mouse cortical neurons treated with vehicle or polysaccharides. Total CREB was also detected by immunoblotting. Compared to control (vehicle treatment), the levels of pCREB were significantly increased in neurons treated with either midi-GAGR or LA-GAGR while those in neurons with either alginate or dextran were not (FIG. 28F). The phosphorylation level of HA-GAGR was also increased. Thus, midi-GAGR and LA-GAGR increase the phosphorylation of CREB significantly and HA-GAGR does slightly.

Figure 29A:
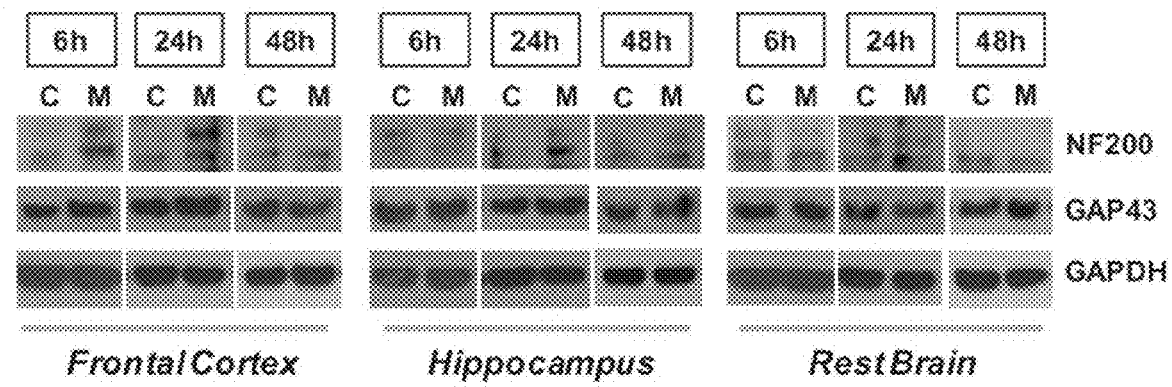
FIGS. 29A-29C: Intranasally administered midi-GAGR increases the expression of NF200 and GAP-43 in the brains of live rats. SD rats were intranasally administered with either vehicle or midi-GAGR and processed to obtain brains at 6 h, 24 h, or 48 h after the administration. Brains were dissected to the frontal cortex, hippocampus, and rest of the brain.
Figure 29B:
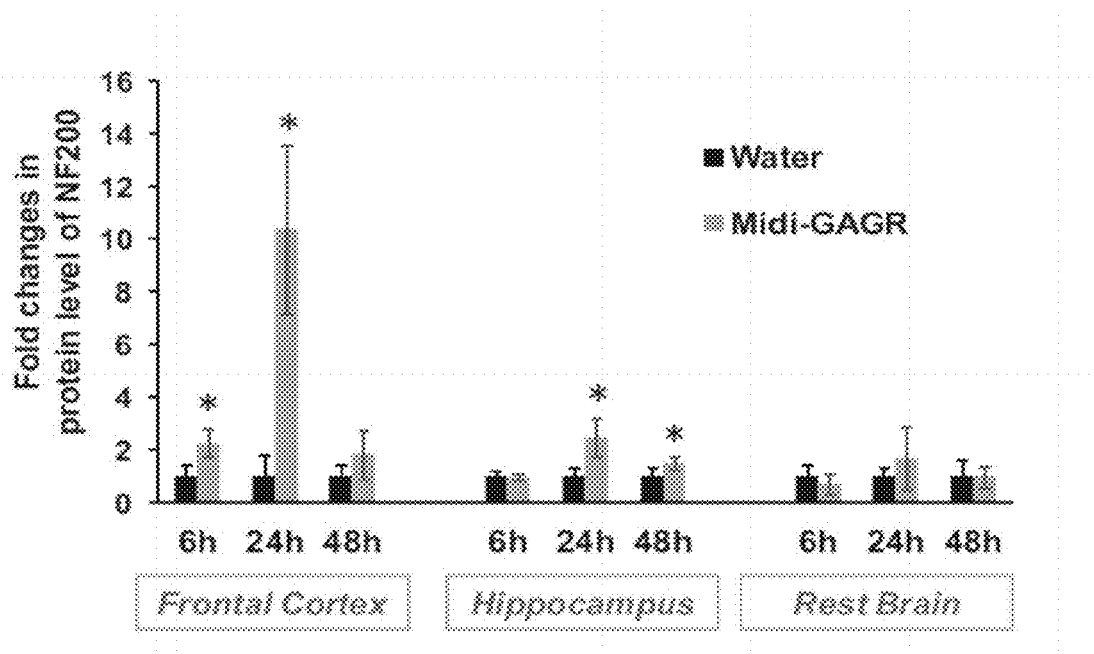
Figure 29C:
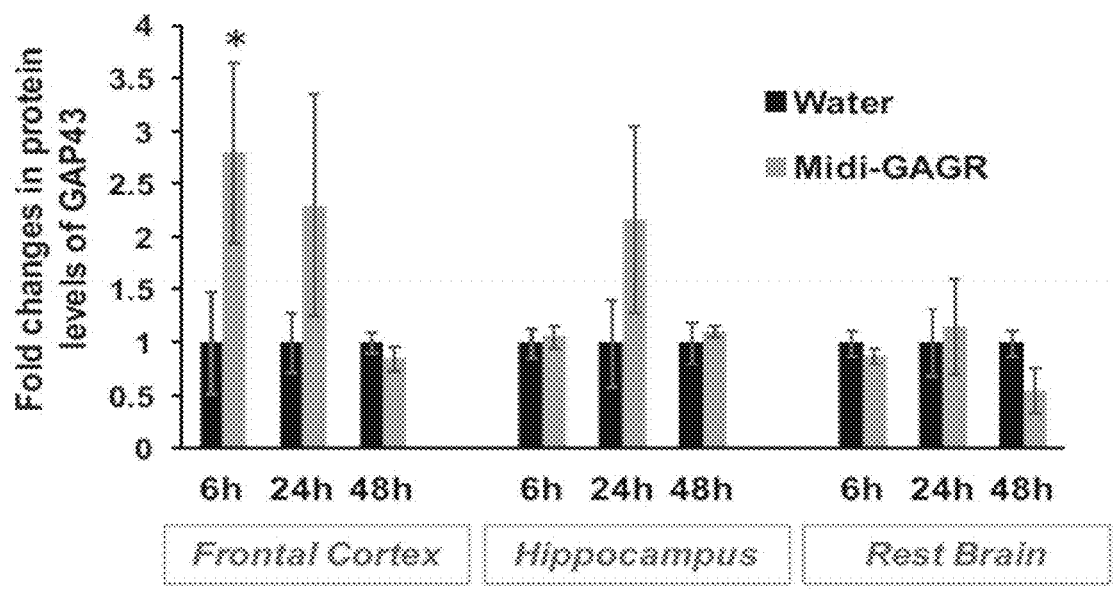

Intranasally Administered Midi-GAGR Penetrates the BBB and Increases the Expression of NF200 and GAP-43 in the Frontal Cortex and Hippocampus The expression of two neurotrophic protein markers, NF200 and GAP-43, was examined in the brains of rats administered intranasally with 40 µL of either $H_2O$ or 1 mM midi-GAGR. At 6, 24, and 48 h after the intranasal administration, the frontal cortex, hippocampus, and the rest of the brain were dissected from the rats and processed for immunoblotting using the antibodies to NF200, GAP-43, and GAPDH (loading control). The protein band densities of NF200 and GAP-43 were measured by densitometry (Image J), normalized by those of GAPDH, and used to calculate average normalized values. In the frontal cortex, the expression level of NF200 was increased to the level significantly higher than control at 6 h and 24 h after the administration (FIG. 29A, FIG. 29B). In the hippocampus, that of NF200 was increased to the level statistically higher than control after 24 h. The expression level of GAP-43 was also significantly increased in the frontal cortex at 6 h and 24 h while slightly increased in the hippocampus at 24 h (FIG. 29A, FIG. 29C). The rest of the brain did not show an increase in NF200 and GAP-43 after one-time intranasal administration. These results show that intranasally administered midi-GAGR enters the brain and exerts its neurotrophic effect in the frontal cortex and hippocampus within 24 h post-administration.

Midi-GAGR Binds to FGFR1 and Activates FGFR1 Signaling Pathway

Figure 30A:

The interaction of midi-GAGR with FGFR1 was examined by affinity chromatography using midi-GAGR-conjugated sepharose column. Either midi-GAGR or dextran was conjugated to epoxy sepharose beads according to manufacturer's protocol. Whole mouse brains were homogenized for cytosol extraction in PMEE buffer containing 1% Igepal CA-630 and protease inhibitor cocktail. Brain cytosols were diluted to 1:2 to make 0.5% Igepal buffer prior to the incubation with either dextran- or midi-GAGR-conjugated sepharose beads on a rotating plate for 16 h at 4° C. Nonspecific bindings were removed by extensive washes in PMEE buffer. Beads were boiled for protein elution. FGFR1 was one of the proteins eluted from midi-GAGR beads but not from dextran beads (FIG. 30A).

Figures 30B, 30C:
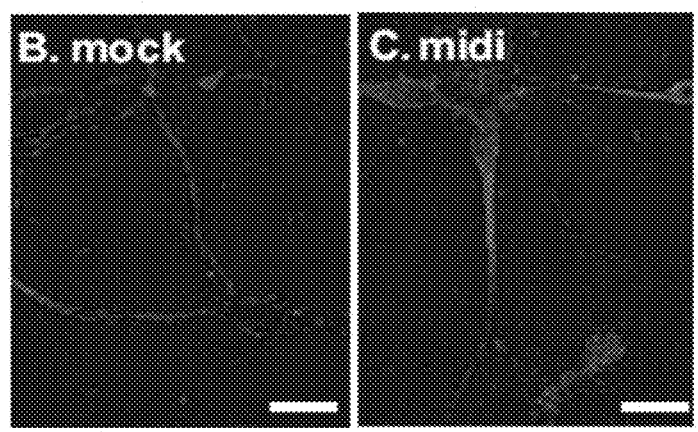
Figure 30J:
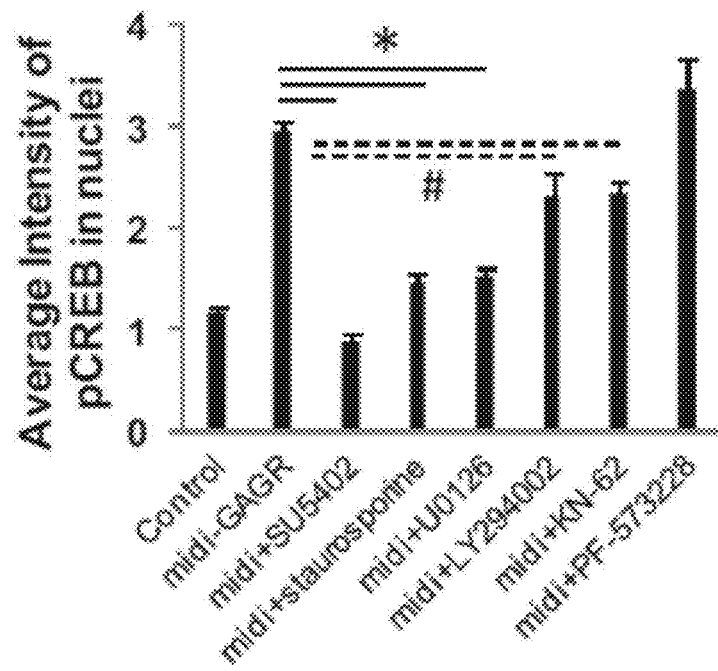

Pharmacological agents were used to inhibit signaling molecules downstream of FGFR1 that mediate CREB phosphorylation. The fluorescence intensities of nuclear pCREB in mouse cortical neurons (E17, DIV6) pre-treated for 6 h with the inhibitors of FGFR1 (SU5402 [SU], 4 μM), PKC (staurosporine [Stau], 3 nM), MEK (U0126 [U01], 10 μM), PI3K (LY294002 [LY], 20 μM), or CaMKII (KN-62 [KN], 10 μM); and, then with 1 μM midi-GAGR (midi) for 48 h were measured. PF-573228 (PF, 1 μM) that inhibits FAK which sits at the bottleneck of the signaling pathway downstream of NCAM180 was also included to examine whether NCAM180 is involved in midi-GAGR-mediated CREB phosphorylation or not. Treated neurons were stained with the antibodies to βIII tubulin (red) and pCREB (green) for the measurement of the average intensities of nuclear pCREB. Compared to neurons treated with vehicle (FIG. 30B, FIG. 30J), those with midi-GAGR (midi) showed a significant increase (~2.6 fold) in the average intensity of pCREB (FIG. 30C, FIG. 30J). Conversely, pre-treatment with the inhibitor of FGFR1 (FIG. 30D, FIG. 30J), PKC (FIG. 30E, FIG. 30J), or MEK (FIG. 30F, FIG. 30J) significantly decreased the average intensity of pCREB (solid lines, *: $p<0.01$, n=40-50 neurons). In neurons pre-treated with the inhibitor of either PI3K or CaMKII, the average intensity of pCREB was decreased slightly but still statistically significantly (dotted lines, #: $p<0.05$, n=40-50 neurons). In contrast to the inhibitors, pre-treatment with FAK inhibitor did not decrease the average intensity of pCREB in midi-GAGR-treated neurons (FIG. 30I, FIG. 30J). These results show that midi-GAGR activates FGFR1 and its downstream signaling pathways consisting of PKC, MEK, PI3K, and CaMKII, but not NCAM180-FAK signaling pathway for CREB phosphorylation.

Figure 30K:
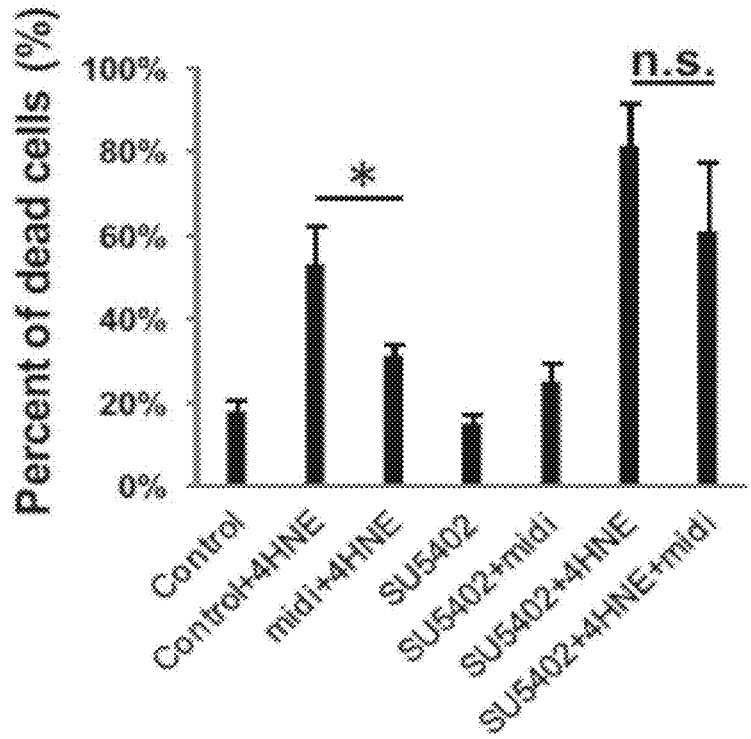

How FGFR1-mediated neurotrophic signaling pathway contributes to midi-GAGR-mediated neuroprotection against oxidative insult was examined. Rat cortical neurons (E17, DIV6) were pre-treated for 6 h with FGFR1 inhibitor (SU5402, 4 μM) and then with 10 μM 4HNE for 24 h prior to LIVE/DEAD Viability/Cytotoxicity Assay. Treatment with 4HNE increased the percent of dead cells from ~20% to ~60% while co-treatment with 1 μM midi-GAGR decreased that to ~30% (FIG. 30K). Treatment with SU5402 alone or SU5402 plus midi-GAGR did not increase the percent of dead cells (FIG. 30K). Interestingly, pre-treatment with SU5402 significantly increased the percent of dead cells up to ~80% upon the post-treatment with 4HNE (FIG. 30K). In neurons pre-treated with SU5402 and then treated with 4HNE, midi-GAGR could not decrease the percent of dead cells. This result show that FGFR1-mediated signaling pathway plays a major role in midi-GAGR-mediated neuroprotection against oxidative insult.

Figure 31A:
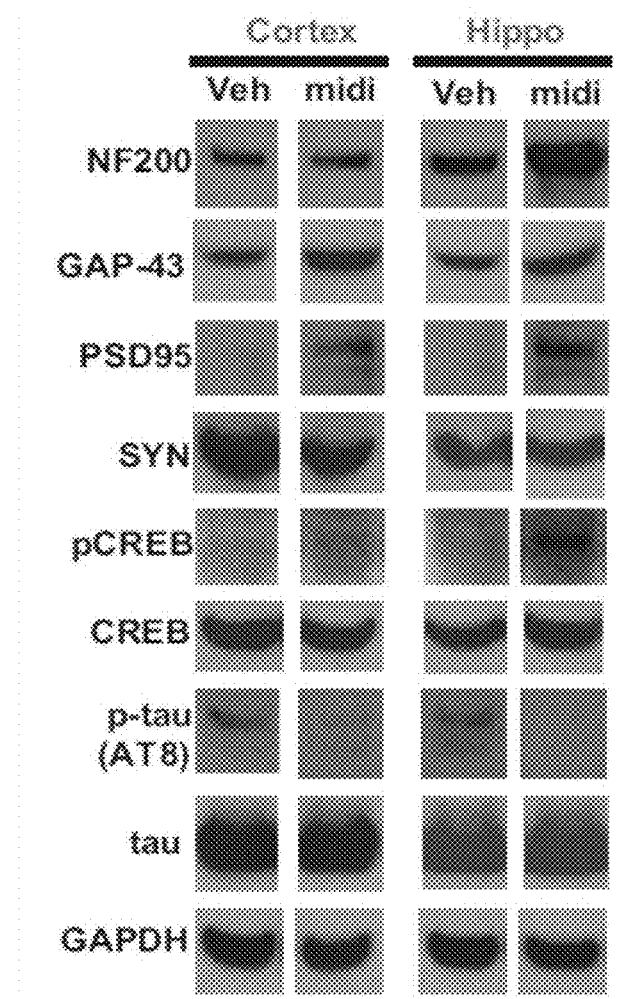
Figure 31B:
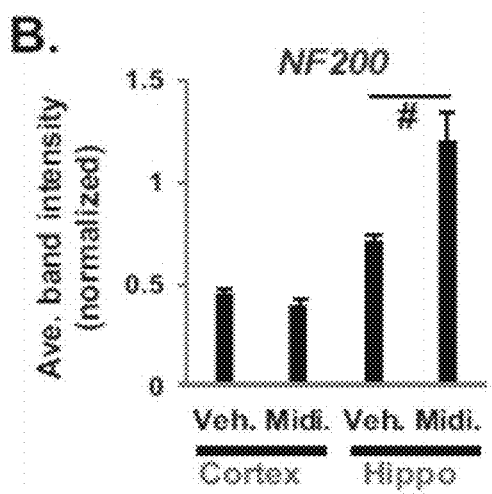
Figure 31C:
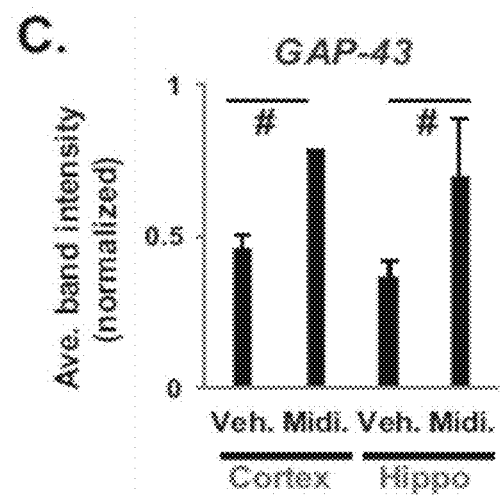

Intranasally Administered Midi-GAGR Increases Neuronal Activity Markers and Reduces Hyperphosphorylated Tau in 3×Tg-AD Mice It was determined whether midi-GAGR treatment increases the protein markers of neuronal activity and reduces the neurodegeneration marker, hyperphosphorylated tau (P-Ser202), in AD brain. 12-month-old 3×Tg-AD mice that harbor two familial AD mutations, $APP_{swe}$ and $PS1_{M146V}$, and the $tau_{P301L}$ mutation found in frontotemporal dementia were used. Around 12 months of age, 3×Tg-AD mice show synapse loss, Aβ peptide accumulation, memory deficit, and tau hyperphosphorylation. Female 3×Tg-AD mice were used since females show more obvious cognitive defects than males. 40 μL of vehicle (sterile $H_2O$) or 7.4 mM midi-GAGR were administered intranasally into female 3×Tg-AD mice once per day for 14 days. During midi-GAGR administration, 3×Tg-AD mice did not show any abnormal behavior. Of note, 3×Tg-AD mice administered with midi-GAGR made tight nest every day while those with vehicle made loose nests. After 14-day administration, mice were killed for brain extraction. Extracted brains were dissected to obtain the cortices and hippocampi. The brain tissues were lysed in PMEE buffer containing 1% Igepal CA-630 and phosphatase and protease inhibitor cocktails for immunoblotting using antibodies to NF200, GAP-43, PSD95, synaptophysin (SYN), pCREB, CREB, p-tau (AT8), tau, and GAPDH. The protein band densities of detected proteins were normalized by those of GAPDH and used to calculate average normalized band density for each protein. Compared to 3×Tg-AD mice administered with vehicle (Veh.), NF200 was increased significantly in the hippocampus of those with midi-GAGR while not changed in the cortex (FIG. 31A, FIG. 31B). GAP-43 and PSD95, the postsynaptic markers for increased synaptic activity, were increased significantly in both cortex and hippocampus of 3×Tg-AD mice treated with midi-GAGR compared to control while synaptophysin (SYN) remained unchanged (FIG. 31A, FIG. 31C, FIG. 31D, FIG. 31E). pCREB, another postsynaptic marker that shows increased neurotrophic signaling, was also significantly increased in both cortices and hippocampi of 3×Tg-AD mice treated with midi-GAGR compared to control (FIG. 31A, FIG. 31F). Total CREB was slightly increased in the hippocampus of midi-GAGR-treated 3×Tg-AD mice while not changed in the cortex (FIG. 31A, FIG. 31G). Surprisingly, hyperphosphorylated tau (P-Ser202) was drastically decreased in the hippocampus of 3×Tg-AD mice and slightly in their cortices (FIG. 31A, FIG.

31H). Total tau was not changed (FIG. 31A, FIG. 31I). These results show that intranasally administered midi-GAGR not only enhances neuronal and synaptic activities in the cortex and hippocampus but also decreased hyperphosphorylated tau, a major AD facilitator, in the brains of 3×Tg-AD mice.

DISCUSSION

This Example demonstrates that intranasally administered midi-GAGR penetrates the BBB and exerts its neurotrophic effect for 24 h after one time administration. This indicates that midi-GAGR has a good BBB-permeability and a long plasma half-life of ~24 h.

In the in vitro experiments, midi-GAGR showed a strong neuroprotective effect. At 0.1-1 µM, midi-GAGR protected the neurites of differentiated N2A cells up to 70-90% from the atrophy caused by the supra-physiological concentrations of two free reactive radicals, 4HNE and $H_2O_2$. At 1 µM, midi-GAGR protected primary rodent cortical neurons from the pathological concentrations of post-/co-treated free radicals and amyloid $\beta_{42}$ peptide. The protective effect of midi-GAGR against co-existing free radicals and amyloid $\beta_{42}$ peptide is clinically relevant as treatment is usually applied to the pre-existing pathological conditions like high levels of free radicals and amyloid $\beta_{42}$ peptide. It was also observed that 1 mM midi-GAGR protected rodent cortical neurons from more vicious neurodegenerative factor, activated microglial cells. Thus, it is clear that midi-GAGR is a strong neuroprotective agent. In contrast, the control polysaccharides dextran (D-Glc polymer), alginate (D-GlcA polymer), and HA-GAGR (highly acylated LA-GAGR), could not protect neurons from both free radicals and amyloid $\beta_{42}$ peptide. Thus, the neuroprotective effect of midi-GAGR is sequence-specific, which may confer midi-GAGR a specific binding to a certain molecule such as receptor.

In addition to the neuroprotective effect, midi-GAGR showed a strong neurotrophic effect both in vitro and in vivo. In vitro, midi-GAGR greatly enhanced neuritogenesis in N2A cells at 0.1-1 µM and in rodent cortical neurons at 1 µM. Other control polysaccharides such as dextran, alginate, and HA-GAGR could not enhance neuritogenesis. Similarly, in rodent cortical neurons, midi-GAGR increased the nuclear levels of activated pCREB, the transcriptional factor that enhances neuronal activities for survival and memory, while dextran and alginate did not. HA-GAGR activates CREB to some extent but less than midi-GAGR. A similar neurotrophic effect of midi-GAGR in the brains of rodents that were intranasally administered with midi-GAGR was observed. In the frontal cortices and hippocampi of midi-GAGR-administered animals, the markers for neuritogenesis (NF200) and synaptic activity (GAP-43) were increased within 24 h after one-time intranasal spray. Thus, this in vitro and in vivo evidence clearly manifest the neurotrophic property of midi-GAGR.

A pulldown experiment and pharmacological inhibitor evaluation was performed and found that midi-GAGR interacts with FGFR1 and appears to activate two FGFR1 signaling pathways, FRS2a-Shc-Grb2-PKC-Raf-MEK and PI3K-Akt/PLCγ-Ca2+-CaMKII pathway. Based on the observation that the levels of pCREB were reduced more drastically by PKC and MEK inhibitors than by PI3K and CaMKII, FRS2a-Shc-Grb2-PKC-Raf-MEK pathway plays a more major role than PI3K-Akt/PLCγ-Ca2+-CaMKII pathway for CREB activation. It was also found that FAK is not involved in midi-GAGR-FGFR1 signaling pathway as midi-GAGR-induced CREB phosphorylation was not decreased by the inhibitor of FAK that sits at the bottleneck of NCAM180 signaling pathway. The selective activation of FGFR1 over NCAM180 is beneficial in the clinical application of midi-GAGR since the activation of NCAM often leads to undesired effects. Both FGF (e.g., FGF2) and FGL have shown a great efficacy in attenuating neurodegeneration and improve memory in AD mice. Moreover, both FGF2 and FGL reduce AD pathogenic factors. Therefore, midi-GAGR may exert the similar beneficial effects to FGF or FGL while with longer plasma half-life than those peptides.

At the low concentrations below 1 µM, dextran and alginate could not protect rodent cortical neurons from the pathological concentrations of 4HNE and $H_2O_2$. Moreover, the polysaccharides and HA-GAGR could not protect the neurons from the relatively low but pathological concentration (2 µM) of $A\beta_{42}$ peptide. In contrast to the control polysaccharides, midi-GAGR as well as LA-GAGR could protect the neurons from all three neurodegenerative factors, 4HNE, $H_2O_2$, and $A\beta_{42}$ peptide. This result indicates that the neuroprotective effect of midi-GAGR does not depend on its antioxidant property. To further clarify this, rodent cortical neurons were pre-treated with FGFR1 inhibitor prior to the treatment with 4HNE. Midi-GAGR could not rescue neurons from 4HNE-induced death in neurons pretreated with FGFR1 inhibitor, indicating that FGFR1-mediated neurotrophic signaling pathway is the major mechanism by which midi-GAGR rescues neurons from oxidative insult induced death. FGFR1 inhibitor increased the percent of neuron death caused by 4HNE to even higher than vehicle plus 4HNE. This indicates that FGFR1 is important for neuron survival in the presence of high oxidative insult.

The efficacy of midi-GAGR in enhancing neuronal activity and reducing pathogenic factor in the brains of 3×Tg-AD mice that are known to demonstrate most AD pathogenic progresses until the age of 12 month was examined. Consistent with the results of SD rats, intranasally administered midi-GAGR increased both NF200 and GAP-43, the markers of increased neuritogenesis and synaptic activity, respectively, in the hippocampus. In the cortex, only GAP-43 was increased while NF200 was not changed. No change in NF200 in the cortex may be due to the saturation of the neuritogenic effect of midi-GAGR at the concentration of equal to or higher than 1 µM, similarly to the result of the in vitro experiment. In addition to NF200 and GAP-43, PSD95, and pCREB, the indicators of increased synaptic activity, were also increased in both cortex and hippocampus. The increase in all four markers for enhanced neuronal activity in the brain of 3×Tg-AD mice is strong evidence that shows a great ability of midi-GAGR for restoring the learning and memory function of the brain in AD mice.

Surprisingly, a reduction of hyperphosphorylated tau (P-Ser202) in the hippocampi of 3×Tg-AD mice was observed. Hyperphosphorylated tau is a reliable biomarker for "mild cognitive impairment" (MCI) at early AD. Hyperphosphorylation impairs the function of tau in promoting microtubule polymerization, resulting in its aggregation to form neurofibrillary tangles (NFTs), microtubule disassembly, and loss of axonal microtubule-based transport. Without wishing to be bound by theory, it is believed that midi-GAGR may inhibit GSK3β, the major kinase responsible for tau hyperphosphorylation, in a similar way to FGL.

This Example demonstrates the abilities of a BBB-permeable, long plasma half-life, strong neuroprotective and neurotrophic polysaccharide, midi-GAGR. BBB-permeable midi-GAGR can exert its neurotrophic effect in the cortex and hippocampus for ~24 h after one-time intranasal administration. Moreover, midi-GAGR not only increases protein markers for increased neuronal activity but also reduces hyperphosphorylated tau in the brains of 3×Tg-AD mice. In sum, this Example shows that midi-GAGR has great therapeutic characteristics (neurotrophic, neuroprotective, BBB-permeable, and long plasma half-life) for the treatment of neurodegenerative diseases, especially AD.

Example 5

Nesting Behaviors Using Midi-GAGR

Figure 32A:
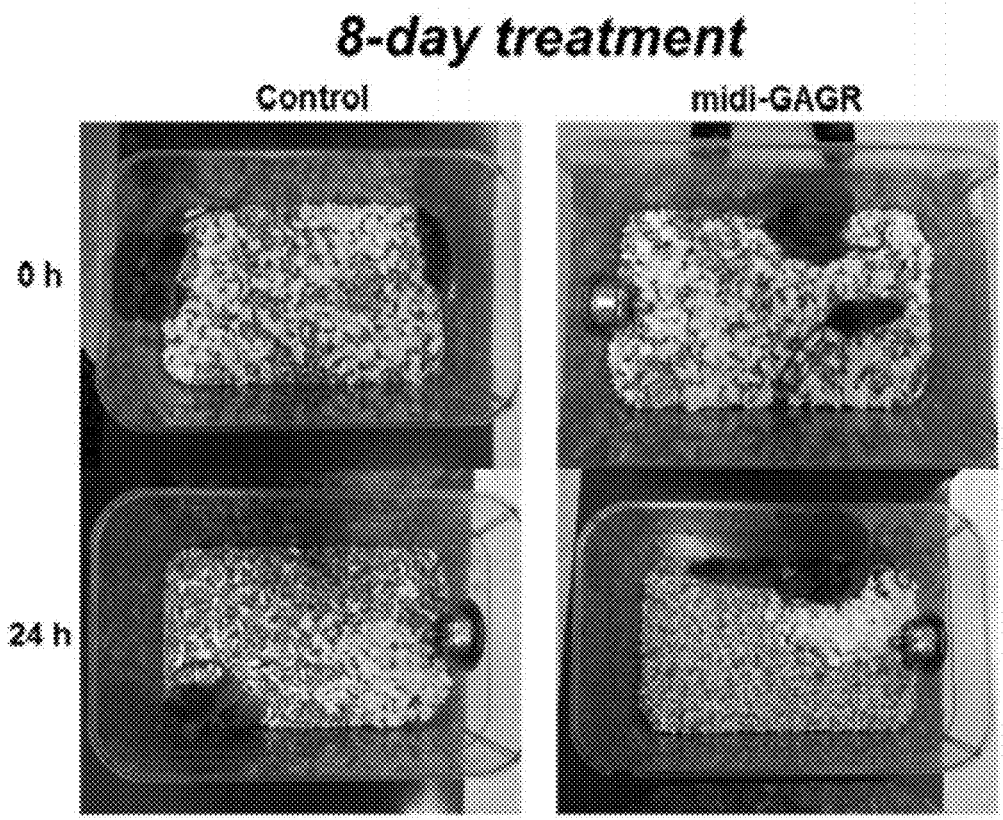
FIGS. 32A-32B: 3×Tg-AD mice were treated either with sterile water (vehicle) or 0.296 nmole of midi-GAGR for 14 days. White feathery papers were scattered at 0 hr. After 24-h post treatment, the image of the cages was taken by a camera (FIG. 32A). The daily sizes (areas) of the nests made by the mice were measured using software and used to calculate average nest size (FIG. 32B).

3×Tg-AD mice were treated either with sterile water (vehicle) or 0.296 nmole of midi-GAGR for 14 days. White feathery papers were scattered at 0 hr. After 24-h post treatment, the image of the cages was taken by a camera (FIG. 32A).

Figure 32B:
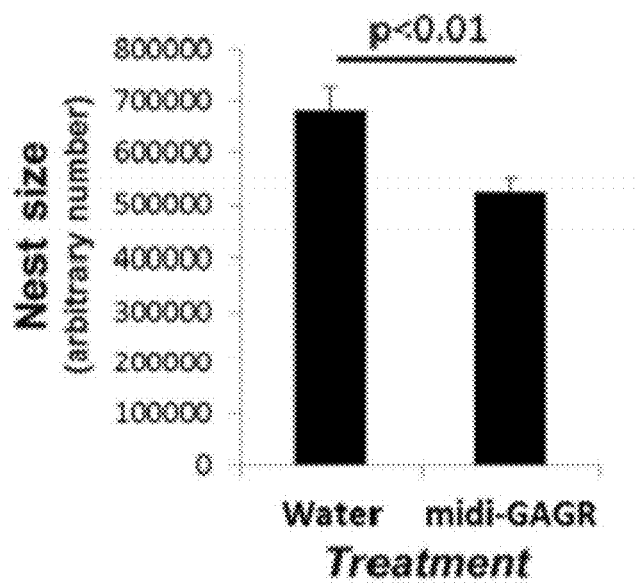

The daily sizes (areas) of the nests made by the mice were measured using software and used to calculate average nest size (FIG. 32B).

Midi-GAGR-treated 3×Tg-AD mice showed better nesting behavior than vehicle-treated mice. The nesting behavior is known to be impaired in 3×Tg-AD mice, which corresponds to a deterioration of executive functions and daily live activities (DLA) in humans. DLA is used along with behavioral and psychological symptoms of dementia to diagnose early AD in humans. Moreover, nesting behavior heavily depends on the hippocampus. Midi-GAGR rescued some hippocampal function involved in nesting behavior.

Example 6

Wound Healing

Midi-GAGR and mini-GAGR were produced from low acyl gellan gum. Low acyl gellan gum (an average molecular weight [MW] of ~99,700 g/mole) was digested with $\alpha(1\rightarrow3)$-glucosidase for 48 h and 72 h to generate midi-GAGR (4.7 kD) and mini-GAGR (0.8 kD), respectively. The MWs of midi-GAGR and mini-GAGR were determined using a Parallel Plate Rheometer on the basis of the viscosity profile of cleavage products.

Mini-GAGR and midi-GAGR increased blood vessel formation from human endothelial cells (HUVECs). HUVECs were plated on a matrigel-coated 24-well plate (1.2×105/0.3 mL/well), added with Endothelial Cell Growth Media Kits (EGM [Lonza, Walkersville, Md.]), and incubated in 5% $CO_2$ at 37° C. for 16-18 h. Then, tubes formed from HUVECs were fixed and labeled with Acridine Orange (1 μg/ml) and imaged using a fluorescent microscope. The total length of tubes per image was measured using 'Metamorph' software. Treatment with midi-GAGR and mini-GAGR (0.1-1 μM) increased the formation of blood vessels by 2 fold compared to untreated control (FIG. 33). This result indicates that both midi-GAGR and mini-GAGR have a strong vasculogenic effect. This neovascularization facilitates wound healing.

Mini-GAGR and midi-GAGR enhanced the production of GAGs and collagen, which make up the extracellular matrix that fills a wound scar. Human bone marrow-derived mesenchymal stem cells (hBM-MSCs) were incubated in cartilage forming condition plus/minus 0.1-1 μM mini-GAGR or midi-GAGR. As a result, 0.1-1 μM mini-/midi-GAGR drastically enhanced the production of type II collagen and glycosaminoglycans (GAGs) in cartilage cells (FIGS. 34A-34B). Thus, both midi-GAGR and mini-GAGR enhanced the production of GAGs and collagen, the major tissue components for wound healing.

FGFs are major protein growth factors used for wound healing. GAGR cleavage products bound to an FGF receptor. FIG. 35 shows that mini-GAGR interacts with FGFR1. Affinity chromatography was performed using epoxy sepharose beads to which either dextran (control) or mini-GAGR was conjugated. After nonspecific binding was blocked and removed by bovine serum albumin and extensive washes, respectively, the beads were incubated in the plasma membrane extractions of Neuro 2A cells. The binding of FGFR1 to the beads was then examined by immunoblotting using anti-FGFR1 antibody (FIG. 35). It is clear that FGFR1 specifically binds to mini-GAGR but not to dextran.

Figure 36A:
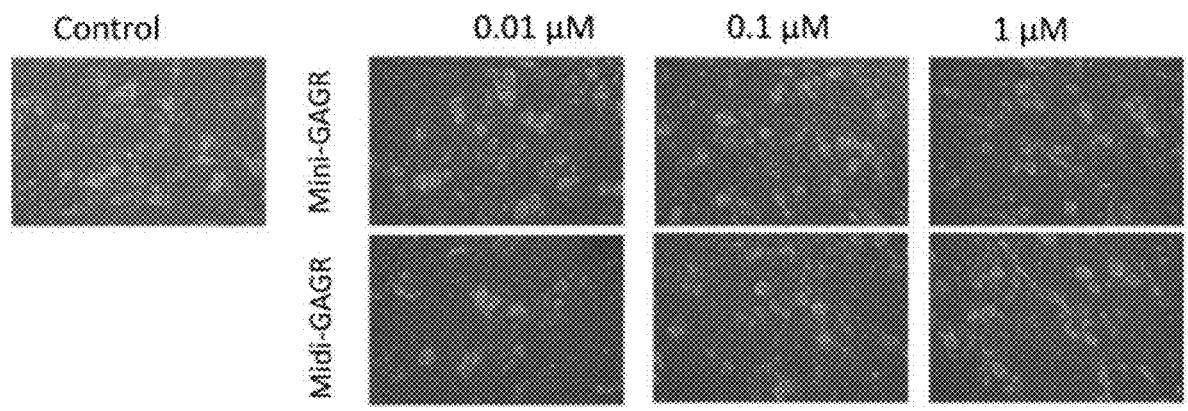
FIGS. 36A-36B: Human BM-MSCs were treated with 1 (control: $H_2O$), 0.01, 0.1, or 1 μM of midi-GAGR or mini-GAGR for 14 days in adipogenic medium. Thereafter, differentiated or undifferentiated cells were stained with Oil-red O and imaged using light microscopy.
Figure 36B:
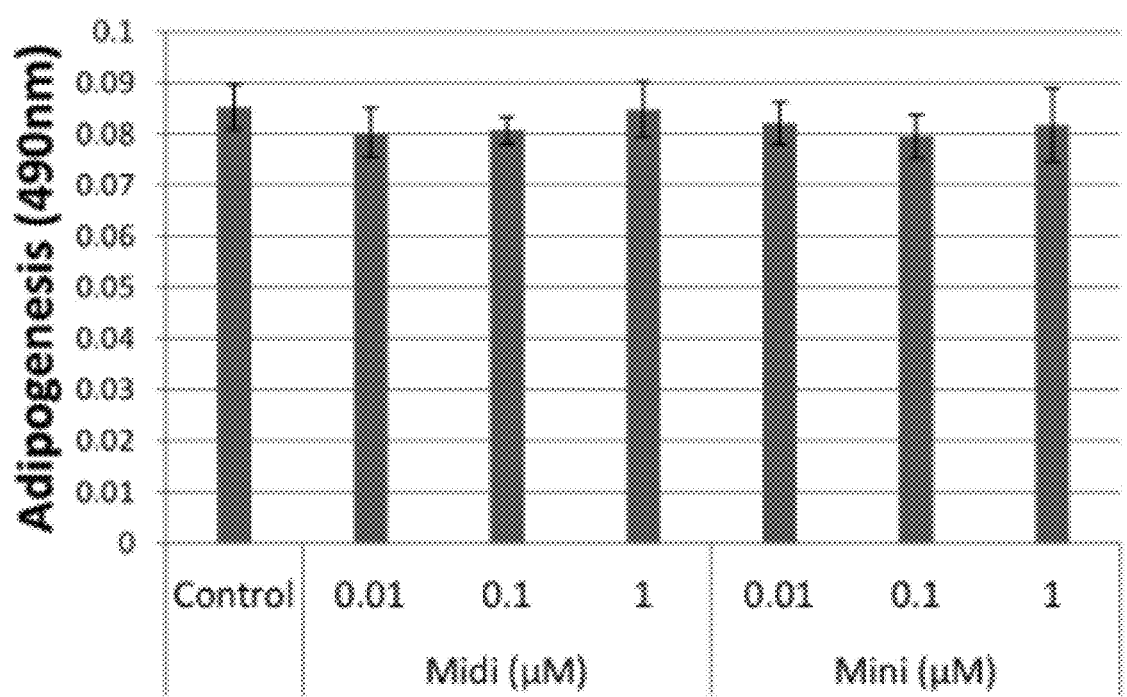

Midi-GAGR and mini-GAGR did not enhance adipogenesis. Human BM-MSCs were incubated in adipogenic media (DMEM containing 4.5 g/L glucose, 10 μg/mL insulin, 60 μM indomethacin, 10 μM indomethacin, 10% FBS, and antibiotic-antimycotic), and treated with none (control), 0.01, 0.1, or 1 μM of midi-GAGR or mini-GAGR every 2nd day for 14 days. Thereafter, cells were stained with Oil-red 0 that stains lipid droplets and imaged using light microscope. The extents of adipogenesis were measured by microplate reader (absorbance at 490 nm). Treatment with midi-GAGR or mini-GAGR did not enhance adipogenesis in MSCs (FIGS. 36A-36B). Thus, these GAGR cleavage products do not cause fat formation.

Midi-GAGR and mini-GAGR do not have a mitogenic effect. Human BM-MSCs were incubated in α-MEM plus 10% FBS and none (control), 0.1, or 1 μM of midi-GAGR or mini-GAGR for 7 days. Then, the number of cells was counted using heamatocytometer (n=6). Neither midi-GAGR nor mini-GAGR increased the proliferation of MSCs compared to control, indicating that midi-GAGR and mini-GAGR do not have a mitogenic (tumorigenic) effect.

This Example demonstrates a significant therapeutic ability of midi-GAGR and mini-GAGR for wound healing treatments. Without wishing to be bound by theory, it is believed that low acyl gellan gum has the same effects as its cleavage products in this regard.

Example 7

Described in this Example is an efficient and effective method to track an exogenous polysaccharide among endogenous polysaccharides in animals. Instead of using complicated methods and equipment, a fluorescent tag, 8-aminonaphthalene-1,3,6-trisulfonic acid disodium salt (ANTS), can be used to label, track, and quantify a target polysaccharide in animal. 75% ethanol can be used to examine the structural intactness of ANTS-polysaccharide in animal sample. TCA and 75% ethanol can be used to separate free ANTS-polysaccharides from those bound to proteins. For example, the following equipment was used: SpectraMax M5 plate reader (Molecular Devices, Sunnyvale, Calif.); VERSA max plate reader (Molecular Devices); SoftMax Pro 5.2. (Molecular Devices); microcentrifuge.

Conjugation of ANTS to Polysaccharide

A 4.7 kD cleavage product of gellan gum (named midi-GAGR: digestion by $\alpha(1\rightarrow3)$ glycosidase) was tagged with ANTS and examined regarding its BBB-permeability.

To conjugate ANTS (Molecular Probes, Eugene, Oreg.) to midi-GAGR, 454 of 7.4 mM midi-GAGR was mixed with 75 μL of 0.2 M ANTS (7.6 mg ANTS in 8904 of acetic acid [3/17, v/v]), which gives the final ratio of 1:400 (polysaccharide:ANTS) that is optimal for high-efficiency conjugation between polysaccharide and ANTS.

The mixture was briefly vortexed and incubated in an 80° C. water bath for 30 min. The mixture was then added with 375 µL of 1 M NaCNBH$_3$ (Sigma-Aldrich, St. Louis, Mo.), briefly vortexed, and incubated in an 80° C. water bath for 90 mM. Although 37° C. can be also used for 15-h conjugation, 80° C. was used to shorten conjugation time. The mixture was split into 250-µL aliquots, each of which was mixed with 750 µL of 100% pure ethanol to make a final concentration of 75% ethanol.

The mixture was briefly vortexed, incubated at −80° C. for 30 min, and centrifuged at 3,000×g for 30 min to pellet ANTS-tagged midi-GAGR.

In order to remove free ANTS that might be trapped in ANTS-midi-GAGR pellet, the pellet was washed with 400 µL of 75% ethanol to dissolve ANTS trapped in the pellet. After the pellet of ANTS-midi-GAGR was resuspended in 400 µL of 75% ethanol by pipetting, it was re-precipitated at 3,000×g for 10 min. This step was repeated three times. The final pellet was resuspended in 50 µL of sterile de-ionized water.

Centrifugation at 15,700×g was also used for ethanol precipitation of ANTS-tagged polysaccharide. However, it resulted in precipitation of free ANTS. Therefore, the speed of centrifugation was decreased to 3,000×g, thus preventing the precipitation of free ANTS while still precipitating the similar amount of polysaccharide to that after the centrifugation at 15,700×g. In another embodiment, 70% ethanol can be used instead of 75% to reduce the precipitation of free ANTS that might be trapped in ANTS-polysaccharide pellet. Washes with 70% ethanol precipitation decreased the amount of ANTS at the pellet; however, there was also a noticeable loss of polysaccharide at the pellet after each wash. Thus, 75% ethanol was a desired concentration of ethanol to precipitate the maximal amount of polysaccharide and the minimal amount of free ANTS.

Calculation of the Conjugation Ratio of ANTS to Polysaccharide in ANTS-Polysaccharide The amounts of ANTS and midi-GAGR in ANTS-polysaccharide conjugate were measured by fluorometry and colorimetry, respectively, to calculate the ratio of ANTS to midi-GAGR in the conjugate.

For fluorometry, the ANTS-polysaccharide pellet was resuspended and diluted in 50 of fresh water. The dilutions were placed in the wells of a 96-well black-wall plate. The emission fluorescence signals (excitation at 350 nm, emission at 520 nm; relative fluorescence units [RFUs]) of the dilutions were measured using SpectraMax M5 plate reader and SoftMax Pro 5.2. A standard curve of ANTS was generated using 0, 0.1, 0.3, 1, 3, and 10 mM ANTS to calculate the concentrations of ANTS in the samples.

For colorimetry, a modified phenol-sulfuric acid method modified was used.

ANTS-polysaccharide pellet was resuspended and diluted in 50 µL of fresh water. The dilutions were placed in the wells of a 96-well clear-wall plate. Each sample was added with 150 µL of concentrated H$_2$SO$_4$ and then 30 µL of 5% phenol (88% phenol liquefied USP [University of Toledo Medical Center, Toledo, Ohio] diluted in distilled water). The top of the plate was covered with a plate sealer and heated at 95° C. for 5 min. Using VERSA max plate reader and SoftMax Pro 5.4, the absorbance at 490 nm of each well was measured. A standard curve of midi-GAGR was generated using 0, 0.0074, 0.074, 0.74, and 7.4 mM midi-GAGR to calculate the concentrations of midi-GAGR in the samples.

Calculation of the Ratio of ANTS to Midi-GAGR in the Conjugate

Figure 37A:
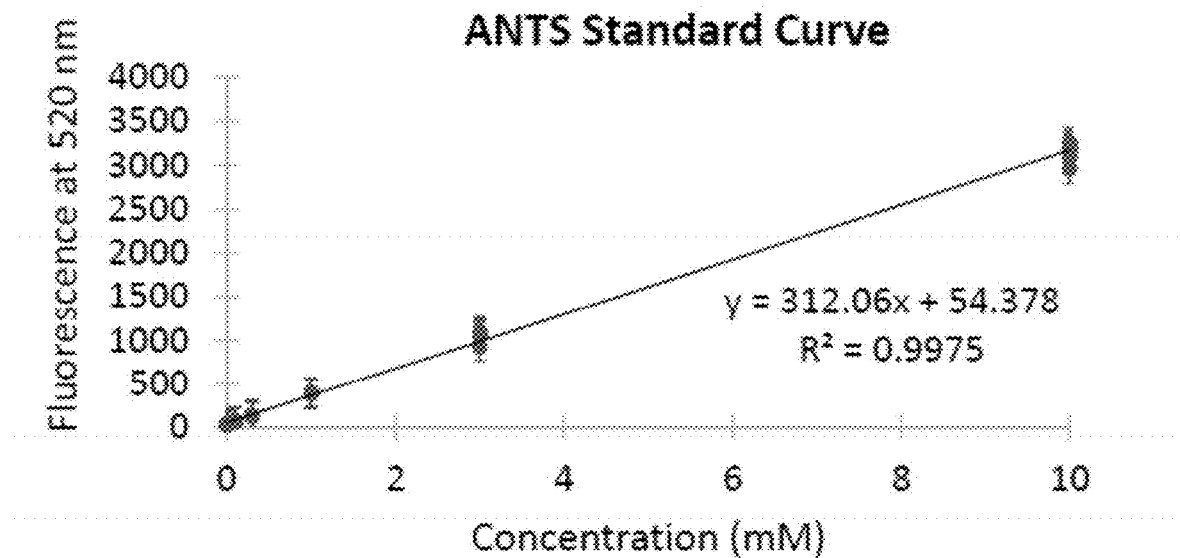
FIG. 37A: The standard curve of emissions at 520 nm (relative fluorescence unit: RFU) of ANTS at 0, 0.1, 0.3, 1, 3, and 10 mM (n=5).

The standard curve of ANTS was generated using the RFUs of 0, 0.1, 0.3, 1, 3, and 10 mM free ANTS to quantify the concentrations of ANTS in the samples. FIG. 37A shows the standard curve of ANTS($R^2$=0.9975) that was generated on the basis of three different measurements.

Figure 37B:
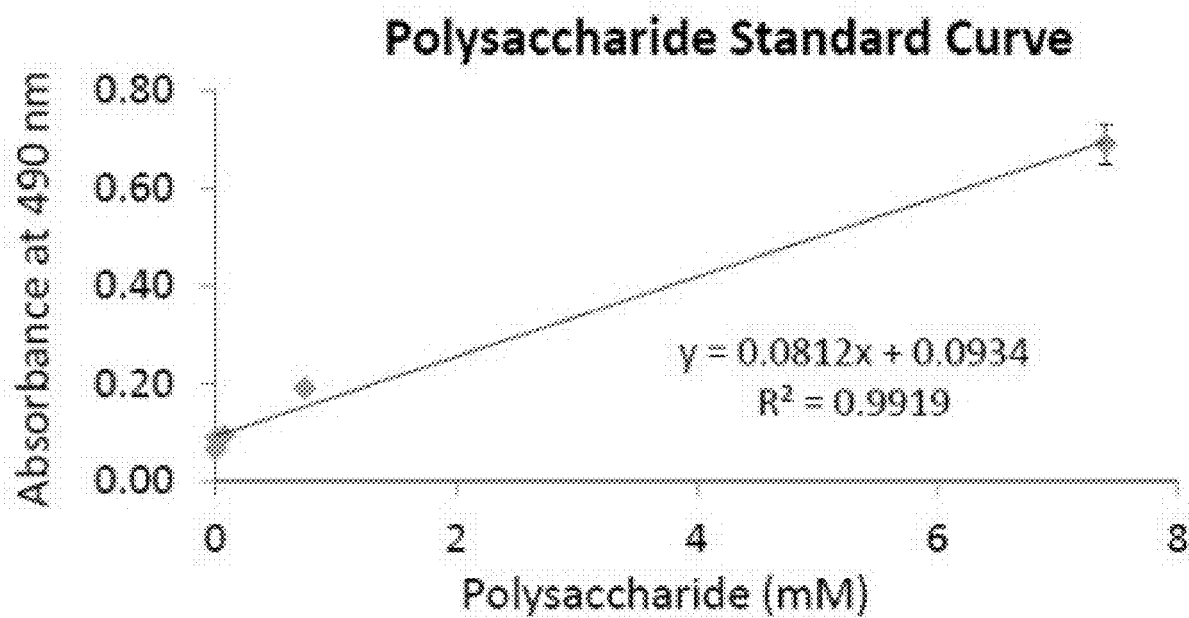
FIG. 37B: The standard curve of absorbances at 490 nm for 0, 7.4, and 74 nM, 0.74 and 7.4 mM of midi-GAGR (n=3).

The standard curve of midi-GAGR was generated using the absorbances at 490 nm for 0, 0.0074, 0.074, 0.74, and 7.4 mM free midi-GAGR. FIG. 37B shows the standard curve of midi-GAGR ($R^2$=0.9919).

Figures 37C, 38A:
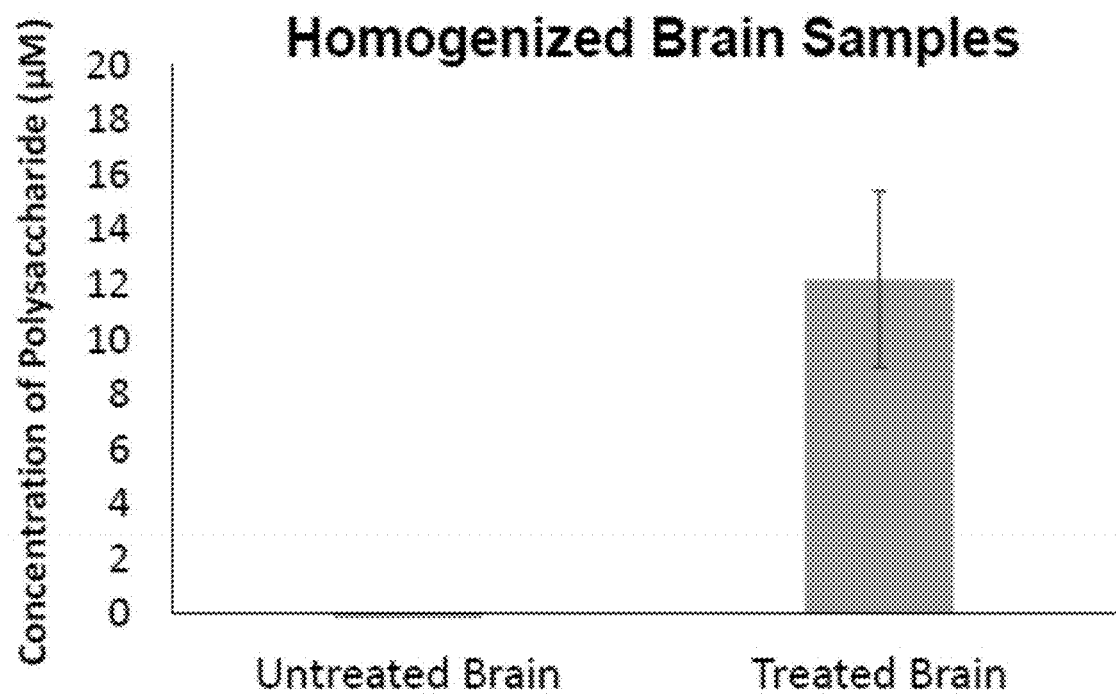
FIG. 37C: Fluorescent and colorimetric values of ANTS-midi-GAGR before and after three 75% ethanol washes (mean±standard error, n=5).
FIG. 38A: The RFUs (mean±standard error) of the brain cytosols from animals administered with none or 1 mM ANTS-midi-GAGR. Brains were dissected out of rats that were sacrificed at 6 h after administration (n=3).

According to the standard curves, the RFU of ANTS-polysaccharide in the pellet before washes was ~7493 and its absorbance at 490 nm was ~0.269 (FIG. 37C).

After three washes, the mean RFU of ANTS-polysaccharide was significantly reduced to ~4910 while the absorbance at 490 nm was only slightly reduced to 0.219. The values of RFU and absorbance at 490 nm were not further decreased by more washes after the third wash, showing that most of the loosely-associated free ANTS was removed from the pellet of ANTS-midi-GAGR.

According to the standard curves, the final pellet contained 16.18 mM ANTS and 1.55 mM midi-GAGR, which give the ratio of about 10:1 for ANTS to midi-GAGR.

It is to be noted that one ANTS was supposed to be conjugated to one reducing end of a polysaccharide, thus yielding the ratio of 1:1 for ANTS to midi-GAGR. However, more ANTS appeared to be conjugated to other hydroxyl groups on midi-GAGR, yielding the 10:1 ratio for ANTS to midi-GAGR. Polysaccharide was labeled with ANTS using EDC [1-Ethyl-3-3-dimethylaminopropyl carbodiimide] in order to conjugate the amino group of ANTS to the carboxyl group of glucuronic acid of midi-GAGR. However, the EDC conjugate of ANTS-midi-GAGR was not precipitated by 75% ethanol, showing that the EDC conjugate cannot be purified using 75% ethanol.)

Measurement of the Amount of ANTS-Polysaccharide that Enters the Brain and Blood Circulation Administration and Measurement of ANTS-Midi-GAGR To examine the BBB-permeability of ANTS-midi-GAGR, 40 µL of 1 mM ANTS-midi-GAGR was administered into the nostril of Sprague-Dawley rats (male, 350-490 g, age of 8 weeks).

Rats were quickly anesthetized in an isoflurane induction chamber (isoflurane from Henry Schein Animal Health [Dublin, Ohio]). 5% isoflurane is administered into animal by a vaporizer with oxygen flowmeter (0.8-1.5 L/min). The percent of isoflurane was later adjusted to 2% until animal loses righting reflex.

20 µL of 1 mM ANTS-midi-GAGR was intra-nasally administered to each nostril. Animals were kept in the anesthetized condition for 5 min after the administration of ANTS-polysaccharide to prevent the squirting-out of ANTS-polysaccharide from the noses.

At 6 h after the administration of ANTS-polysaccharide, animals were sacrificed using a guillotine. About 1 mL of trunk blood was collected in a vial immediately after decapitation. Trunk blood was incubated at room temperature for 1 h to coagulate and centrifuged at 3,000×g for 10 min to remove the coagulated, which yields ~400 µL of serum. Simultaneously, the olfactory bulb tract and whole brain were also dissected out of the head of the decapitated animal. The brain and olfactory bulb tract were washed with 0.9% saline and homogenized in the equivalent volume of 1×PMEE buffer (pH 7.0; 35 mM KOH, 35 mM PIPES, 5 mM MgSO4, 1 mM EGTA, 1% BSA, and 0.5 mM EDTA) containing 1% Igepal CA-630 using a glass homogenizer (Wheaton, Millville, N.J.). The homogenized brain extract was centrifuged at 14,500×g for 20 min and at 100,000×g for 30 min to obtain brain cytosol. The amounts of ANTS-polysaccharide in the serum and the cytosols extracted from olfactory bulb and brain were measured by fluorometry.

Quantification of ANTS-midi-GAGR in Brain and Blood

The amounts of ANTS-midi-GAGR in the samples were quantified using the standard curve of ANTS and the conjugation ratio of 10:1 for ANTS to midi-GAGR (FIGS. 37A-37B).

The RFUs of the cytosols extracted from the olfactory bulb tracts of all rats were lower than ~50 RFUs that were the same as the basal fluorescence units of those of rats administered with saline alone, thus showing that little ANTS-midi-GAGR was routed to the olfactory bulb tract.

The RFUs of the sera and brain cytosols were significantly above 50 RFUs. The RFU values of brain cytosols and sera were converted to the concentrations of midi-GAGR using the ratio of 10:1 for ANTS to midi-GAGR. The brain cytosols and sera of the rats administered with ANTS-midi-GAGR contained ~12 µM (FIG. 20A) and ~28 µM (FIG. 20B), respectively, of midi-GAGR. Thus, intra-nasally administered midi-GAGR can enter the brain and blood circulation.

Examination of the Structural Intactness of ANTS-Midi-GAGR in the Serum

It was possible that the fluorescence of the sera was emitted from free ANTS that might be generated by the cleavage of ANTS-midi-GAGR during the circulation in the blood. Therefore, it was examined whether ANTS-midi-GAGR in the sera was structurally intact or not by 75% ethanol precipitation that only precipitate ANTS-midi-GAGR but not free ANTS.

100 µL of the supernatant was added with 300 µL of 100% ethanol to make the final concentration of 75% ethanol and centrifuged at 3,000×g to precipitate serum polysaccharides including ANTS-midi-GAGR, leaving polysaccharide-free ANTS in the supernatant. The pellet was resuspended in the equivalent volume of water to that of the supernatant. The RFUs of the supernatant and pellet resuspension were measured by fluorometry. The RFUs of the supernatant fell down to below 50 while those of the pellet resuspension were close to those of the supernatant before ethanol precipitation. This shows that most of ANTS-midi-GAGR was structurally intact in the serum.

Examination of the Binding of ANTS-Midi-GAGR to Serum Protein

Also examined was whether ANTS-midi-GAGR in the serum bound to serum proteins like albumin or not. TCA was used to precipitate all the proteins and protein-bound molecules including polysaccharides but leave protein-free polysaccharides in the supernatant.

Figures 38B, 38C:
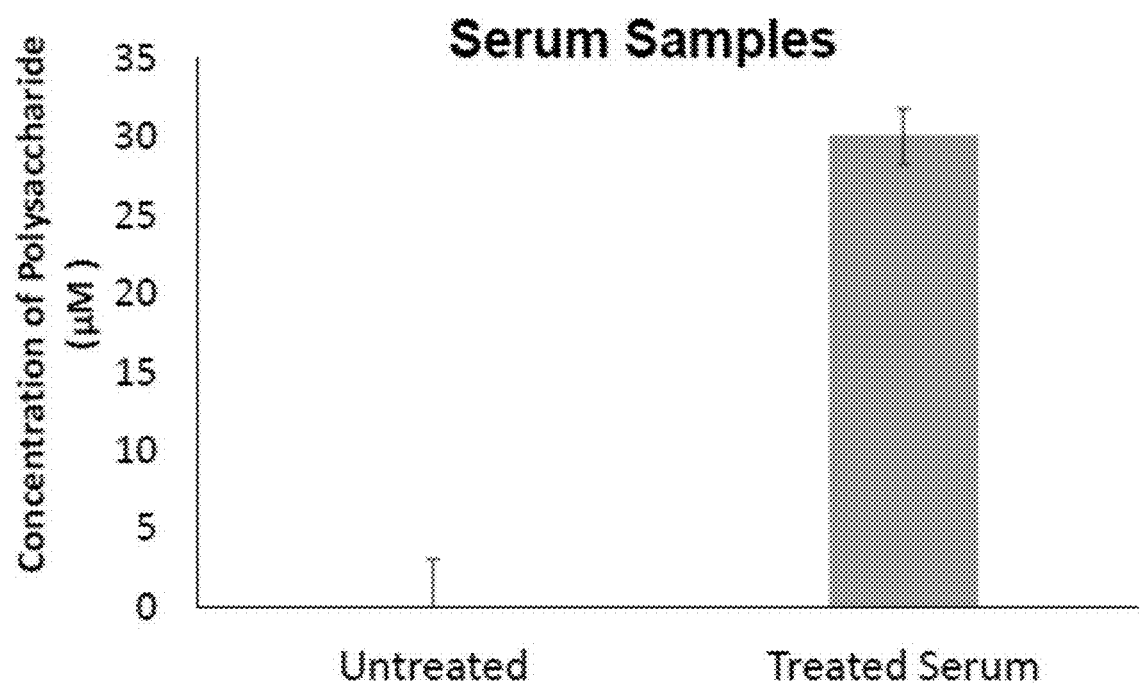
FIG. 38B: The RFUs (mean±standard error) of the sera from animals administered with none or 1 mM ANTS-midi-GAGR. Serum samples were collected from rats that were sacrificed at 6 h after administration (n=4).
FIG. 38C: The RFUs (mean±standard error) of the supernatants and pellets of TCA precipitation and ethanol precipitation of sera (n=5).
Figure 39:
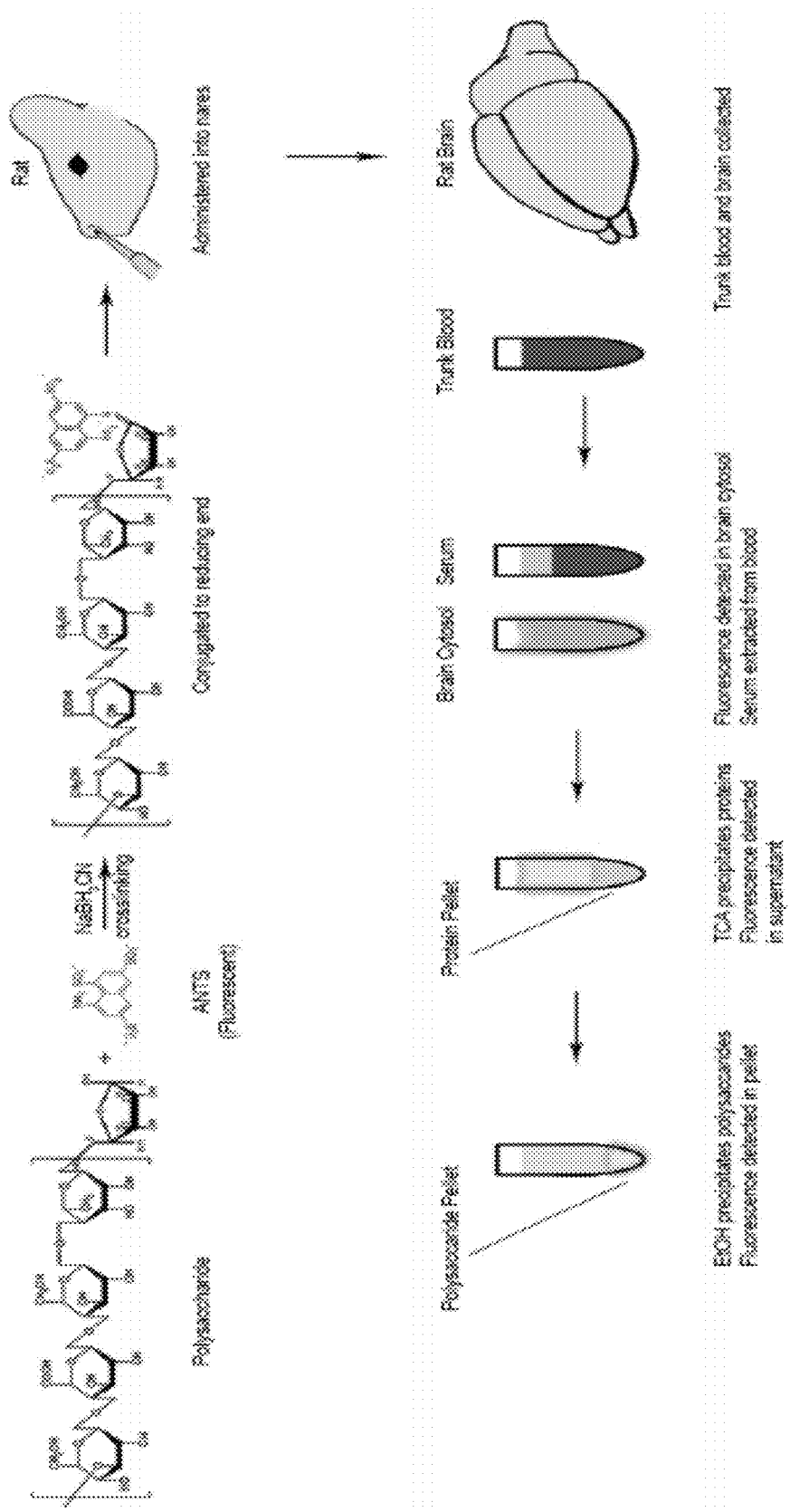
FIG. 39: Schematic illustration showing a method to examine the BBB-permeability and tissue distribution of a target polysaccharide in animal. A polysaccharide was conjugated with fluorescent 8-aminonaphthalene-1,3,6-trisulfonic acid disodium salt (ANTS) for tracking in animals. ANTS-tagged polysaccharide was separated from unconjugated free ANTS using 75% ethanol. After ANTS-polysaccharide was intra-nasally administered into animals, the amounts of ANTS-polysaccharide in the brain and the serum were quantified by fluorocytometry. Free ANTS-polysaccharide was separated from serum proteins using 75% ethanol and trichloroacetic acid (TCA).

100 µL of serum sample in a microtube was added with 10 µL of TCA to make the final concentration of 10% TCA, incubated at 4° C. for 10 min, and centrifuged at 15,700×g for 5 min. The supernatant over the pellet was transferred to a new tube and the pellet containing proteins was resuspended in 100 µL of water. The RFU of the pellet resuspension was measured by fluorometry. The RFUs of the pellet resuspension was below the basal fluorescent units (50 RFUs) while those of the supernatants still yielded ~201 RFUs (FIG. 38C), thus showing that little ANTS-polysaccharide was precipitated along with serum proteins.

100 µL of the supernatant was added with 300 µL of 100% ethanol to make the final concentration of 75% ethanol and centrifuged at 3,000×g to precipitate serum polysaccharides including ANTS-midi-GAGR. The pellet was resuspended in 50 µL water. The RFUs of the supernatant and pellet resuspension were measured by fluorometry. The RFU of the supernatant was below the basal fluorescent units (50 RFUs) while the pellet resuspension yielded ~201 RFUs, thus showing that most ANTS-midi-GAGR remained intact in the supernatant after TCA precipitation.

ANTS-midi-GAGR that enters the brain and blood circulation does maintain its intact structure inside animal and does not bind to serum protein for 6 h after its intra-nasal administration. Given that the cerebrospinal fluid should contain less digestive enzymes than the peripheral blood, it is now shown herein that ANTS-midi-GAGR in the brain should be intact as well.)

All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A method of enhancing collagen production in cells in a subject in need thereof, the method consisting of:
   administering an effective amount of a low acyl gellan gum (LA-GAGR) cleavage product to cells as the active ingredient that enhances collagen production in the cells, and
   enhancing collagen production in the cells;
   wherein the LA-GAGR comprises a polysaccharide based on tetrasaccharide repeating units having a molecular weight of approximately 99,600 end and a chemical structure of [D-Glc($\beta$1→4)D-GlcA($\beta$1→4)D-Glc($\beta$1→4)L-Rha($\alpha$1→3)n); and
   wherein the LA-GAGR cleavage product comprises midi-LA-GAGR or mini-LA-GAGR.

2. The method of claim 1, wherein the LA-GAGR cleavage product is produced in the subject by enzymatic digestion of LA-GAGR by $\alpha$(1→3)-glucosidase.

3. The method of claim 2, wherein the midi-LA-GAGR has a molecular weight of about 4,775 g/mol.

4. The method of claim 2, wherein the mini-LA-GAGR has a molecular weight of about 718 g/mol.

5. The method of claim 1, wherein the cells comprise cartilage cells or mesenchymal stem cells.

* * * * *

UNITED STATES PATENT AND TRADEMARK OFFICE
CERTIFICATE OF CORRECTION

| | | |
|---|---|---|
| PATENT NO. | : 11,197,885 B2 | Page 1 of 1 |
| APPLICATION NO. | : 15/447620 | |
| DATED | : December 14, 2021 | |
| INVENTOR(S) | : Joshua J. Park and Dong-Shik Kim | |

It is certified that error appears in the above-identified patent and that said Letters Patent is hereby corrected as shown below:

In the Claims

Column 42, Claim 1, Line 49 please correct:
"approximately 99,600 end and a chemical"

To:
--approximately 99,600 g/mol and a chemical--

Signed and Sealed this
Twenty-second Day of March, 2022

Drew Hirshfeld
*Performing the Functions and Duties of the
Under Secretary of Commerce for Intellectual Property and
Director of the United States Patent and Trademark Office*